United States Patent
Hentze et al.

(10) Patent No.: US 6,610,508 B1
(45) Date of Patent: Aug. 26, 2003

(54) TRANSLATION DRIVER SYSTEM AND METHODS FOR USE THEREOF

(75) Inventors: Matthias W. Hentze, St. Leon-Rot (DE); Ennio De Gregorio, Heidelberg (DE)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/264,512

(22) Filed: Mar. 8, 1999

(51) Int. Cl.$^7$ ............................ C12P 21/06; C12N 1/20; C12N 5/00; C07H 21/02; C07H 21/04

(52) U.S. Cl. ................... 435/69.1; 435/252.3; 435/325; 536/23.1; 536/23.4

(58) Field of Search ............................... 536/24.1, 23.1, 536/23.4; 514/44, 2; 435/456, 325, 252.1, 252.3, 69.1, 69.2

(56) References Cited

U.S. PATENT DOCUMENTS 5,859,227 A * 1/1999 Giordano et al. .......... 536/24.1
6,060,273 A   5/2000 Dirks et al.

FOREIGN PATENT DOCUMENTS

| DE | 19514310 A | 10/1996 |
|---|---|---|
| WO | WO 94/05785 | 3/1994 |
| WO | WO 94/24870 | 11/1994 |

OTHER PUBLICATIONS

Borman et al., 1997, "ELF4G and Its Proteolytic Cleavage Products: Effect on Initiation of Protein Synthesis From Capped, Uncapped and IRES–Containing mRNAs", RNA 3(2):186–196.

Craig et al., 1998, "Interaction of Polyadenylate–Binding Protein With the eIF4G Homologue PAIP Enhances Translation", Nature 392: 520–523.

DeGregorio et al., 1999, "Translation Driven By an ELF4G Domain In Vivo", EMBO J. 18(17):4865–4874.

Johannes and Sarnow, 1997, "ELF4G and its Proteolytic Cleavage Products: Effect on Initiation of Protein Synthesis From Capped, Uncapped, and IRES–Containing mRNAs", RNA 3(2): 186–196.

Yan et al., 1992, "Amino Acid Sequence of the Human Protein Synthesis Initiation Factor eIF–4γ", The Journal of Biological Chemistry 267(15): 23226–23231.

Allen et al., 1992, "Isolation and sequence of the cDNAs encoding the subunits of the isozyme form of wheat protein synthesis initiation factor 4F", J. Biol. Chem. 267:23232–236.

Chen, et al., 1995, "Initiation of protein synthesis by the eukaryotic translational apparatus on circular RNAs", Science 268:415–517.

De Gregorio, et al., 1998, "An IRES by Rational Design: Function of eIF4G in Ribosome Recruitment" Abstracts of papers presented at the 1998 meeting on Translational Control, Sep. 9–13, 1998, Cold Spring Harbor Laboratory, Cold Spring Harbor, New York.

De Gregorio, et al., 1998, "Translational activation of uncapped mRNAs by the central part of human eIF4G is 5' end", RNA 4:828–36.

Gallie, D., 1991, "The cap and poly(A) tail function synergistically to regulate mRAN translational efficiency", Genes & Dev. 5:2108–2116.

Goossen, et al, 1990, "Translational repression by a complex between the iron–responsive element of ferritin mRNA and specific cytoplasmic binding protein is position–dependent in vivo", EMBO J. 9:4127–4133.

Goyer, C. et al., 1993, "TIF4631 & TIF4632: Two yeast genes encoding the high–molecular weight subunits of the cap–binding protein complex (eukaryotic initiation factor 4F) contain an RNA recognition motif–like sequence and carry out an essential function", Mol. Cell. Biol. 13:4860–4874.

Gradi et al., 1998, "A novel functional human eukaryotic translation initiation factor 4G", Mol. Cell Biol. 18:334–342.

Hentze and Kuhn, 1996, "Molecular control of vertebrate iron metabolism: mRNA–based regulatory circuits operated by iron, nitric oxide, and oxidative stress", Proc. Natl. Acad. Sci. USA 93:8175–8182.

Hentz, et al., 1997, "eIf4G: a multipurpose ribosome adapter?", Science 275:500–501.

Imataka, et al., 1997, "Human eukaryotic translation initiation factor 4G (eIF4G) possesses two separate independent binding sites for eIF4A", Mol. Cell. Biol. 17:6940–6947.

(List continued on next page.)

*Primary Examiner*—Deborah Crouch
*Assistant Examiner*—Joseph Woitach
(74) *Attorney, Agent, or Firm*—David R Preston & Associates

(57) ABSTRACT

The present method relates to the translational activation of genes using the ribosome recruitment protein, eIF4G or an eIF4G-like protein. The invention relates to the translation of RNA molecules containing heterologous protein-binding sites, which RNA molecules encode one, two, three or more proteins. The invention provides products and methods for the identification of RNA-binding proteins. The invention further provides a system by which protein—protein interactions and inhibitors or enhancers of these interactions may be identified. Further, the invention provides products and methods to provide a cell with one or more therapeutic proteins. The invention provides products and methods for controlling the levels of translation of such proteins. The invention provides products and methods to control the translation and stoichiometry of multiple subunit proteins. The invention provides products for and methods of screening for proteins which interact with an RNA binding site, and methods for identifying RNA binding sites.

107 Claims, 20 Drawing Sheets

OTHER PUBLICATIONS

Figure 1A:
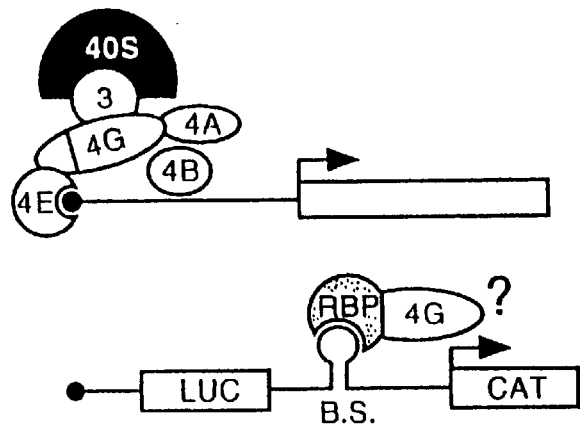

Imataka et al., 1997, "A new translational regulator with homology to eukaryotic translation initiation factor 4G", EMBO J. 16:817–825.

Imataka, et al., 1998, "A newly identified N–terminal amino acid sequence of human eIF4G binds poly(A)–binding protein and functions in poly(A)–dependent translation", EMBO J. 17:7480–7489.

Kollmus, et al., 1996, "Regulated ribosomal frameshifting by an RNA–protein interaction", RNA 2:316–323.

Kolupaeva, V., et al., 1998, "Translation eukaryotic initiation factor 4G recognizes a specific structural element within the internal ribosome entry site of encephalomyocardititis virus RNA", J. Biol. Chem. 273:18599–604.

Kozak, M., 1986, "Influences of mRNA secondary structure on initiation by eukaryotic ribosomes", Proc. Natl. Acad. Sci. USA 83:2850–2854.

Lamphear, et al., 1993, "Mapping the cleavage site in protein synthesis initiation factor eIF–4γ of the 2A proteases from human coxsackievirus and rhinovirus", J. Biol. Chem. 268:19200–19203.

Lamphear, et al., 1995, "Mapping of functional domains in eukaryotic protein synthesis initiation factor 4G (eIF4G) with picornaviral proteases. Implications for cap–dependent and cap–independent translational initiation", J. Biol. Chem. 270:21975–21983.

Lowary and Uhlenbeck, 1987, "An RNA mutation that increases the affinity of an RNA–protein interaction", Nucl. Acids Res. 15:10483–10493.

Mader, et al., 1995, "The translation initiation factor eIF–4E binds to a common motif shared by the translation factor eIF–4γ and the translation repressors", Mol. Cell. Biol. 15:4990–4997.

Muckenthaler M. et al., 1998, "IRP–1 binding to ferritin mRNA prevents the recruitment of the small ribosomal subunit by the cap–binding complex eIF4F", Molecular Cell 2:383–388.

Pantopoulos, et al., 1995, "Differential regulation of two related RNA–binding proteins, iron regulatory protein (IRP) and IRPB", RNA 1:155–163.

Pantopoulos, et al., 1995, "Nitric oxide signaling to iron-regulatory protein: direct control of ferritin mRNA translation and transferrin receptor mRNA stability in transfected fibroblasts", Proc. Natl. Acad. Sci. USA 92:1267–1271.

Paraskeva, et al., 1999, "Ribosomal pausing and scanning arrest as mechanisms of translational regulation from cap-distal iron–responsive elements", Mol. Cell. Biol. 19:807–816.

Pestova, et al., 1996, "Functional dissection of eukaryotic initiation factor 4F: the 4A subunit and the central domain of the 4G subunit are sufficient to mediate internal entry of 43S pre–initiation complexes", Mol. Cell. Biol. 16:6870–6878.

Preiss, et al., 1998, "Poly–(A)–tail–promoted translation in yeast: implications for translational control", RNA 4:1321–1331.

Pyronnet, S. et al., 1999, "Human eukaryotic translation initiation factor 4G (eIF4G) recruits mnk1 to phosphorylate eIF4E", EMBO J. 13:270–279.

Reynolds, J. E. et al., 1995, "Unique features of internal initiation of hepatitis C virus RNA translation", EMBO J. 14:6010–6020.

Sachs, et al., 1997, "Starting at the beginning, middle, and end: translation initiation in eukaryotes", Cell 89:831–838.

Scherly et al., 1989, "Identification of the RNA binding segment of human U1 A protein and definition of its binding site on U1 snRNA", EMBO J. 8:4163–4170.

Stripecke, et al., 1992, "Bacteriophage and spliceosomal proteins function as position–dependent *cis/trans* repressors of mRNA translation in vitro", Nucl. Acids Res. 20:5555–5564.

Tan and Frankel, 1995, "Structral variety of arginine–rich RNA–binding peptides", Proc. Natl. Acad. Sci. USA 92:5282–5286.

Tarun, et al., 1996, "Association of the yeast poly(A) tail binding protein with translation initiation factor eIF–4G", EMBO J. 15:7168–7177.

Wells, et al., 1998, "Circulation of mRNA by eukaryotic translation initiation factors", Mol. Cell 2:135–40.

Witherell et al., 1991, "Specific interaction between RNA phage coat proteins and RNA", Progr. Nucl. Acids Res. Mol. Biol. 40: 185–220.

* cited by examiner

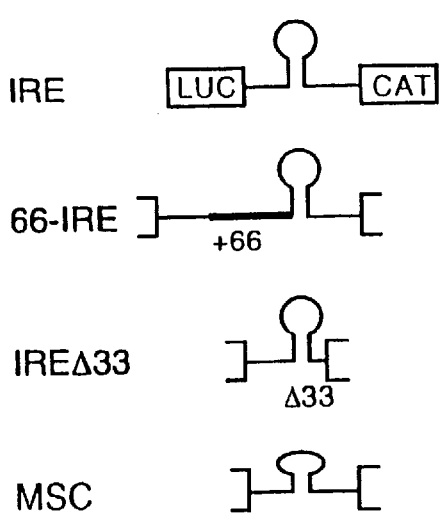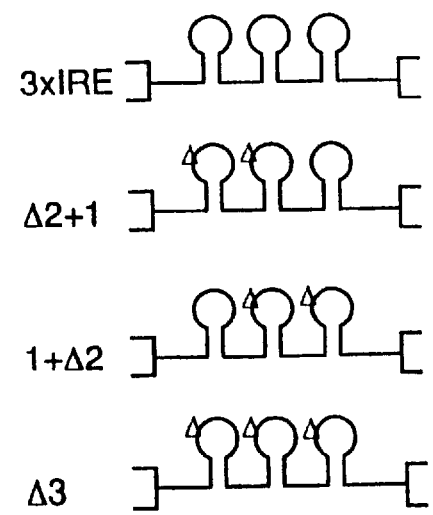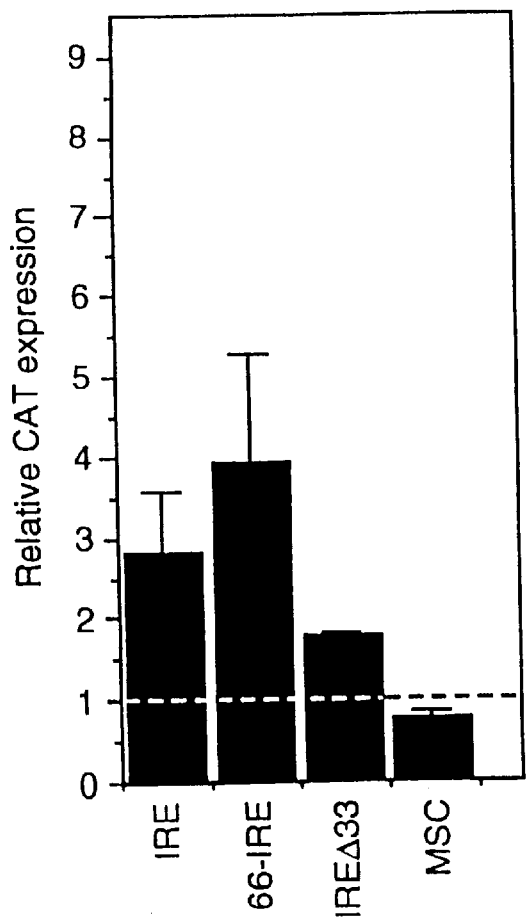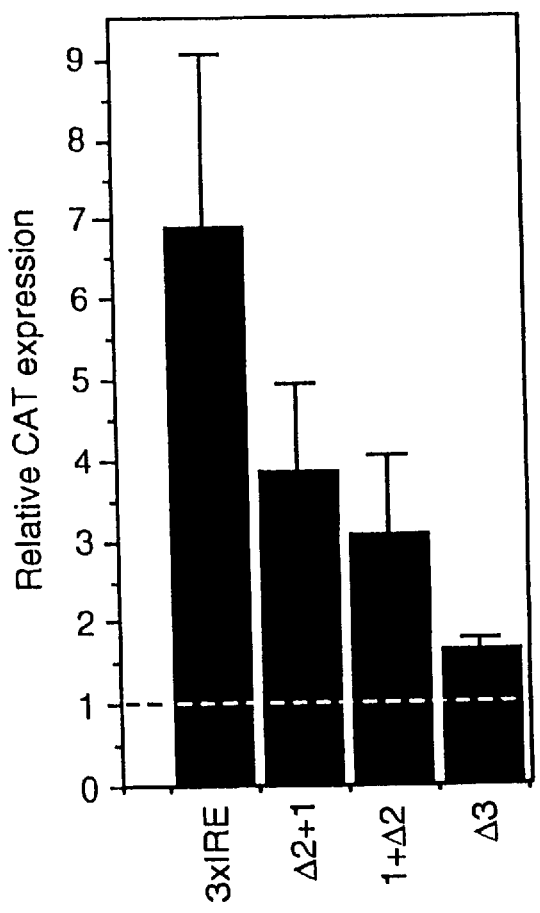
FIG.2A  FIG.2B

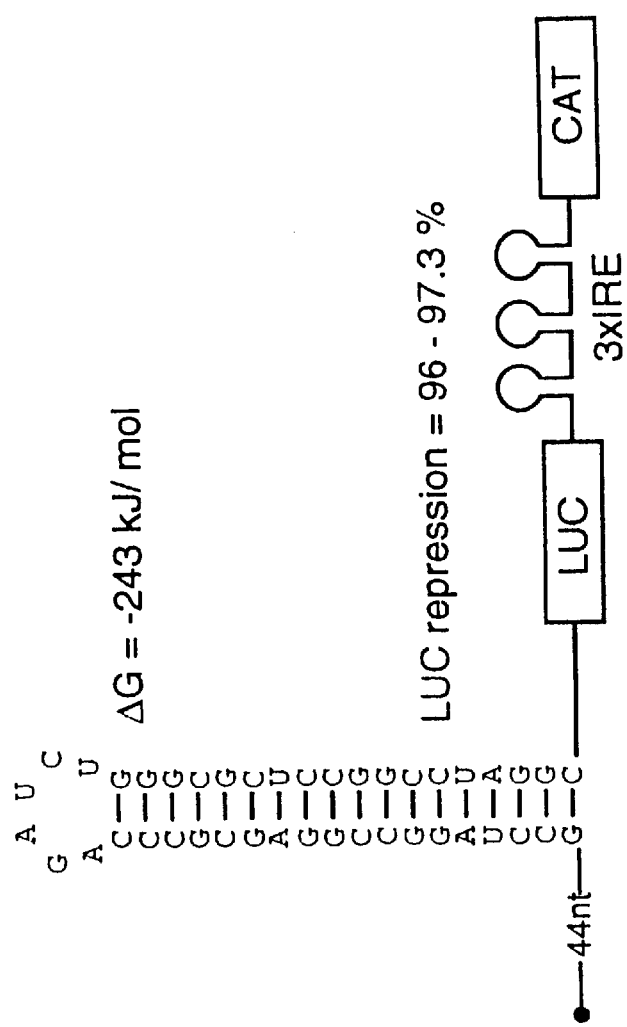
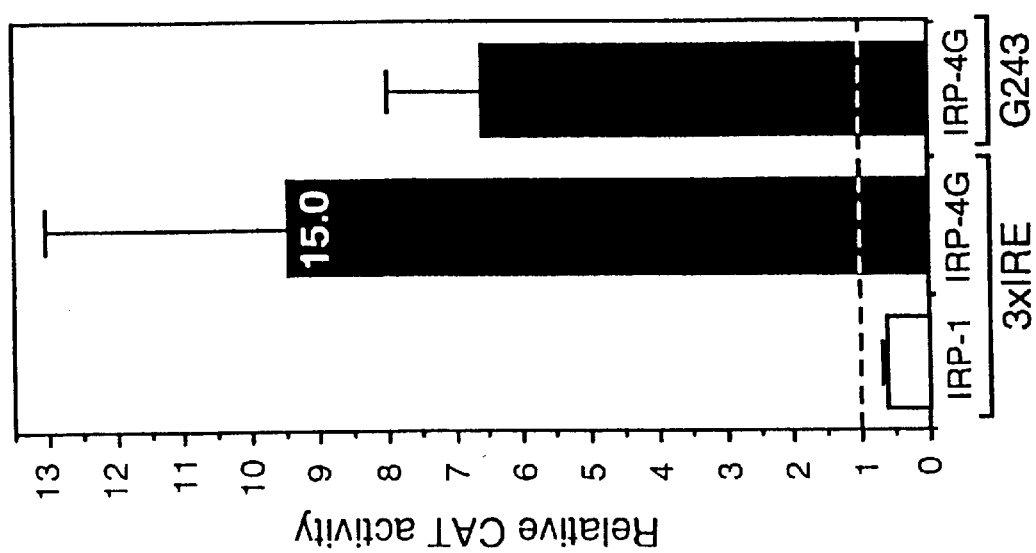
FIG. 4B
FIG. 4A

```
CAAGCGACAC AA ATG AAC ACG CCT TCT CAG CCC CGC CAG CAC TTC TAC CCT    51
              Met Asn Thr Pro Ser Gln Pro Arg Gln His Phe Tyr Pro
               1               5                  10

AGC CGG GCC CAG CCC CCG AGC AGT GCA GCC TCC CGA GTG CAG AGT GCA      99
Ser Arg Ala Gln Pro Pro Ser Ser Ala Ala Ser Arg Val Gln Ser Ala
 15              20                  25

GCC CCT GCC CGC CCT GGC CCA GCT GCC CAT GTC TAC CCT GCT GGA TCC     147
Ala Pro Ala Arg Pro Gly Pro Ala Ala His Val Tyr Pro Ala Gly Ser
 30              35                  40                  45

CAA GTA ATG ATG ATC CCT TCC CAG ATC TCC TAC CCA GCC TCC CAG GGG     195
Gln Val Met Met Ile Pro Ser Gln Ile Ser Tyr Pro Ala Ser Gln Gly
                 50                  55                  60

GCC TAC TAC ATC CCT GGA CAG GGG CGT TCC ACA TAC GTT GTC CCG ACA     243
Ala Tyr Tyr Ile Pro Gly Gln Gly Arg Ser Thr Tyr Val Val Pro Thr
                 65                  70                  75

CAG CAG TAC CCT GTG CAG CCA GGA GCC CCA GGC TTC TAT CCA GGT GCA     291
Gln Gln Tyr Pro Val Gln Pro Gly Ala Pro Gly Phe Tyr Pro Gly Ala
         80                  85                  90

AGC CCT ACA GAA TTT GGG ACC TAC GCT GGC GCC TAC TAT CCA GCC CAA     339
Ser Pro Thr Glu Phe Gly Thr Tyr Ala Gly Ala Tyr Tyr Pro Ala Gln
         95                  100                 105

GGG GTG CAG CAG TTT CCC ACT GGC GTG GCC CCC GCC CCA GTT TTG ATG     387
Gly Val Gln Gln Phe Pro Thr Gly Val Ala Pro Ala Pro Val Leu Met
110                  115                 120                 125

AAC CAG CCA CCC CAG ATT GCT CCC AAG AGG GAG CGT AAG ACG ATC CGA     435
Asn Gln Pro Pro Gln Ile Ala Pro Lys Arg Glu Arg Lys Thr Ile Arg
                 130                 135                 140

ATT CGA GAT CCA AAC CAA GGA GGA AAG GAT ATC ACA GAG GAG ATC ATG     483
Ile Arg Asp Pro Asn Gln Gly Gly Lys Asp Ile Thr Glu Glu Ile Met
                 145                 150                 155

TCT GGG GCC CGC ACT GCC TCC ACA CCC ACC CCT CCC CAG ACG GGA GGC     531
Ser Gly Ala Arg Thr Ala Ser Thr Pro Thr Pro Pro Gln Thr Gly Gly
         160                 165                 170

GGT CTG GAG CCT CAA GCT AAT GGG GAG ACG CCC CAG GTT GCT GTC ATT     579
Gly Leu Glu Pro Gln Ala Asn Gly Glu Thr Pro Gln Val Ala Val Ile
         175                 180                 185

GTC CGG CCA GAT GAC CGG TCA CAG GGA GCA ATC ATT GCT GAC CGG CCA     627
Val Arg Pro Asp Asp Arg Ser Gln Gly Ala Ile Ile Ala Asp Arg Pro
190                 195                 200                 205
```

FIG. 9A

```
GGG CTG CCT GGC CCA GAG CAT AGC CCT TCA GAA TCC CAG CCT TCG TCG    675
Gly Leu Pro Gly Pro Glu His Ser Pro Ser Glu Ser Gln Pro Ser Ser
        210             215                 220

CCT TCT CCG ACC CCA TCA CCA TCC CCA GTC TTG GAA CCG GGG TCT GAG    723
Pro Ser Pro Thr Pro Ser Pro Ser Pro Val Leu Glu Pro Gly Ser Glu
            225             230                 235

CCT AAT CTC GCA GTC CTC TCT ATT CCT GGG GAC ACT ATG ACA ACT ATA    771
Pro Asn Leu Ala Val Leu Ser Ile Pro Gly Asp Thr Met Thr Thr Ile
        240             245                 250

CAA ATG TCT GTA GAA GAA TCA ACC CCC ATC TCC CGT GAA ACT GGG GAG    819
Gln Met Ser Val Glu Glu Ser Thr Pro Ile Ser Arg Glu Thr Gly Glu
        255             260                 265

CCA TAT CGC CTC TCT CCA GAA CCC ACT CCT CTC GCC GAA CCC ATA CTG    867
Pro Tyr Arg Leu Ser Pro Glu Pro Thr Pro Leu Ala Glu Pro Ile Leu
270             275                 280                 285

GAA GTA GAA GTG ACA CTT AGC AAA CCG GTT CCA GAA TCT GAG TTT TCT    915
Glu Val Glu Val Thr Leu Ser Lys Pro Val Pro Glu Ser Glu Phe Ser
            290                 295                 300

TCC AGT CCT CTC CAG GCT CCC ACC CCT TTG GCA TCT CAC ACA GTG GAA    963
Ser Ser Pro Leu Gln Ala Pro Thr Pro Leu Ala Ser His Thr Val Glu
            305                 310                 315

ATT CAT GAG CCT AAT GGC ATG GTC CCA TCT GAA GAT CTG GAA CCA GAG    1011
Ile His Glu Pro Asn Gly Met Val Pro Ser Glu Asp Leu Glu Pro Glu
            320             325                 330

GTG GAG TCA AGC CCA GAG CTT GCT CCT CCC CCA GCT TGC CCC TCC GAA    1059
Val Glu Ser Ser Pro Glu Leu Ala Pro Pro Pro Ala Cys Pro Ser Glu
        335                 340                 345

TCC CCT GTG CCC ATT GCT CCA ACT GCC CAA CCT GAG GAA CTG CTC AAC    1107
Ser Pro Val Pro Ile Ala Pro Thr Ala Gln Pro Glu Glu Leu Leu Asn
350                 355                 360                 365

GGA GCC CCC TCG CCA CCA GCT GTG GAC TTA AGC CCA GTC AGT GAG CCA    1155
Gly Ala Pro Ser Pro Pro Ala Val Asp Leu Ser Pro Val Ser Glu Pro
                370                 375                 380

GAG GAG CAG GCC AAG GAG GTG ACA GCA TCA GTG GCG CCC CCC ACC ATC    1203
Glu Glu Gln Ala Lys Glu Val Thr Ala Ser Val Ala Pro Pro Thr Ile
            385                 390                 395

CCC TCT GCT ACT CCA GCT ACG GCT CCT TCA GCT ACT TCC CCA GCT CAG    1251
Pro Ser Ala Thr Pro Ala Thr Ala Pro Ser Ala Thr Ser Pro Ala Gln
            400                 405                 410

GAG GAG GAA ATG GAA GAA GAA GAA GAA GAG GAA GAA GGA GAA GCA GGA    1299
Glu Glu Glu Met Glu Glu Glu Glu Glu Glu Glu Glu Gly Glu Ala Gly
        415                 420                 425
```

FIG. 9B

```
GAA GCA GGA GAA GCT GAG AGT GAG AAA GGA GGA GAG GAA CTG CTC CCC   1347
Glu Ala Gly Glu Ala Glu Ser Glu Lys Gly Gly Glu Glu Leu Leu Pro
430                 435                 440                 445

CCA GAG AGT ACC CCT ATT CCA GCC AAC TTG TCT CAG AAT TTG GAG GCA   1395
Pro Glu Ser Thr Pro Ile Pro Ala Asn Leu Ser Gln Asn Leu Glu Ala
                450                 455                 460

GCA GCA GCC ACT CAA GTG GCA GTA TCT GTG CCA AAG AGG AGA CGG AAA   1443
Ala Ala Ala Thr Gln Val Ala Val Ser Val Pro Lys Arg Arg Arg Lys
            465                 470                 475

ATT AAG GAG CTA AAT AAG AAG GAG GCT GTT GGA GAC CTT CTG GAT GCC   1491
Ile Lys Glu Leu Asn Lys Lys Glu Ala Val Gly Asp Leu Leu Asp Ala
        480                 485                 490

TTC AAG GAG GCG AAC CCG GCA GTA CCA GAG GTG GAA AAT CAG CCT CCT   1539
Phe Lys Glu Ala Asn Pro Ala Val Pro Glu Val Glu Asn Gln Pro Pro
    495                 500                 505

GCA GGC AGC AAT CCA GGC CCA GAG TCT GAG GGC AGT GGT GTG CCC CCA   1587
Ala Gly Ser Asn Pro Gly Pro Glu Ser Glu Gly Ser Gly Val Pro Pro
510                 515                 520                 525

CGT CCT GAG GAA GCA GAT GAG ACC TGG GAC TCA AAG GAA GAC AAA ATT   1635
Arg Pro Glu Glu Ala Asp Glu Thr Trp Asp Ser Lys Glu Asp Lys Ile
                530                 535                 540

CAC AAT GCT GAG AAC ATC CAG CCC GGG GAA CAG AAG TAT GAA TAT AAG   1683
His Asn Ala Glu Asn Ile Gln Pro Gly Glu Gln Lys Tyr Glu Tyr Lys
            545                 550                 555

TCA GAT CAG TGG AAG CCT CCA AAC CTA GAG GAG AAA AAA CGT TAC GAC   1731
Ser Asp Gln Trp Lys Pro Pro Asn Leu Glu Glu Lys Lys Arg Tyr Asp
        560                 565                 570

CGT GAG TTC CTG CTT GGT TTT CAG TTC ATC TTT GCC AGT ATG CAG AAG   1779
Arg Glu Phe Leu Leu Gly Phe Gln Phe Ile Phe Ala Ser Met Gln Lys
    575                 580                 585

CCA GAG GGA TTG CCA CAT ATC AGT GAC GTG GTG CTG GAC AAG GCC AAT   1827
Pro Glu Gly Leu Pro His Ile Ser Asp Val Val Leu Asp Lys Ala Asn
590                 595                 600                 605

AAA ACA CCA CTG CGG CCA CTG GAT CCC ACT AGA CTA CAA GGC ATA AAT   1875
Lys Thr Pro Leu Arg Pro Leu Asp Pro Thr Arg Leu Gln Gly Ile Asn
                610                 615                 620

TGT GGC CCA GAC TTC ACT CCA TCC TTT GCC AAC CTT GGC CGG ACA ACC   1923
Cys Gly Pro Asp Phe Thr Pro Ser Phe Ala Asn Leu Gly Arg Thr Thr
            625                 630                 635

CTT AGC ACC CGT GGG CCC CCA AGG GGT GGG CCA GGT GGG GAG CTG CCC   1971
Leu Ser Thr Arg Gly Pro Pro Arg Gly Gly Pro Gly Gly Glu Leu Pro
        640                 645                 650
```

FIG. 9C

```
CGT GGG CCG CAG GCT GGC CTG GGA CCC CGG CGC TCT CAG CAG GGA CCC   2019
Arg Gly Pro Gln Ala Gly Leu Gly Pro Arg Arg Ser Gln Gln Gly Pro
    655             660             665

CGA AAA GAA CCA CGC AAG ATC ATT GCC ACA GTG TTA ATG ACC GAA GAT   2067
Arg Lys Glu Pro Arg Lys Ile Ile Ala Thr Val Leu Met Thr Glu Asp
670             675             680             685

ATA AAA CTG AAC AAA GCA GAG AAA GCC TGG AAA CCC AGC AGC AAG CGG   2115
Ile Lys Leu Asn Lys Ala Glu Lys Ala Trp Lys Pro Ser Ser Lys Arg
            690             695             700

ACG GCG GCT GAT AAG GAT CGA GGG GAA GAA GAT GCT GAT GGC AGC AAA   2163
Thr Ala Ala Asp Lys Asp Arg Gly Glu Glu Asp Ala Asp Gly Ser Lys
        705             710             715

ACC CAG GAC CTA TTC CGC AGG GTG CGC TCC ATC CTG AAT AAA CTG ACA   2211
Thr Gln Asp Leu Phe Arg Arg Val Arg Ser Ile Leu Asn Lys Leu Thr
    720             725             730

CCC CAG ATG TTC CAG CAG CTG ATG AAG CAA GTG ACG CAG CTG GCC ATC   2259
Pro Gln Met Phe Gln Gln Leu Met Lys Gln Val Thr Gln Leu Ala Ile
    735             740             745

GAC ACC GAG GAA CGC CTC.AAA GGG GTC ATT GAC CTC ATT TTT GAG AAG   2307
Asp Thr Glu Glu Arg Leu Lys Gly Val Ile Asp Leu Ile Phe Glu Lys
750             755             760             765

GCC ATT TCA GAG CCC AAC TTC TCT GTG GCC TAT GCC AAC ATG TGC CGC   2355
Ala Ile Ser Glu Pro Asn Phe Ser Val Ala Tyr Ala Asn Met Cys Arg
            770             775             780

TGC CTC ATG GCG CTG AAA GTG CCC ACT ACG GAA AAG CCA ACA GTG ACT   2403
Cys Leu Met Ala Leu Lys Val Pro Thr Thr Glu Lys Pro Thr Val Thr
        785             790             795

GTG AAC TTC CGA AAG CTG TTG TTG AAT CGA TGT CAG AAG GAG TTT GAG   2451
Val Asn Phe Arg Lys Leu Leu Leu Asn Arg Cys Gln Lys Glu Phe Glu
    800             805             810

AAA GAC AAA GAT GAT GAT GAG GTT TTT GAG AAG AAG CAA AAA GAG ATG   2499
Lys Asp Lys Asp Asp Asp Glu Val Phe Glu Lys Lys Gln Lys Glu Met
    815             820             825

GAT GAA GCT GCT ACG GCA GAG GAA CGA GGA CGC CTG AAG GAA GAG CTG   2547
Asp Glu Ala Ala Thr Ala Glu Glu Arg Gly Arg Leu Lys Glu Glu Leu
830             835             840             845

GAA GAG GCT CGG GAC ATA GCC CGG CGG CGC TCT TTA GGG AAT ATC AAG   2595
Glu Glu Ala Arg Asp Ile Ala Arg Arg Arg Ser Leu Gly Asn Ile Lys
            850             855             860

TTT ATT GGA GAG TTG TTC AAA CTG AAG ATG TTA ACA GAG GCA ATA ATG   2643
Phe Ile Gly Glu Leu Phe Lys Leu Lys Met Leu Thr Glu Ala Ile Met
        865             870             875
```

FIG. 9D

```
CAT GAC TGT GTG GTC AAA CTG CTT AAG AAC CAT GAT GAA GAG TCC CTT   2691
His Asp Cys Val Val Lys Leu Leu Lys hen His Asp Glu Glu Ser Leu
        880             885                 890

GAG TGC CTT TGT CGT CTG CTC ACC ACC ATT GGC AAA GAC CTG GAC TTT   2739
Glu Cys Leu Cys Arg Leu Leu Thr Thr Ile Gly Lys Asp Leu Asp Phe
    895             900                 905

GAA AAA GCC AAG CCC CGA ATG GAT CAG TAT TTC AAC CAG ATG GAA AAA   2787
Glu Lys Ala Lys Pro Arg Met Asp Gln Tyr Phe Asn Gln Met Glu Lys
910             915                 920                 925

ATC ATT AAA GAA AAG AAG ACG TCA TCC CGC ATC CGC TTT ATG CTG CAG   2835
Ile Ile Lys Glu Lys Lys Thr Ser Ser Arg Ile Arg Phe Met Leu Gln
                930             935                 940

GAC GTG CTG GAT CTG CGA GGG AGC AAT TGG GTG CCA CGC CGA GGG GAT   2883
Asp Val Leu Asp Leu Arg Gly Ser Asn Trp Val Pro Arg Arg Gly Asp
            945             950                 955

CAG GGT CCC AAG ACC ATT GAC CAG ATC CAT AAG GAG GCT GAG ATG GAA   2931
Gln Gly Pro Lys Thr Ile Asp Gln Ile His Lys Glu Ala Glu Met Glu
        960             965                 970

GAA CAT CGA GAG CAC ATC AAA GTG CAG CAG CTC ATG GCC AAG GGC AGT   2979
Glu His Arg Glu His Ile Lys Val Gln Gln Leu Met Ala Lys Gly Ser
975             980                 985

GAC AAG CGT CGG GGC GGT CCT CCA GGC CCT CCC ATC AGC CGT GGA CTT   3027
Asp Lys Arg Arg Gly Gly Pro Pro Gly Pro Pro Ile Ser Arg Gly Leu
990             995             1000                1005

CCC CTT GTG GAT GAT GGT GGC TGG AAC ACA GTT CCC ATC AGC AAA GGT   3075
Pro Leu Val Asp Asp Gly Gly Trp Asn Thr Val Pro Ile Ser Lys Gly
                1010            1015                1020

AGC CGC CCC ATT GAC ACC TCA CGA CTC ACC AAG ATC ACC AAG CCT GGC   3123
Ser Arg Pro Ile Asp Thr Ser Arg Leu Thr Lys Ile Thr Lys Pro Gly
            1025            1030                1035

TCC ATC GAT TCT AAC AAC CAG CTC TTT GCA CCT GGA GGG CGA CTG AGC   3171
Ser Ile Asp Ser Asn Asn Gln Leu Phe Ala Pro Gly Gly Arg Leu Ser
        1040            1045                1050

TGG GGC AAG GGC AGC AGC GGA GGC TCA GGA GCC AAG CCC TCA GAC GCA   3219
Trp Gly Lys Gly Ser Ser Gly Gly Ser Gly Ala Lys Pro Ser Asp Ala
    1055            1060                1065

GCA TCA GAA GCT GCT CGC CCA GCT ACT AGT ACT TTG AAT CGC TTC TCA   3267
Ala Ser Glu Ala Ala Arg Pro Ala Thr Ser Thr Leu Asn Arg Phe Ser
1070            1075                1080                1085

GCC CTT CAA CAA GCG GTA CCC ACA GAA AGC ACA GAT AAT AGA CGT GTG   3315
Ala Leu Gln Gln Ala Val Pro Thr Glu Ser Thr Asp Asn Arg Arg Val
                1090            1095                1100
```

FIG. 9E

```
GTG CAG AGG AGT AGC TTG AGC CGA GAA CGA GGC GAG AAA GCT GGA GAC    3363
Val Gln Arg Ser Ser Leu Ser Arg Glu Arg Gly Glu Lys Ala Gly Asp
        1105            1110            1115
CGA GGA GAC CGC CTA GAG CGG AGT GAA CGG GGA GGG GAC CGT GGG GAC    3411
Arg Gly Asp Arg Leu Glu Arg Ser Glu Arg Gly Gly Asp Arg Gly Asp
        1120            1125            1130
CGG CTT GAT CGT GCG CGG ACA CCT GCT ACC AAG CGG AGC TTC AGC AAG    3459
Arg Leu Asp Arg Ala Arg Thr Pro Ala Thr Lys Arg Ser Phe Ser Lys
        1135            1140            1145
GAA GTG GAG GAG CGG AGT AGA GAA CGG CCC TCC CAG CCT GAG GGG CTG    3507
Glu Val Glu Glu Arg Ser Arg Glu Arg Pro Ser Gln Pro Glu Gly Leu
1150            1155            1160            1165
CGC AAG GCA GCT AGC CTC ACG GAG GAT CGG GAC CGT GGG CGG GAT GCC    3555
Arg Lys Ala Ala Ser Leu Thr Glu Asp Arg Asp Arg Gly Arg Asp Ala
        1170            1175            1180
GTG AAG CGA GAA GCT GCC CTA CCC CCA GTG AGC CCC CTG AAG GCG GCT    3603
Val Lys Arg Glu Ala Ala Leu Pro Pro Val Ser Pro Leu Lys Ala Ala
        1185            1190            1195
CTC TCT GAG GAG GAG TTA GAG AAG AAA TCC AAG GCT ATC ATT GAG GAA    3651
Leu Ser Glu Glu Glu Leu Glu Lys Lys Ser Lys Ala Ile Ile Glu Glu
        1200            1205            1210
TAT CTC CAT CTC AAT GAC ATG AAA GAG GCA GTC CAG TGC GTG CAG GAG    3699
Tyr Leu His Leu Asn Asp Met Lys Glu Ala Val Gln Cys Val Gln Glu
        1215            1220            1225
CTG GCC TCA CCC TCC TTG CTC TTC ATC TTT GTA CGG CAT GGT GTC GAG    3747
Leu Ala Ser Pro Ser Leu Leu Phe Ile Phe Val Arg His Gly Val Glu
1230            1235            1240            1245
TCT ACG CTG GAG CGC AGT GCC ATT GCT CGT GAG CAT ATG GGG CAG CTG    3795
Ser Thr Leu Glu Arg Ser Ala Ile Ala Arg Glu His Met Gly Gln Leu
        1250            1255            1260
CTG CAC CAG CTG CTC TGT GCT GGG CAT CTG TCT ACT GCT CAG TAC TAC    3843
Leu His Gln Leu Leu Cys Ala Gly His Leu Ser Thr Ala Gln Tyr Tyr
        1265            1270            1275
CAA GGG TTG TAT GAA ATC TTG GAA TTG GCT GAG GAC ATG GAA ATT GAC    3891
Gln Gly Leu Tyr Glu Ile Leu Glu Leu Ala Glu Asp Met Glu Ile Asp
        1280            1285            1290
ATC CCC CAC GTG TGG CTC TAC CTA GCG GAA CTG GTA ACA CCC ATT CTG    3939
Ile Pro His Val Trp Leu Tyr Leu Ala Glu Leu Val Thr Pro Ile Leu
        1295            1300            1305
CAG GAA GGT GGG GTG CCC ATG GGG GAG CTG TTC AGG GAG ATT ACA AAG    3987
Gln Glu Gly Gly Val Pro Met Gly Glu Leu Phe Arg Glu Ile Thr Lys
1310            1315            1320            1325
```

FIG. 9F

```
CCT CTG AGA CCG TTG GGC AAA GCT GCT TCC CTG TTG CTG GAG ATC CTG    4035
Pro Leu Arg Pro Leu Gly Lys Ala Ala Ser Leu Leu Leu Glu Ile Leu
            1330            1335                1340

GGC CTC CTG TGC AAA AGC ATG GGT CCT AAA AAG GTG GGG ACG CTG TGG    4083
Gly Leu Leu Cys Lys Ser Met Gly Pro Lys Lys Val Gly Thr Leu Trp
            1345            1350                1355

CGA GAA GCC GGG CTT AGC TGG AAG GAA TTT CTA CCT GAA GGC CAG GAC    4131
Arg Glu Ala Gly Leu Ser Trp Lys Glu Phe Leu Pro Glu Gly Gln Asp
        1360            1365                1370

ATT GGT GCA TTC GTC GCT GAA CAG AAG GTG GAG TAT ACC CTG GGA GAG    4179
Ile Gly Ala Phe Val Ala Glu Gln Lys Val Glu Tyr Thr Leu Gly Glu
        1375            1380                1385

GAG TCG GAA GCC CCT GGC CAG AGG GCA CTC CCC TCC GAG GAG CTG AAC    4227
Glu Ser Glu Ala Pro Gly Gln Arg Ala Leu Pro Ser Glu Glu Leu Asn
1390            1395            1400                1405

AGG CAG CTG GAG AAG CTG CTG AAG GAG GGC AGC AGT AAC CAG CGG GTG    4275
Arg Gln Leu Glu Lys Leu Leu Lys Glu Gly Ser Ser Asn Gln Arg Val
            1410            1415                1420

TTC GAC TGG ATA GAG GCC AAC CTG AGT GAG CAG CAG ATA GTA TCC AAC    4323
Phe Asp Trp Ile Glu Ala Asn Leu Ser Glu Gln Gln Ile Val Ser Asn
            1425            1430                1435

ACG TTA GTT CGA GCC CTC ATG ACG GCT GTC TGC TAT TCT GCA ATT ATT    4371
Thr Leu Val Arg Ala Leu Met Thr Ala Val Cys Tyr Ser Ala Ile Ile
            1440            1445                1450

TTT GAG ACT CCC CTC CGA GTG GAC GTT GCA GTG CTG AAA GCG CGA GCG    4419
Phe Glu Thr Pro Leu Arg Val Asp Val Ala Val Leu Lys Ala Arg Ala
        1455            1460                1465

AAG CTG CTG CAG AAA TAC CTG TGT GAC GAG CAG AAG GAG CTA CAG GCG    4467
Lys Leu Leu Gln Lys Tyr Leu Cys Asp Glu Gln Lys Glu Leu Gln Ala
1470            1475                1480            1485

CTC TAC GCC CTC CAG GCC CTT GTA GTG ACC TTA GAA CAG CCT CCC AAC    4515
Leu Tyr Ala Leu Gln Ala Leu Val Val Thr Leu Glu Gln Pro Pro Asn
        1490            1495                1500

CTG CTG CGG ATG TTC TTT GAC GCA CTG TAT GAC GAG GAC GTG GTG AAG    4563
Leu Leu Arg Met Phe Phe Asp Ala Leu Tyr Asp Glu Asp Val Val Lys
            1505            1510                1515

GAG GAT GCC TTC TAC AGT TGG GAG AGT AGC AAG GAC CCC GCT GAG CAG    4611
Glu Asp Ala Phe Tyr Ser Trp Glu Ser Ser Lys Asp Pro Ala Glu Gln
            1520            1525                1530

CAG GGC AAG GGT GTG GCC CTT AAA TCT GTC ACA GCC TTC TTC AAG TGG    4659
Gln Gly Lys Gly Val Ala Leu Lys Ser Val Thr Ala Phe Phe Lys Trp
        1535            1540                1545
```

FIG. 9G

```
CTC CGT GAA GCA GAG GAG GAG TCT GAC CAC AAC TGAGGGCTGG TGGGGCCGGG   4712
Leu Arg Glu Ala Glu Glu Glu Ser Asp His Asn
1550            1555                1560

GACCTGGAGC CCCATGGACA CACAGATGGC CCGGCTAGCC GCCTGGACTG CAGGGGGGCG   4772
GCAGCAGCGG CGGTGGCAGT GGGTGCCTGT AGTGTGATGT GTCTGAACTA ATAAAGTGGC   4832
TGAAGAGGCA GGATGGCTTG GGGCTGCCTG GGCCCCCCTC CAGGATGCCG CCAGGTGTCC   4892
CTCTCCTCCC CCTGGGGCAC AGAGATATAT TATATATAAA GTCTTGAAAT TTGGTGTGTC   4952
TTGGGGTGGG GAGGGGCACC AACGCCTGCC CCTGGGGTCC TTTTTTTTAT TTTCTGAAAA   5012
TCACTCTCGG GACTGCCGTC CTCGCTGCTG GGGGCATATG CCCCAGCCCC TGTACCACCC   5072
CTGCTGTTGC CTGGGCAGGG GGAAGGGGGG GCACGGTGCC TGTAATTATT AAACAT       5128
```

FIG. 9H

TRANSLATION DRIVER SYSTEM AND METHODS FOR USE THEREOF

1. INTRODUCTION

The present method relates to the translational activation of genes using the ribosome recruitment protein, eIF4G or an eIF4G-like protein. The invention relates to the translation of RNA molecules containing heterologous protein-binding sites, which RNA molecules encode one, two, three or more proteins. The invention provides products and methods for the identification of RNA-binding proteins. The invention further provides a system by which protein—protein interactions and inhibitors or enhancers of these interactions may be identified. Further, the invention provides products and methods to provide a cell with one or more therapeutic proteins. The invention provides products and methods for controlling the levels of translation of such proteins. The invention provides products and methods to control the translation and stoichiometry of multiple subunit proteins. The invention provides products for and methods of screening for proteins which interact with an RNA binding site, and methods for identifying RNA binding sites.

2. BACKGROUND OF THE INVENTION

Citation of a reference herein shall not be construed as an admission that such is prior art to the present invention.

2.1. PROTEIN—PROTEIN INTERACTIONS BY TRANSCRIPTIONAL SYSTEMS

Proteins and protein—protein interactions play a central role in the various essential biochemical processes. For example, these interactions are evident in the interaction of hormones with their respective receptors, in the intracellular and extracellular signaling events mediated by proteins, in enzyme substrate interactions, in intracellular protein trafficking, in the formation of complex structures like ribosomes, viral coat proteins, and filaments, and in antigen-antibody interactions. These interactions are usually facilitated by the interaction of small regions within the proteins that can fold independently of the rest of the protein. These independent units are called protein domains. Abnormal or disease states can be the direct result of aberrant protein—protein interactions. For example, oncoproteins can cause cancer by interacting with and activating proteins responsible for cell division. Protein-protein interactions are also central to the mechanism of a virus recognizing its receptor on the cell surface as a prelude to infection protein—protein interactions direct signal transduction cascades that result in a biological response. Identification of domains that interact with each other not only leads to a broader understanding of protein—protein interactions, but also aids in the design of inhibitors of these interactions.

Protein-protein interactions have been studied by both biochemical and genetic methods. The biochemical methods are laborious and slow, often involving painstaking isolation, purification, sequencing and further biochemical characterization of the proteins being tested for interaction. As an alternative to the biochemical approaches, genetic approaches to detect protein—protein interactions have gained in popularity as these methods allow the rapid detection of the domains involved in protein—protein interactions.

An example of a genetic system to detect protein—protein interactions is the "Two-Hybrid" system to detect protein—protein interactions in the yeast *Saccharomyces cerevisiae* (Fields and Song, 1989, Nature 340:245–246; U.S. Pat. No. 5,283,173 by Fields and Song). This assay utilizes the reconstitution of a transcriptional activator like GAL4 (Johnston, 1987, Microbiol. Rev. 51:458–476) through the interaction of two protein domains that have been fused to the two functional units of the transcriptional activator: the DNA-binding domain and the activation domain. This is possible due to the bipartite nature of certain transcription factors like GAL4. Being characterized as bipartite signifies that the DNA-binding and activation functions reside in separate domains and can function in trans (Keegan et al., 1986, Science 231:699–704). The reconstitution of the transcriptional activator is monitored by the activation of a reporter gene such as the lacZ gene that is under the influence of a promoter that contains a binding site (Upstream Activating Sequence or UAS) for the DNA-binding domain of the transcriptional activator. This method is most commonly used either to detect an interaction between two known proteins (Fields and Song, 1989, Nature 340:245–246) or to identify interacting proteins from a population that would bind to a known protein (Durfee et al., 1993, Genes Dev. 7:555–569; Gyuris et al., 1993, Cell 75:791–803; Harper et al., 1993, Cell 75:805–816; Vojtek et al., 1993, Cell 74:205–214).

Another system that is similar to the Two-Hybrid system is the "Interaction-Trap system" devised by Brent and colleagues (Gyuris et al., 1993, Cell 75:791–803). This system is similar to the Two-Hybrid system except that it uses a LEU2 reporter gene and a lacZ reporter gene. Thus protein—protein interactions also lead to the reconstitution of the transcriptional activator system and allows cells to grow in media lacking leucine and enable them to express β-galactosidase. The DNA-binding domain used in this system is the LexA DNA-binding domain, while the activator sequence is obtained from the B42 transcriptional activation domain (Ma and Ptashne, 1987, Cell 51:113–119). The promoters of the reporter genes contain LexA binding sequences and hence will be activated by the reconstitution of the transcriptional activator. Another feature of this system is that the gene encoding the DNA-binding domain fusion protein is under the influence of an inducible GAL promoter so that confirmatory tests can be performed under inducing and non-inducing conditions.

Still other versions of the two-hybrid approach exist, for example, a "Contingent Replication Assay" has been reported (Nallur et al., 1993, Nucleic Acids Res. 21:3867–3873; Vasavada et al., 1991, Proc. Natl. Acad. Sci. USA 88:10686–10690). In this case, the reconstitution of the transcription factor in mammalian cells due to the interaction of the two fusion proteins leads to the activation of transcription of the SV40 T antigen. This antigen allows the replication of the activation domain fusion plasmids. Another modification of the two-hybrid approach using mammalian cells is the "Karyoplasmic Interaction Selection Strategy" that also uses the reconstitution of a transcriptional activator (Fearon et al., 1992, Proc. Natl. Acad. Sci. USA 89:7958–7962). Reporter genes used in this case have included the gene encoding the bacterial chloramphenicol acetyl transferase, the gene for cell-surface antigen CD4, and the gene encoding resistance to Hygromycin B. In both of the mammalian systems, the transcription factor that is reconstituted is a hybrid transcriptional activator in which the DNA-binding domain is from GAL4 and the activation domain is from VP16.

Recently, a transcriptional activation system has been described to isolate and catalog possible protein—protein interactions within a population, and allow the comparison of such interactions between two populations (see PCT Publication WO 97/47763 published Dec. 18, 1997).

However, all of the assays mentioned above utilize a transcriptional activation system which examines the interaction of DNA binding proteins with DNA of a reporter gene. Additionally, the transcriptional systems require that proteins being assayed be driven into the nucleus. Accordingly, there is a need in the art for a system which allows for detecting protein—protein interactions and inhibitors or enhancers of such interactions in the cytoplasmic compartment of a cell. The present invention provides such a system.

Additionally, none of the systems described above provide a means by which a protein important for the translational-activation of a gene may be identified. Nor do any of the methods described above provide a method for activating the translation of a gene-of-interest. The present invention provides such methods and compositions as well as therapeutic, diagnostic, and analytical uses of such methods and compositions.

2.2. TRANSLATION IN PROCARYOTES AND EUCARYOTES

Procaryotic and eucaryotic cells use different strategies to specify the translation start site on an mRNA molecule. In bacterial mRNAs a conserved stretch of six nucleotides, called the Shine-Dalgarno sequence, is located a few nucleotides upstream from the initiating AUG codon. This sequence pairs with the 16S RNA in the small ribosomal subunit and thereby correctly positions the initiating AUG codon in the ribosome. This interaction controls the efficiency of initiation of translation in bacteria, and many of the translational control systems in procaryotes involve blocking the Shine-Dalgarno sequence by covering the sequence with a protein or by incorporating it into a base-paired region in the mRNA molecule.

In contrast, eucaryotic mRNAs do not contain a Shine-Dalgarno sequence. In eucaryotes, the selection of an AUG as a translational start site has been thought to be determined by the proximity of the AUG to the cap at the 5' end of the mRNA molecule, where the small ribosomal subunit binds to the mRNA and begins scanning for an initiating AUG codon (In Molecular Biology of the Cell, 3d ed., 1994, Alberts, B. et al. pp. 461–468). If the recognition of the AUG codon is poor, the scanning ribosomal subunits will ignore the first AUG in the mRNA and skip to the second or third AUG codon, Id at 461. The result of this "leaky scanning" process is to produce two or more proteins from the same mRNA that differ in their amino termini. However, a majority of eucaryotic genes begin translation at the first AUG codon, Id. at 461.

Another significant difference between procaryotic and eucaryotic translation is that the eucaryotic ribosomes dissociate rapidly from mRNA when translation terminates, Id. at 462. Accordingly, reinitiation at an internal AUG codon is less efficient in eucaryotes than procaryotes. This difference serves to explain why a majority of eucaryotic mRNAs encode only a single protein that is translated from the first AUG from the 5' end of the mRNA molecule, Id. at 462.

Some eucaryotic cell and viral mRNAs can initiate translation by an alternative mechanism that involves internal initiation rather than scanning. These mRNAs contain complex nucleic acid sequences called internal ribosome entry sites (IRES) Id. at 462. IRES bind ribosomes in a cap independent manner (see. Section 2.3), and translations begins at an AUG codon that is 3' to the entry site.

2.3. DEPENDENCE OF INITIATION OF TRANSLATION ON THE PRE-INITIATION COMPLEX

Translation of most eukaryotic mRNAs requires a 5' cap structure ($m^7GpppN$) and 3' poly(A) tail (Gallie, D., 1991, *Genes & Dev.* 5:2108–2116). These structures promote translation initiation by binding to the eukaryotic translation initiation factor (eIF4E) and the poly(A)-binding protein (PABP), respectively. The protein eIF4G forms a molecular bridge between eIF4E (Mader, et al., 1995, *Mol. Cell. Biol.* 15:4990–4997) and PABP (Tarun, et al., 1996, *EMBO J.* 15:7168–7177, Imataka, et al., 1998, *EMBO J.* 17:7480–7489). Binding of eIF4G leads to a circularizing of the mRNA (Wells, et al., 1998, *Mol. Cell* 2:135–40). eIF4G also binds the 40S ribosomal subunit via eIF3 (Lamphear, et al., 1995, *J. Biol. Chem.* 270:21975–21983).

The binding of the small ribosomal subunit as part of the 43S translation pre-initiation complex represents a rate-limiting step in mRNA translation (Sachs, et al., 1997, *Cell* 89:831–838). The 5' cap structure and the 3' poly(A) tail with their respective binding proteins have been shown to play critical roles (Gallie, D., 1991, Genes & Dev. 5:2108–2116, Tarun, et al., 1996, *EMBO J.* 15:7168–7177; Preiss, T., et al., 1998, *Nature* 392:516–520). The function of eIF4G in ribosome recruitment is less clearly defined (Hentze, et al., 1997, *Science* 275:500–501). eIF4G is a subunit of the cap binding complex, which complex also includes eIF4F and the cap recognition factor eIF4E and, in higher eukaryotes, the RNA-dependent ATPase eIF4A (FIG. 1a, upper scheme). Stimulated by eIF4B, eIF4A is thought to unwind secondary structure in the 5' UTR of the mRNA. eIF4G has a modular structure (see FIG. 3a). It interacts with eIF4E (Mader, et al., 1995, *Mol. Cell. Biol.* 15:4990–4997) and PABP (Imataka, et al., 1998, *EMBO J.* 17:7480–7489). The central region bears a putative RNA recognition motif (RRM) (Goyer, C. et al., 1993, *Mol. Cell. Biol.* 13:4860–4874, De Gregorio, et al., 1998, *RNA* 4:828–36) and binding sites for eIF4A (Imataka, et al., 1997, *Mol. Cell. Biol.* 17:6940–6947) and eIF3 (Lamphear, et al. 1995, *J. Biol. Chem.* 270:21975–21983). The C-terminal harbors a second binding site for eIF4A (Lamphear, et al., 1995, *J. Biol. Chem.* 270:21975–21983) and for the eIF4E kinase Mnk1 (Pyronnet, S. et al., 1999, *EMBO J.* 13:270–279).

3. SUMMARY OF THE INVENTION

As described herein, the inventors of the present invention have made the surprising discovery that a core region of human eIF4G1 (in the example, amino acids 642–1091), lacking both the eIF4E- and PABP-binding sites functions as an autonomous ribosome recruitment core in vivo. Further the inventors demonstrate that fusion of this region of eIF4G1 to the IRE-binding protein IRP-1 suffices to direct the translation of downstream cistron of bicistronic or multi-cistronic mRNAs bearing IREs in their intercistronic space. This function of translational activation is preserved even when translation via the 5' end is inhibited. Thus, eIF4G-like proteins (including but not limited to mammalian eIF4G1) have been discovered to represent the critical ribosome recruitment factor sufficient to drive downstream translation in vivo.

Accordingly, the present invention provides methods and means to detect and isolate the genes encoding RNA-binding proteins. The invention provides methods for detecting binding sites in an RNA molecule for such proteins. The methods of the invention provide the reconstitution of a selectable event, which is the formation of a translation factor. In one embodiment, the reconstitution of a translation factor occurs by interaction of fusion proteins expressed by chimeric genes. In a preferred embodiment, the type of fusion protein used is an RNA-binding protein fused to eIF4G-like protein or a translationally active derivative of an eIF4G-like protein. In another embodiment, RNA-binding proteins are found by fusing eIF4G-like protein or a translationally active derivative of eIF4G-like protein to a cDNA library. In a highly preferred embodiment, the fusion protein (s) drives translation of one, or more open reading frames from a downstream coding region of a bi-cistronic mRNA. In a most preferred embodiment, the fusion protein(s) of the invention drives the translation of several (e.g., two, three, four, five, six, seven, or more, etc.) open reading frames from a multi-cistronic mRNA. In a further embodiment, the level of translation (e.g., the amount of protein translated from each AUG start sites of a multi-cistronic RNA) is controlled by the use of protein-binding sites in the RNA (e.g., a heterologous protein-binding site (HBS)). In a further embodiment, the level of translation of each cistron is controlled by the use of different protein-binding sites in the RNA (e.g., different HBSs). In another embodiment, the level of translation is controlled by the number of HBSs that are placed intercistronically. In yet another embodiment, the level of translation is controlled by the proximity of an HBS to an adjacent and downstream cistron (e.g., the distance in nucleotides between the HBS and the cistron).

In yet another use of the invention, the reconstitution of a translational activator leads to the translation of a reporter protein which can be used to determine protein—protein interactions. Not by way of limitation, the translational activator is reconstituted due to the proximity of the RNA-binding protein and the ribosome recruitment core (e.g., translationally active) of an eIF4G-like protein via the interaction of two test proteins. This reconstitution causes translation of reporter genes or downstream cistron(s) that, by way of example, contain a label or enable cells to grow in selective media. In a preferred aspect, the activity of a reporter gene is monitored enzymatically. The isolation of the plasmids that encode these fusion genes containing test proteins leads to the identification of the genes that encode proteins that interact with each other. In a specific embodiment, one of the test proteins of a protein—protein interaction is known. In another embodiment, neither of the test proteins are known. In a further embodiment of the invention, inhibitors of a protein—protein interaction are identified, by the lack of or decrease in translation of a reporter protein relative to that observed in the absence of the candidate inhibitor. In another embodiment, enhancers or facilitators of a protein—protein interaction are identified, by the increase in translation of a reporter protein relative to that observed in the absence of the candidate facilitator.

Accordingly, this invention provides genetic and biochemical methods to identify and isolate proteins which interact. The invention also provides methods to identify proteins which bind to RNA. The present invention provides methods to identify RNA sequences to which an RNA-binding protein interacts.

The invention also provides methods to identify and isolate in a rapid manner the genes encoding the proteins involved in interactions that are specific to translational control of a gene. This invention provides methods for the identification of protein—protein interactions that characterize a given population. This invention provides methods for the concurrent identification of inhibitors of the protein—protein interactions. The invention further provides methods for controlling stoichiometry of multi-subunit proteins, and methods to produce one or more protein(s) in a host cell.

The invention relates to nucleic acids encoding a RNA comprising one or more heterologous protein-binding sites (e.g., HBS) and one or more genes. The invention also relates to recombinant cells containing a nucleotide sequence encoding a RNA containing a HBS. The invention further relates to nucleic acids encoding an eIF4G-like protein or derivatives or fragments thereof fused to a RNA-binding protein. The invention also relates to nucleic acids encoding an RNA-binding protein or derivatives fused to a first test protein, and an eIF4G-like protein fused to a second test protein and methods for reconstituting a translational activator.

The invention provides a nucleic acid encoding an RNA, said RNA comprising a coding region with one or more heterologous protein-binding sites in a non-coding region 5' and adjacent to the coding region. In one embodiment the DNA molecule is purified. In another embodiment, the binding site is selected from the group consisting of IRE, MS2 RNA replicase site, U1A snRNA site, and λ box B site.

The invention provides a DNA molecule comprising a promoter operably linked to a nucleotide sequence, which nucleotide sequence is transcribed in an appropriate cell to produce an RNA, said RNA comprising one or more coding regions, each with one or more heterologous protein-binding sites in a non-coding region 5' and adjacent to the coding region. In one embodiment the RNA comprises two or more coding regions, and wherein a heterologous protein-binding site is in an intercistronic region. In one embodiment, at least one downstream coding region that is 3' to another coding region is a reporter gene coding region. In another embodiment, at least one downstream coding region that is 3' to another coding region encodes a Therapeutic. In yet another embodiment, at least two coding regions (a) are 3' to another coding region, and (b) each encodes a different subunit of a multi-subunit protein. In another embodiment, the DNA molecule has two or more heterologous protein-binding sites in at least one intercistronic region. In yet another embodiment, the promoter is inducible.

In one embodiment, the invention provides expression vector comprising the DNA molecule comprising a promoter operably linked to a nucleotide sequence, which nucleotide sequence is transcribed in an appropriate cell to produce an RNA, said RNA comprising one or more coding regions, each with one or more heterologous protein-binding sites in a non-coding region 5' and adjacent to the coding region; and an origin of replication. In one embodiment the expression vector is a plasmid.

The invention provides an RNA molecule comprising a coding region with a heterologous protein-binding site in a non-coding region 5' and adjacent to the coding region. In one embodiment the RNA comprises two or more coding regions, and wherein a heterologous protein-binding site is in an intercistronic region. In another embodiment, the RNA molecule is purified.

The invention provides fusion protein comprising an RNA-binding protein fused to an eIF4G-like protein or a translationally active derivative thereof. In one embodiment the RNA-binding protein is fused to a translationally active derivative of a eIF4G-like protein. In a further embodiment, the translationally active derivative comprises an eIF3 binding domain of eIF4G1. In another embodiment, the translationally active derivative lacks one or more of the PABP domain and the eIF4E binding domain. The invention provides nucleotide sequence encoding the fusion protein, and expression vectors comprising such sequence.

The invention provides a fusion protein comprising an eIF4G-like protein or translationally active derivative thereof fused to a second, different protein. In one embodiment the translationally active derivative of the eIF4G-like protein is fused to the second protein. In another embodiment the the translationally active derivative comprises an eIF3 binding domain of eIF4G1. In yet another embodiment, the translationally active derivative lacks one or more of the PABP domain and the eIF4E binding domain. The invention provides nucleotide sequence encoding the fusion protein, and expression vectors comprising such sequence.

The invention provides a fusion protein comprising an RNA-binding protein fused to a second, different protein. In one embodiment the RNA-binding protein is selected from the group consisting of IRP- 1, bacteriophage MS2 coat protein, spliceosomal protein U1A, and λ box B binding protein. The invention provides nucleotide sequence encoding the fusion protein, and expression vectors comprising such sequence.

The invention provides a population of nucleic acids, wherein each nucleic acid in the population is a vector comprising (a) an origin of replication; (b) a nucleotide sequence encoding the fusion comprising an eIF4G-like protein or translationally active derivative thereof fused to a second, different protein; and (c) a promoter operably linked to said nucleotide sequence; wherein the identity of said second, different protein varies among said population. In one embodiment the population has a complexity of at least 100. In another embodiment the nucleotide sequences are those of a cDNA library. In another embodiment, the nucleotide sequences are of a random or biased peptide expression library.

The invention provides a population of nucleic acids, wherein each nucleic acid in the population is a vector comprising (a) an origin of replication; (b) a nucleotide sequence encoding the fusion comprising an RNA-binding protein fused to a second, different protein; and (c) a promoter operably linked to said nucleotide sequence; wherein the identity of said second, different protein varies among said population. In one embodiment the population has a complexity of at least 100. In another embodiment the nucleotide sequences are those of a cDNA library. In another embodiment, the nucleotide sequences are of a random or biased peptide expression library. The invention provides recombinant cells comprising the above nucleic acid. The invention provides transgenic organisms comprising as a transgene the above nucleic acids.

The invention provides a population of recombinant cells comprising the population of nucleic acids described above.

The invention provides methods of producing the above fusion proteins comprising subjecting a recombinant cell comprising the above nucleic acid to conditions such that the nucleotide sequence is expressed by the cell.

The invention provides kits comprising in one or more containers the nucleic acid the above-described nucleic acids.

The invention provides a nucleic acid comprising (a) a nucleotide sequence encoding an eIF4G-like protein or a translationally active derivative thereof; and (b) a polylinker region 5' or 3' to said nucleotide sequence that allows for insertion after restriction enzyme digestion of a nucleic acid fragment in the correct reading frame so as to encode a fusion protein to the eIF4G-like protein or derivative.

The invention provides a nucleic acid comprising (a) a nucleotide sequence encoding an RNA-binding protein; and (b) a polylinker region 5' or 3' to said nucleotide sequence that allows for insertion after restriction enzyme digestion of a nucleic acid fragment in the correct reading frame so as to encode a fusion protein to the RNA-binding protein.

The invention provides a method of producing a protein comprising contacting within a eukaryotic cell: (a) an RNA molecule comprising (i) a coding region encoding said protein, and (ii) a protein-binding site in a noncoding region 5' and adjacent to said coding region; and (b) a fusion protein comprising (i) an RNA-binding protein that binds to said protein-binding site, fused to an eIF4G-like protein or a translationally active derivative thereof. In one embodiment the RNA molecule comprises two or more coding regions, and wherein a heterologous protein-binding site is in an intercistronic region, or has two or more heterologous protein-binding sites in at least one intercistronic region. In another embodiment at least two coding regions (a) are 3' to another coding region, and (b) each encodes a different subunit of a multi-subunit protein.

The invention provides a method of producing a protein comprising recombinantly expressing a fusion protein within a eukaryotic cell, wherein the cell contains a DNA molecule that is transcribed within the cell to produce a monocistronic or multicistronic RNA containing a heterologous protein-binding site in a region 5' and adjacent to a coding region encoding said protein; wherein the fusion protein comprises (i) an RNA-binding protein that binds to said protein-binding site, fused to an eIF4G-like protein or a translationally active derivative thereof. In one embodiment the DNA molecule is a plasmid expression vector. In one embodiment the plasmid comprises an inducible promoter controlling production of said RNA. In another embodiment the fusion protein is expressed from a plasmid expression vector comprising a promoter operably linked to a nucleotide sequence encoding said fusion protein. In yet another embodiment the two or more identical heterologous protein-binding sites are in said intercistronic region. In still another embodiment, two or more intercistronic regions contain the heterologous protein-binding site, each of said two or more intercistronic regions encoding a different subunit of a multi-subunit protein.

The invention provides a method for detecting an RNA-binding protein comprising: (a) recombinantly expressing in a eukaryotic cell a fusion protein comprising an eIF4G-like protein or a translationally active derivative thereof fused to a test protein, wherein the cell comprises a DNA that is transcribed to produce a monocistronic or multicistronic RNA containing a heterologous protein-binding site in a region 5' and adjacent to a reporter gene coding region; and (b) detecting an increase in the amount of the protein encoded by said reporter gene coding sequence, relative to said amount produced in the absence of said test protein, wherein an increase in said amount indicates that the test protein is an RNA-binding protein that binds to said heterologous protein-binding site. In one embodiment the two or more identical heterologous protein-binding sites are in said intercistronic region.

The invention provides a method for detecting a protein-binding site in an RNA comprising: (a) recombinantly producing in a eukaryotic cell: (i) a fusion protein comprising an eIF4G-like protein or a translationally active derivative thereof fused to a first protein for which it is desired to identify an RNA site to which said protein binds; (ii) a monocistronic or multicistronic RNA containing a heterologous test RNA sequence in a region 5' and adjacent to a reporter gene coding region; and (b) detecting an increase in the amount of the protein encoded by said reporter gene coding sequence relative to said amount produced in the absence of said RNA sequence, wherein an increase in said amount indicates that the test RNA sequence is a protein-binding site that binds to said first protein. In one embodiment said fusion protein is expressed from an expression vector.

A method for detecting an RNA binding protein comprising: (a) recombinantly expressing within a population of eukaryotic cells a population of fusion proteins, each fusion protein comprising an eIF4G-like protein or a translationally active derivative thereof fused to a test protein, wherein the test protein varies among said population, wherein the cells comprise a DNA that is transcribed to produce a monocistronic or multicistronic RNA containing a heterologous protein-binding site in a region 5' and adjacent to a reporter gene coding region; and (b) identifying a cell within said population that displays an increase in the amount of the protein encoded by said reporter gene relative to said amount produced in the absence of said test protein or in the presence of other fusion proteins, thereby identifying a cell in which the test protein is an RNA-binding protein that binds to said heterologous protein-binding site. In one embodiment the test protein portion of said fusion proteins are encoded by nucleotide sequences of a cDNA library. In another embodiment the fusion proteins are produced from plasmid expression vectors under the control of an inducible promoter.

The invention provides a method for detecting binding between a first test protein and a second test protein comprising: (a) recombinantly expressing in a eukaryotic cell (a) a first fusion protein comprising an eIF4G-like protein or a translationally active derivative thereof, fused to a first test protein; and (ii) a second fusion protein comprising an RNA-binding protein fused to a second test protein; wherein the cell comprises a DNA that is transcribed to produce a monocistronic or multicistronic RNA containing a heterologous protein-binding site in a region 5' and adjacent to a reporting gene coding region, wherein said RNA-binding protein binds to said heterologous protein-binding site; and (b) detecting an increase in the amount of the protein encoded by said reporter gene coding region relative to said amount produced in the absence of one or both test proteins, wherein an increase in said amount indicates that the first test protein binds to said second test protein.

The invention provides a method for identifying a molecule that affects the amount of binding between a first protein and a second protein comprising: (a) recombinantly expressing in a eukaryotic cell in the presence of a candidate molecule (i) a first fusion protein comprising an eIF4G-like protein or a translationally active derivative thereof, fused to a first protein; and (ii) a second fusion protein comprising an RNA-binding protein fused to a second protein, wherein the first and second proteins bind to each other; wherein the cell comprises a DNA that is transcribed to produce a monocistronic or multicistronic RNA containing a heterologous protein-binding site in a region 5' and adjacent to a reporter gene coding region, and wherein said RNA-binding protein binds to said heterologous protein-binding site; and (b) detecting an increase or decrease in the amount of the protein encoded by said reporter gene coding region relative to said amount produced in the absence of the candidate molecule, wherein said increase or decrease indicates that the candidate molecule inhibits or increases binding of said first protein to said second protein. In a specific embodiment, the candidate molecule is also recombinantly expressed in the cell.

The invention provides a method for identifying a molecule that complexes together a first protein and a second protein comprising: (a) recombinantly expressing in a eukaryotic cell in the presence of a candidate molecule (i) a first fusion protein comprising an eIF4G-like protein or a translationally active derivative thereof, fused to a first protein; and (ii) a second fusion protein comprising an RNA-binding protein, fused to a second protein, wherein the first and second proteins do not bind to each other; wherein the cell comprises a DNA that is transcribed to produce a monocistronic or multicistronic RNA containing a heterologous protein-binding site in a region 5' and adjacent to a reporter gene coding region, wherein said RNA-binding protein binds to said heterologous protein-binding site; and (b) detecting an increase in the amount of the protein encoded by said reporter gene coding region relative to said amount produced in the absence of said candidate molecule, wherein said increase indicates that the candidate molecule complexes together said first protein and said second protein. In a specific embodiment, the candidate molecule is also recombinantly expressed in the cell. In one embodiment the candidate molecule is a candidate inhibitor molecule, and a decrease is detected in step (b), thereby indicating that the candidate molecule inhibits the binding of said first protein to said second protein. In another embodiment an increase is detected in step (b), thereby indicating that the candidate molecule increases the binding of said first protein to said second protein. In another embodiment step (a) comprises recombinantly expressing in a population of said cells a population of said first fusion proteins, wherein said first test protein varies among said population. In a further embodiment, said first test protein portions of said first fusion proteins are encoded by nucleotide sequences of a cDNA library. In another embodiment, step (a) comprises recombinantly expressing in a population of said cells a population of said second fusion proteins, wherein said second test protein varies among said population. In a further embodiment, said second test protein portions of said second fusion proteins are encoded by nucleotide sequences of a cDNA library. In still other embodiments step (a) comprises recombinantly expressing in a population of said cells a plurality of different said candidate molecules. In a further embodiment the method comprises isolating a nucleic acid encoding said first test protein from a cell in which said increase is detected in step (b).

A method of detecting one or more protein—protein binding interactions comprising: (a) recombinantly expressing within a population of eukaryotic cells (i) first population of first fusion proteins comprising an eIF4G-like protein or a translationally active derivative thereof fused to a first test protein, wherein the first test protein varies among the population, (ii) a second population of second fusion proteins comprising an RNA-binding protein fused to a second test protein, wherein the second test protein varies among the population; wherein the cell comprises a DNA that is transcribed to produce a monocistronic or multicistronic RNA containing a heterologous protein-binding site in a region 5' and adjacent to a reporter gene coding region, wherein said RNA-binding protein binds to said heterologous protein-binding site; and (b) detecting a cell that exhibits an increase in the amount of the protein encoded by said reporter gene coding region relative to said amount produced in the absence of one or both test proteins or relative to other cells in the population, wherein said increase indicates that the first and second test proteins in said cell bind to each other.

The invention provides a purified translationally active derivative of an eIF4G-like protein.

The invention provides populations of cells comprising a DNA molecule or a nucleic acid of described above.

The invention provides a pharmaceutical compositions comprising the DNA molecule or a nucleic acids described above in a pharmaceutically acceptable carrier.

The invention provides a method of treating a subject having a disease or disorder amenable to treatment by a protein comprising producing a therapeutically effective amount of said protein in said organism by a method comprising introducing into said subject: (a) a DNA molecule that is transcribed within the subject to produce a monocistronic or multicistronic RNA containing a heterologous protein-binding site in a region 5' and adjacent to a coding region encoding said protein; and (b) a DNA molecule encoding a fusion protein such that the DNA molecule is expressed within the subject to produce said fusion protein, said fusion protein comprising an RNA-binding protein that binds to said heterologous protein-binding site, fused to an eIF4G-like protein or a translationally active derivative thereof. In one embodiment the fusion protein is expressed in the subject under control of an inducible promoter.

The invention provides a method of treating a subject having a disease or disorder amenable to treatment by a protein comprising (a) introducing into the subject: (i) a DNA molecule that is transcribed within the subject to produce a monocistronic or multicistronic RNA containing a heterologous protein-binding site in a region 5' and adjacent to a coding region encoding said protein; and (ii) a DNA molecule encoding a fusion protein such that the DNA molecule is expressed within the subject to produce said fusion protein, said fusion protein comprising an RNA-binding protein that binds to said heterologous protein-binding site, fused to an eIF4G-like protein or a translationally active derivative thereof: and (b) administering the cell to the subject. In one embodiment the cell is a stem or progenitor cell.

4. DESCRIPTION OF THE FIGURES

Figure 1B:
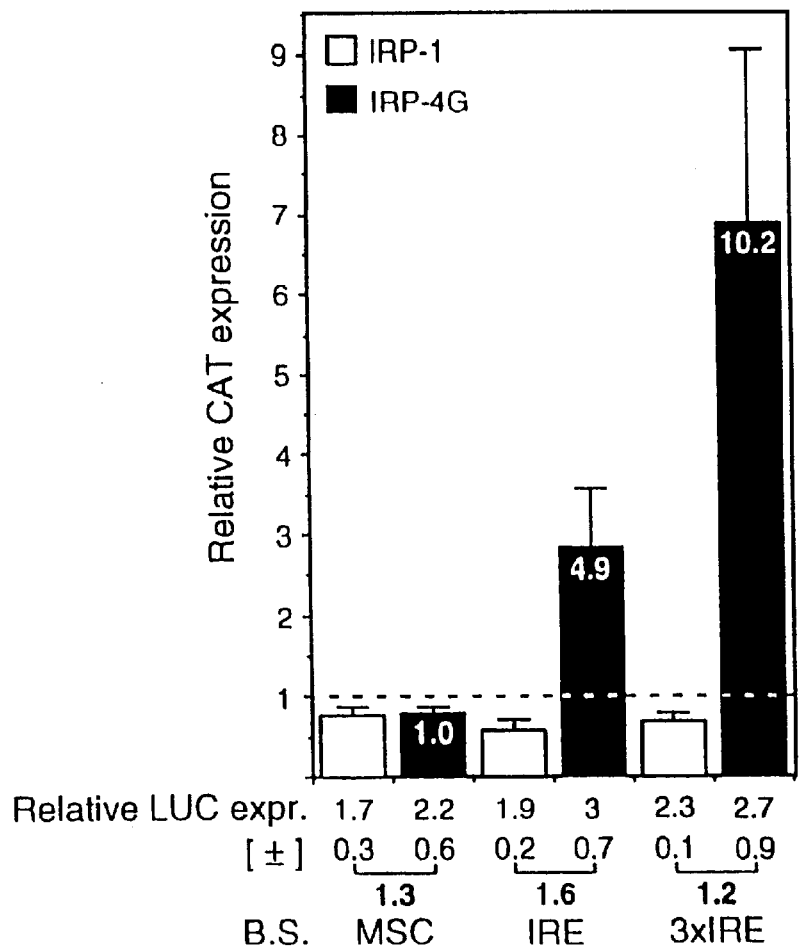

FIGS. 1a–b. IRP-eIF4G1 fusion protein (IRP-4G) activates the translation of a downstream cistron in a binding-site-specific manner. FIG. 1a) Schematic representation of cap-dependent recruitment of the small ribosomal subunit (upper panel) and of the experimental strategy adopted in this work (lower panel). FIG. 1b) HeLa cells were transfected with combinations of three plasmids as follows: MSC (bacteriophage MS2 coat protein used as a negative control), IRE (iron responsive element), or 3×IRE (a multimer of three iron responsive elements). See FIG. 2 for intercistronic structure. Each reporter plasmid was tested with the effector plasmids pSGIRP (white bars), pSGIRP-4G (black bars), or the "empty vector" pSG5 (set to 1 as a reference point, dashed line). In all cases, a plasmid expressing β-Gal (pCMVβ) was cotransfected to correct for transfection efficiency. Each bar represents multiple (3–8) repeated experiments and indicates CAT expression with standard deviation relative to the corresponding control transfection using pSG5. In addition, the specific translational nactivation of CAT by appending eIF4G1 sequences to IRP-1 is indicated for each reporter construct as the ratio between the expression observed with pSGIRP-4G versus pSGIRP cotransfection (white numbers inside the bars). LUC expression data were treated in completely analogous fashion and are indicated below the corresponding bars (translational activation indicated in bold).

FIGS. 2a–b. Role of position and number of RNA binding sites. Transfection experiments were performed as in FIG. 1, using IRE-derived (FIG. 2a) or 3×IRE-derived (FIG. 2b) reporter constructs. Upper panels depict a schematic representation of intercistronic regions. See FIG. 8 for sequences in combination with pSGIRP-4G (black bars) or pSG5 (dashed line). FIG. 2a) The position of the single IRE relative to both cistrons is changed by an upstream insertion of 66 nt (66-IRE) or a downstream deletion of 33 nt (IREΔ33). The results for IRE and MSC are shown as positive and negative controls. FIG. 2b) The 3×IRE construct and variants carrying the ΔC mutation in some or all of the IREs (Goossen, et al, 1990, EMBO J. 9: 4127–4133) (indicated by a Δ in the scheme on top) were analyzed as in FIG. 2a. In 3×IRE, the first IRE is situated 72 nt downstream from the LUC-ORF, while the distance between the third IRE and the CAT coding region was 41 nt.

Figure 3A:
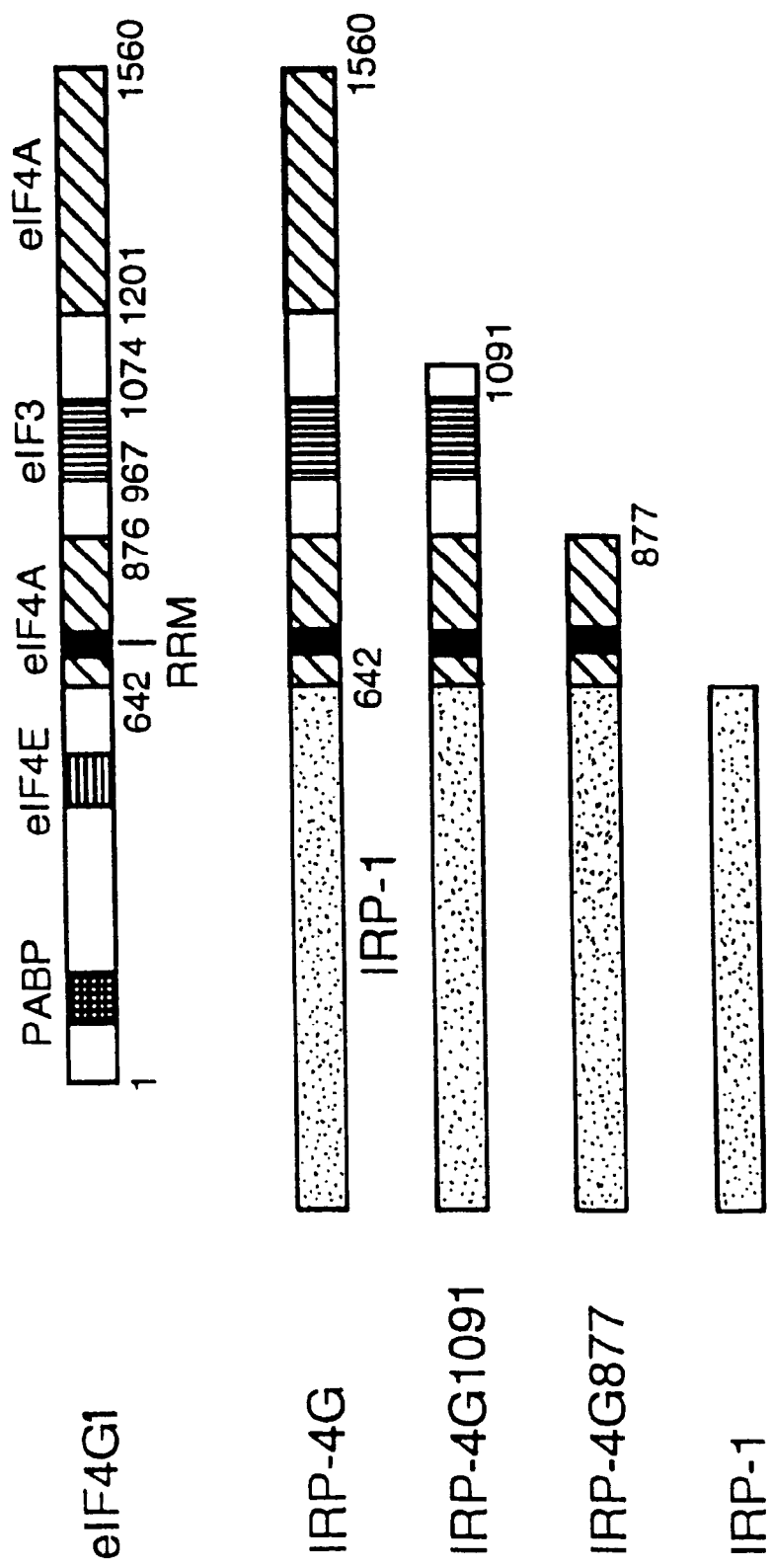
Figure 3B:
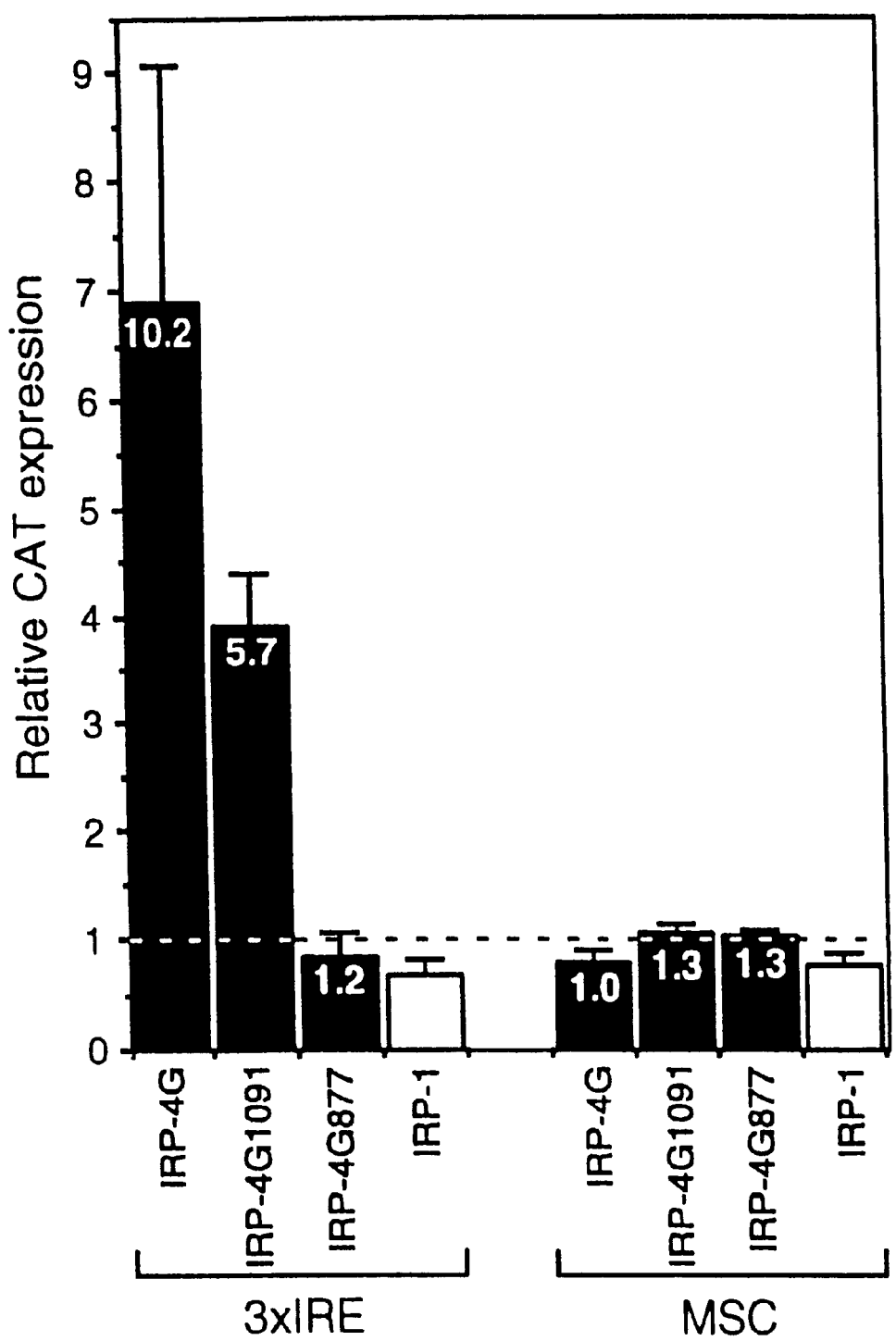
Figure 3C:
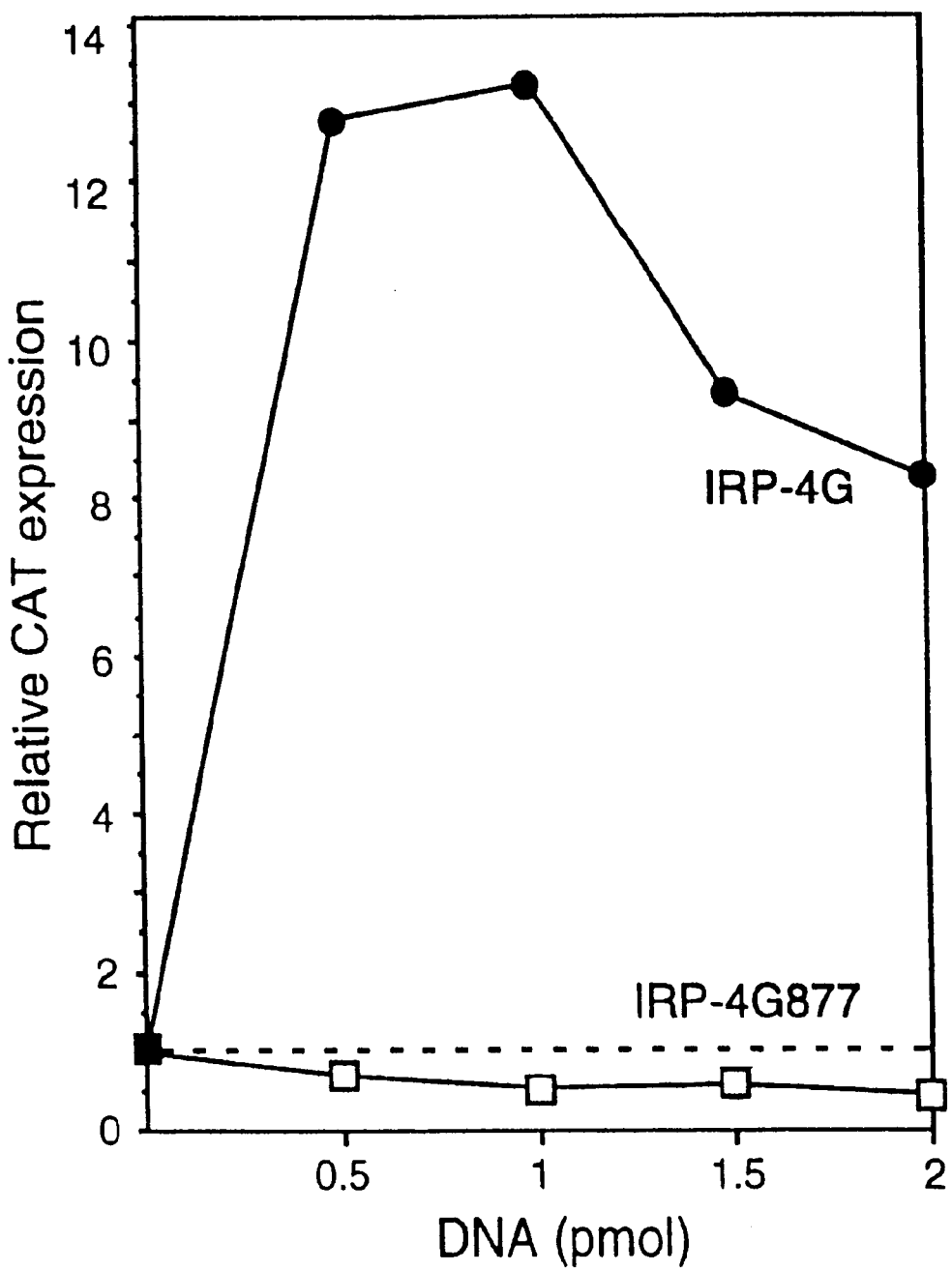

FIGS. 3a–c. The central region of eIF4G1 represents a ribosome recruitment core and functional domain of eIF4G1. FIG. 3a) Schematic representation of the functional domains of eIF4G and of the IRP-4G fusion proteins used in this study. Boxed regions indicate interaction domains for PABP, (Imataka, et al., 1998, EMBO J. 17:7480–7489), eIF4E Mader, et al., 1995, Mol. Cell. Biol. 15:4990–4997, eIF4A, and eIF3 (Lamphear, et al., 1995, J. Biol. Chem. 270:21975–21983; Imataka, et al., 1997, Mol. Cell. Biol. 17:6940–6947) as well as the putative RRM (Goyer, C. et al., 1993, Mol. Cell. Biol. 13:4860–4874; De Gregorio, et al., 1998, RNA 4:828–36) (black box). Amino acids are numbered according to the revised eIF4G1 sequence (Imataka, et al., 1998, EMBO J. 17:7480–7489). As a reference: in this scheme the viral protease 2A cleaves between aa 641 and 642 (Lamphear, et al., 1993, J. Biol. Chem. 268:19200–19203). See FIG. 9 for sequence of human eIF4G1. FIG. 3b) Effector plasmids pSGIRP-4G, pSGIRP-4G1091, pSGIRP-4G877, pSGIRP, or pSG5 were cotransfected with the reporter constructs 3×IRE or MSC as in FIG. 1. The graph shows the effects of the different fusion proteins on relative CAT expression. FIG. 3c) Transfections were performed as in FIG. 3b, establishing the dose-response relationship for pSGIRP-4G and pSGIRP-4G877 plasmids (0–2 pmol) in combination with the reporter 3×IRE. Protein expression levels of IRP-4G and IRP-4G877 were monitored by immunoblotting (also see FIG. 7).

FIGS. 4a–b. The IRE/IRP-4G module functions as an "IRES by rational design". Left panel: Activation of CAT expression using 1 pmol of the effector plasmids pSGIRP-4G, pSGIRP, or pSG5 in combination with the 3×IRE or G243 reporter plasmid. Right panel: schematic representation of the G243 mRNA showing the sequence (SEQ ID NO. 11) and structure. Free energy (ΔG) of formation of the inhibitory stem loop structure in the 5' UTR and its repressive effect on LUC translation are also given.

Figure 5A:
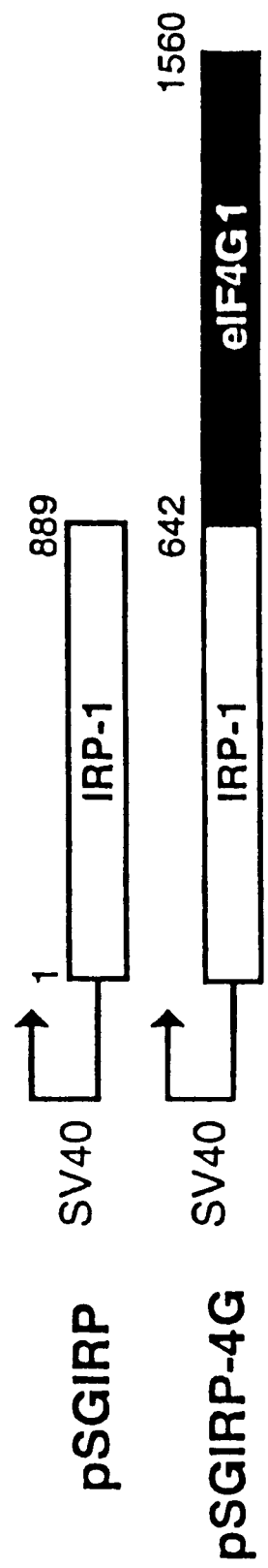
Figure 5B:
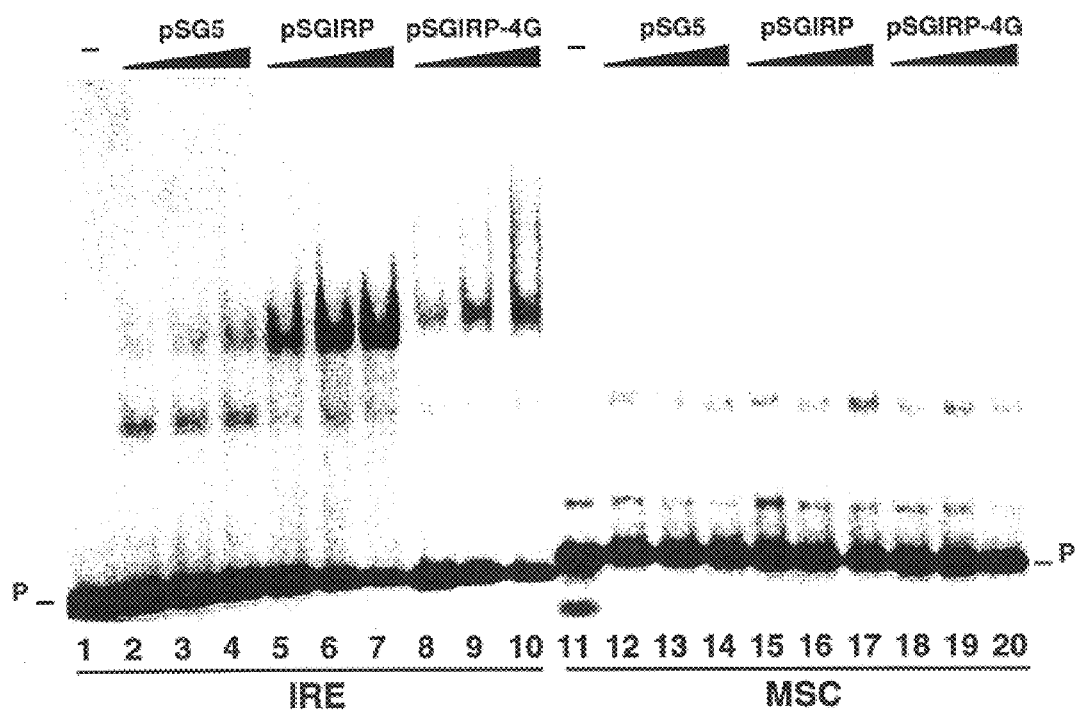
Figure 5C:
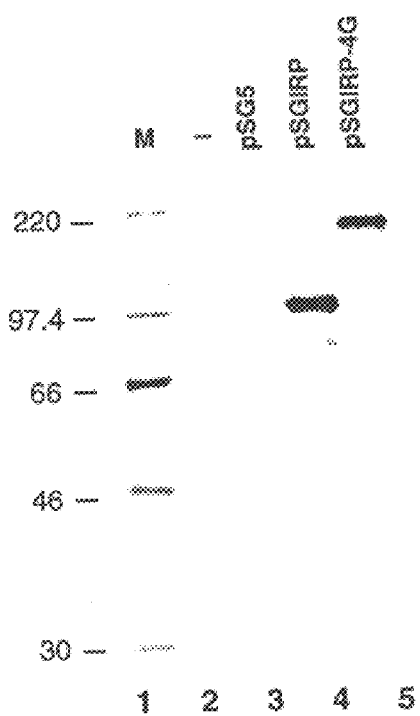
Figure 5D:
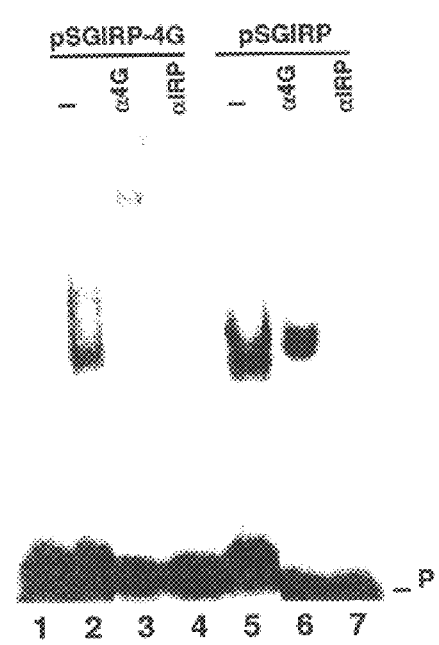

FIGS. 5a–d. IRP-1 and IRP-4G were expressed at similar levels and display specific IRE binding. FIG. 5a) Representation of pSGIRP and pSGIRP-4G expression constructs. FIG. 5b) Overexpressed IRP-1 and IRP-4G displayed similar RNA-binding characteristics by gel mobility shift analysis. HeLa cells were transiently transfected with the effector plasmids pSG5, pSGIRP or pSGIRP-4G. Gel mobility shift analysis of cell lysates was performed with $^{32}$P-labelled IRE (lanes 2–10) or MSC (lanes 12–20) probe (P) as described (Pantopoulos, et al., 1995, RNA 1:155–163). Binding reactions were performed with increasing amounts of cell lysate (7, 14 and 24 µg cellular protein) in the presence of 4 mg/ml heparin at room temperature. Lanes 1 and 11 show controls in the absence of cell extract (−). The slower mobility and the smeared out appearance of high molecular weight complexes formed with IRP-4G indicated the presence of complexes between RNA and the IRP-1/eIF4G fusion protein. FIG. 5c) Similar overexpression of IRP-1 and IRP-4G. HeLa cells were transfected with pSG5 (lane 3), pSGIRP (lane 4) or pSGIRP-4G (lane 5) and incubated in the presence of [$^{35}$S]-methionine. This was followed by immunoprecipitation using polyclonal anti-IRP-1 antibodies and SDS-PAGE (Pantopoulos et al., RNA 1:155–163, 1995). Molecular mass markers (sizes in kDa) are shown in lane 1. The theoretical molecular masses of IRP-1 and IRP-4G are 98 kDa and 201 kDa, respectively. FIG. 5d) The IRE is bound by intact IRP-4G protein. IRE probe was incubated with extracts from cells transfected with pSGIRP-4G (lanes 2–4) or with pSGIRP (lanes 5–7) in the presence of polyclonal antibodies directed against eIF4G1 (α4G, lanes 3 and 6) or IRP-1 (αIRP, lanes 4 and 7). Samples were resolved as in FIG. 5b. αIRP inhibited the binding of both, IRP-1 and IRP-4G to the probe (lanes 4 and 7), while α4G specifically "supershifted" the complex formed with IRP-4G.

Figures 6A, 6B:
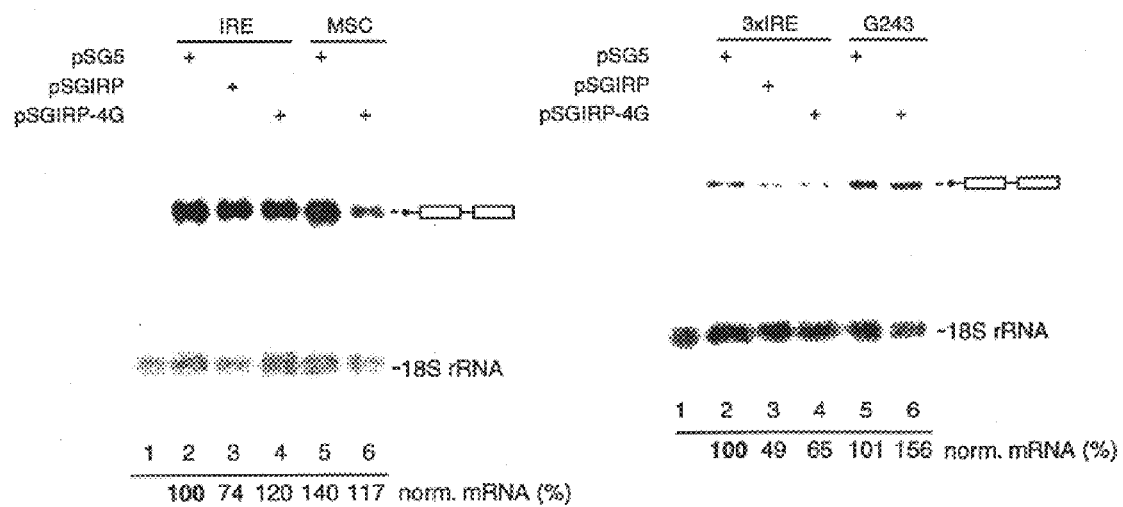

FIGS. 6a–b. Expression of IRP-1 or IRP-4G did not affect the levels of the bicistronic reporter mRNAs. FIG. 6a) Total RNA from untransfected cells (lane 1), or cells transfected with pSGIRE (lanes 2–4) or pSGMSC (lanes 5 and 6) was extracted and subjected to Northern analysis. Consecutive hybridisations were done with a probe covering both, LUC and CAT coding regions of the reporter mRNA (upper panel) and with a probe for 18S rRNA (lower panel) as a loading control. Relative amounts of bicistronic mRNAs in each lane are given below (in %) after correction for transfection efficiency (as measured by β-gal assay) and total RNA amount (calculated from the 18S rRNA signal). The signal in lane 2 was set to 100%. FIG. 6b) Northern analysis as in FIG. 6a but using the reporter constructs pSG3×IRE (lanes 2–4) and pSGG243 (lanes 5 and 6). The presence of a stem-loop structure did not affect the steady-state level of bicistronic mRNA (compare lanes 2 and 5).

Figure 7:
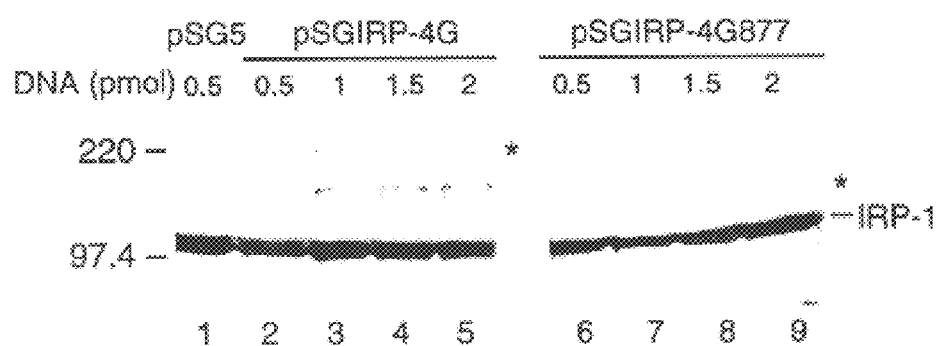

FIG. 7. Titration of IRP-4G and IRP-4G877 expression. Extract samples from FIG. 2c were subjected to immunoblotting with polyclonal antibodies against IRP-1. The asterisks show the positions for intact IRP-4G and IRP-4G877, respectively; the endogenous IRP-1 is also indicated. Due to the simplified cell lysis procedure for the CAT-ELISA, IRP-4G (left panel) suffers substantial proteolysis. Such proteolysis was far less apparent in the immunoprecipitation experiment shown in FIG. 5c. The level of IRP-4G877 protein (lane 9) exceeded that of IRP-4G (lane 2).

Figure 8:
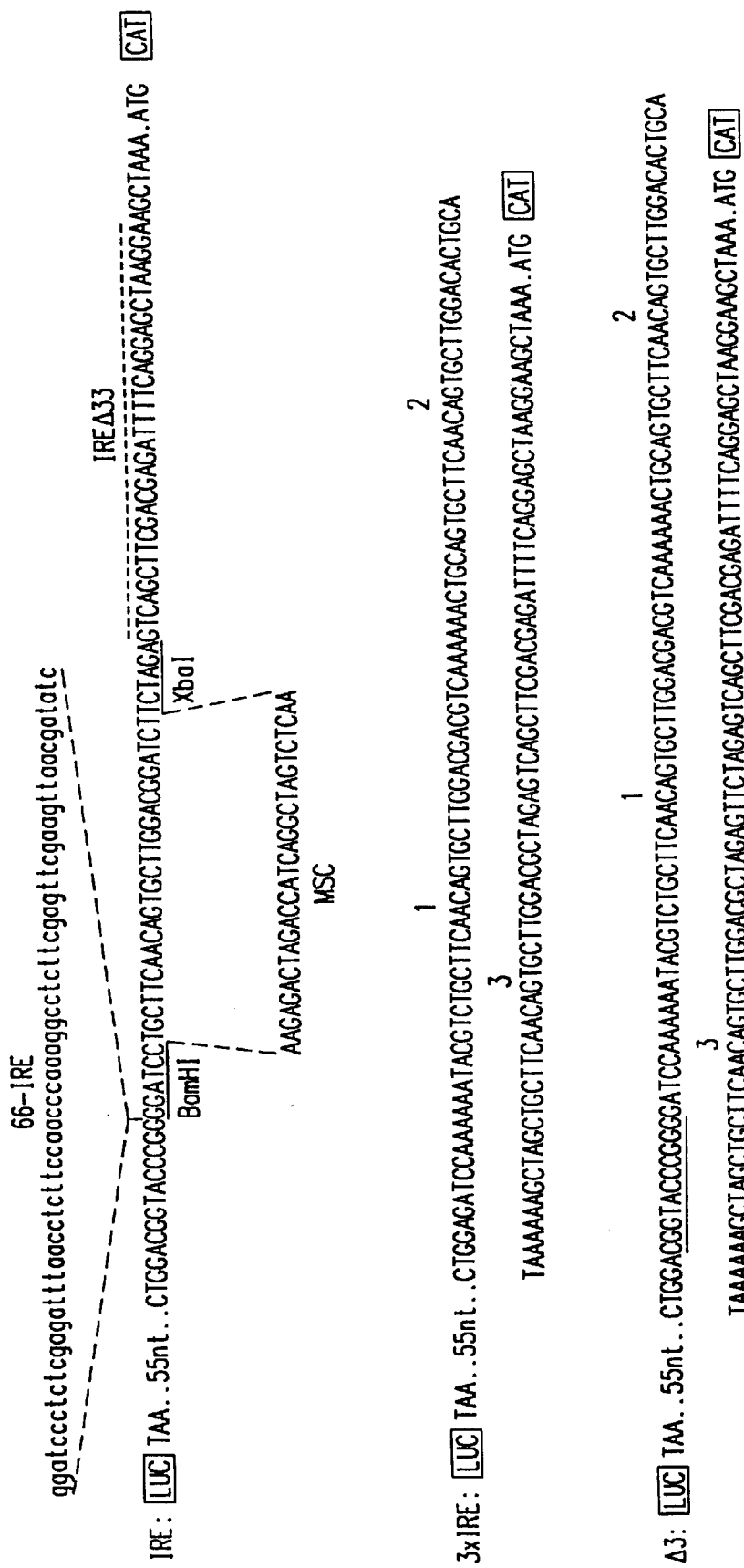

FIG. 8. Sequences of the intercistronic regions of the reporter plasmids used in this study (SEQ ID NOS.: 4, 6, 7 and 9). The IREs are shown in bold letters, the conserved cytosines which were deleted in the Δ constructs (see FIG. 2b) are outlined. The dashed line indicates sequences which were deleted from IRE-Δ33 (SEQ ID NOS.: 4 and 6). The sequence and the position of the insertion in 66-IRE is also shown on top (SEQ ID NO.: 4). The construction of Δ3 result in minor additional sequences (underlined) before and after the triple Δ3×IRE which are not present in 3×IRE (SEQ ID NOS.: 7 and 9).

FIGS. 9a–h. Nucleotide and protein sequences of human eIF4G1(SEQ ID NOS.: 1 and 2, respectively; Genbank accession number AF104913; Imataka, et al., 1998, EMBO J. 17:7480–7489).

5. DETAILED DESCRIPTION OF THE INVENTION

The present invention provides methods and products based on the achievement of translation from monocistronic or multicistronic RNAs in eukaryotic cells. In preferred embodiments, translation of an mRNA coding region that is not the 5' cistron is achieved by providing eIF4G-like protein, or derivative thereof functional in translational activation, fused to a protein (the term "protein" being used herein as referring to protein, peptide, or polypeptide), which protein binds to an RNA binding site in the intercistronic space 5' to the mRNA coding region, thereby activating translation of the coding region in a cell. In addition or alternatively, where an RNA binding site is 5' to the 5' most coding sequence in an RNA, increased translation of such coding sequence whether in a monocistronic or multicistronic RNA, can also be achieved by the methods of the invention. Details of such embodiments, and variations thereof in which interacting proteins and inhibitors and facilitators of protein interactions, RNA-binding proteins, and protein-binding RNA sites, can be identified, are also described. As used herein, "coding region" and "open reading frame" and "gene" are used interchangeably and refer to a nucleotide sequence bounded at the 5' end by a translation start codon and at the 3' end by a translation stop codon.

For purposes of convenience of description and not by way of limitation, the detailed description is divided into the subsections set forth below.

5.1. FUSION PROTEINS COMPRISING eIF4G-LIKE PROTEINS AND DERIVATIVES THEREOF

The present invention provides methods of regulating and activating translation using a ribosome recruitment protein, an eIF4G-like protein. The invention further relates to fusion proteins comprising an eIF4G-like protein, or a translationally active derivative (e.g., fragment) thereof, fused to an RNA-binding protein which is capable of binding an HBS. Such fusion protein thus acts as a translational activator of a coding region for which the HBS is in the non-coding region just 5' thereto. By way of explanation and not by way of limitation, the mechanism for such is that the binding of the RNA-binding protein domain to the HBS leads to the activation of translation by bringing the fused eIF4G-like protein (or functional derivative thereof) into proximity with the HBS.

Without limitation, eIF4G-like proteins act to recruit ribosomes to the RNA to allow translation of the encoded protein(s). Such fusion protein therefore promotes translation of a coding region or coding region adjacent to an HBS. eIF4G-like proteins are proteins functional in ribosome recruitment that activate translation according to the methods of the invention. eIF4G-like proteins may be of any species. eIF4G-like proteins include but are not limited to human eIF4G1(Genbank accession number AF104913; Imataka, et al., 1998, EMBO J. 17:7480–7489), human eIF4G2 (Genbank accession number T08424; Gradi et al., 1998, Mol. Cell Biol. 18:334–342), human p97/DAP-5 (Genbank accession number U73824; Imataka et al., 1997, EMBO J. 16:817–825), eIF(iso)4G-p82 (Genbank accession number M95747; Allen et al., 1992, J. Biol. Chem. 267:23232–236), and proteins that bind to any of the foregoing, such as eIF4E. In a preferred embodiment, the eIF4G-like protein is human eIF4G1.

An eIF4G-like protein or any derivative thereof functional in ribosome recruitment (translationally active) may be used in a fusion protein for the practice of the present invention. Nucleic acids comprising the same are also provided. Preferably the eIF4G-like protein is human eIF4G1, having a sequence shown in FIG. 9 (SEQ ID NOS.:1 and 2; see also, Genbank accession number AF104913; Imataka, et al., 1998, EMBO J. 17:7480–7489), although other eukaryotic species (e.g., mammalian, primate, animal, mouse, rat, rabbit, yeast, worm, fungus, insect, plant, fly, etc.) can be employed. It is preferred that the eIF4G-like protein be of the same species as the host cell used in the methods of the invention. In particular, as an alternative to the use of a full-length eIF4G-like protein in the fusion proteins used in the methods of the invention, a fragment or other derivative of an eIF4G-like protein that retains the ability to bind to eIF3 and is thus translationally active is used in the instant invention. In a preferred embodiment, a derivative (e.g., fragment) of eIF4G1is employed that comprises an eIF3 binding domain (e.g., amino acids 967–1074 of human eIF4G1 (SEQ ID NO:2) as numbered in Imataka, et al., 1998, EMBO J. 17:7480–7489). In a specific embodiment, such derivative of eIF4G lacks one or both of the PABP domain (amino acids 132–160 of human eIF4G1(SEQ ID NO:2)) and the eIF4E binding domain (amino acids 569–582 of human eIF4G1(SEQ ID NO:2)) (Imataka et al. numbering). In another embodiment, the derivative of eIF4G 1 lacks both the PABP and eIF4E domains, but comprises the eIF3 binding domain and one or both eIF4A binding domains, and optionally, the RRM domain. In a specific embodiment, a truncated eIF4G1protein is used that lacks sequences amino-terminal to the amino-terminal most eIF4A domain. In another specific embodiment, a truncated human eIF4G1protein is used that contains amino acids 489–1404 of human eIF4G1(SEQ ID NO:2; Imataka et al., numbering). In an alternative specific embodiment, the fusion protein comprises an eIF4G-like protein or derivative that is not human eIF4G1$_{489-1404}$, particularly eIF4G1$_{489-1404}$ fused to IRP.

In a specific embodiment, fusion proteins comprising an RNA-binding protein fused to an eIF4G-like protein or a translationally active derivative thereof are used for the methods of the invention. In one embodiment the RNA-binding protein is fused to a translationally active derivative of a eIF4G-like protein. In a further embodiment, the translationally active derivative comprises an eIF3 binding domain of eIF4G1. In another embodiment, the translationally active derivative lacks one or more of the PABP domain and the eIF4E binding domain. In another specific embodiment, the invention provides nucleotide sequence encoding the fusion protein, and expression vectors comprising such sequence.

In another specific embodiment, fusion protein comprising an eIF4G-like protein or translationally active derivative thereof is fused to a second, different protein. In one embodiment the translationally active derivative of the eIF4G-like protein is fused to the second protein. In another embodiment, the translationally active derivative comprises an eIF3 binding domain of eIF4G1. In yet another embodiment, the translationally active derivative lacks one or more of the PABP domain and the eIF4E binding domain. The invention provides nucleotide sequence encoding the fusion protein, and expression vectors comprising such sequence.

In yet another specific embodiment fusion protein comprising an RNA-binding protein is fused to a second, different protein. In one embodiment the RNA-binding protein is selected from the group consisting of IRP-1, bacteriophage MS2 coat protein, spliceosomal protein U1A, a λ box B binding protein, and an arg-rich protein. The invention provides nucleotide sequence encoding the fusion protein, and expression vectors comprising such sequence.

eIF4G-like protein derivatives and methods of making an eIF4G-like derivatives are also described in Section 5.5 ("Protein Derivatives and Analogs") infra.

The eIF4G-like fusion proteins of the invention can be produced by ligating the appropriate nucleotide sequences encoding the desired amino acid sequences to each other by methods commonly known in the art. The resulting nucleic acid is then inserted into an appropriate expression rector, or is flanked by sequences that will promote intrachromosomal insertion (e.g., by homologous recombination or random integration) and is introduced into the desired host cell, where it will be expressed. Alternatively, in a less preferred embodiment, the fusion protein is made by protein synthesis methods, e.g., a peptide synthesizer, and then is introduced into the cell (e.g., by microinjection, placing it in cell culture medium used to culture the cell, etc.). The eIF4G-like sequences can be situated amino- or carboxy-terminal to the sequence of the different protein.

Where the fusion protein comprising an eIF4G-like protein or a translationally active derivative thereof is constructed also to comprise an RNA-binding protein (or RNA-binding derivative thereof), the RNA-binding protein (or derivative thereof) may be any known in the art, including but not limited to those listed in Section 5.3 below In a specific embodiment a population of nucleic acids is constructed, wherein each nucleic acid in the population is a vector comprising (a) an origin of replication; (b) a nucleotide sequence encoding the fusion comprising an eIF4G-like protein or translationally active derivative thereof fused to a second, different protein; and (c) a promoter operably linked to said nucleotide sequence; wherein the identity of said second, different protein varies among said population. In one embodiment the population has a complexity of at least 100. In another embodiment the nucleotide sequences are those of a cDNA library. In another embodiment, the nucleotide sequences are of a random or biased peptide expression library.

In another specific embodiment a population of nucleic acids is constructed, wherein each nucleic acid in the population is a vector comprising (a) an origin of replication; (b) a nucleotide sequence encoding the fusion comprising an RNA-binding protein fused to a second, different protein; and (c) a promoter operably linked to said nucleotide sequence; wherein the identity of said second, different protein varies among said population. In one embodiment the population has a complexity of at least 100. In another embodiment the nucleotide sequences are those of a cDNA library. In another embodiment, the nucleotide sequences are of a random or biased peptide expression library. In specific embodiments, such nucleic acids may be used to construct recombinant cells or transgenic organisms. Such nucleic acids may further be used to construct a population of recombinant cells comprising the population of nucleic acids described above. In another specific embodiment, the above fusion proteins may be produced by subjecting a recombinant cell comprising the nucleic acid to conditions such that the nucleotide sequence is expressed by the cell.

In another embodiment of the invention, a nucleic acid may be constructed comprising (a) a nucleotide sequence encoding an eIF4G-like protein or a translationally active derivative thereof; and (b) a polylinker region 5' or 3' to said nucleotide sequence that allows for insertion after restriction enzyme digestion of a nucleic acid fragment in the correct reading frame so as to encode a fusion protein to the eIF4G-like protein or derivative.

In another embodiment of the invention a nucleic acid may be constructed comprising (a) a nucleotide sequence encoding an RNA-binding protein; and (b) a polylinker region 5' or 3' to said nucleotide sequence that allows for insertion after restriction enzyme digestion of a nucleic acid fragment in the correct reading frame so as to encode a fusion protein to the RNA-binding protein.

In yet another embodiment, a fusion protein of the invention is a fusion protein between an RNA-binding protein and a protein which is capable of binding to an eIF4G-like protein (e.g., eIF4E). In a specific embodiment, an RNA-binding protein is fused to a domain of mammalian eIF4E which is capable of binding to an eIF4G-like protein (e.g., human eIF4G1). Thus the fusion of an RNA-binding protein to an eIF4G-like binding protein leads to the activation of translation by the methods of the invention by recruiting eIF4G-like protein to the vicinity of the RNA molecule to be translated. Thus, any protein or domain which binds to an eIF4G-like protein may be fused to an RNA-binding protein and used to regulate translation by the methods of the invention. In a preferred embodiment, the invention provides a method of producing a protein comprising contacting within a eukaryotic cell: (a) an RNA molecule comprising (i) a coding region encoding said protein, and (ii) a protein-binding site in a noncoding region 5' and adjacent to said coding region; and (b) a fusion protein comprising (i) an RNA-binding protein that binds to said protein-binding site, fused to a second protein, said second protein capable of binding to an eIF4G-like protein.

5.2. RNA CONTAINING A PROTEIN-BINDING SITE FOR TRANSLATION

The present invention provides for activation of translation in a eukaryotic cell or organism of one or more open reading frames from an RNA molecule, preferably of downstream cistrons from a multicistronic RNA molecule (e.g., containing more than one independent cistron (protein coding sequences), preferably an mRNA molecule. The multicistronic RNA molecule to be translated contains, or is constructed to contain a protein-binding site in the intercistronic space 5' to the coding region. Preferably, the protein-binding site is a heterologous protein-binding site (HBS) (e.g., one that is not native to the downstream coding region). RNA that may be translated by the methods of the invention may be from any source known in the art including but not limited to those described below.

RNA for translation by the methods of the invention may have a single cistron (e.g., monocistronic) or be multicistronic. RNA for translation by the methods of the invention may be endogenous RNA (e.g., native mRNA), or heterologous RNA (e.g., non-native, or RNA introduced into a cell) or, most preferably, be RNA transcribed from DNA which has been introduced into a cell. Translation by the methods of the invention may be performed in vivo, or in vitro. Thus, in one embodiment, endogenous mRNA may be isolated from a cell and translated in vitro using the methods of the invention. In another embodiment, mRNA is transcribed in vitro from a DNA molecule, preferably a cDNA, and translated in vitro by the methods of the invention.

In a preferred embodiment, DNA molecule encoding an RNA is introduced into an in vivo system (e.g., a cell) where the DNA is transcribed to produce the RNA and the RNA is translated by the methods of the invention. The DNA can be cDNA, or genomic, and is most preferably cDNA. In a preferred aspect of this embodiment, a recombinant DNA molecule is transcribed within the cell so as to produce a multicistronic RNA containing protein-binding site(s) in the intercistronic region 5' and adjacent to each coding region that is desired to be translated. In the presence of a fusion protein comprising an eIF4G-like protein or a translationally active derivative thereof, fused (either in the amino- or carboxy- terminal direction) to an RNA-binding protein that specifically binds to the protein-binding site, translation of the coding region occurs within the cell, even when the coding region is not the 5' most coding region of the RNA molecule. In preferred aspects, the protein-binding site in the region 5' to the adjacent coding region is a HBS. HBSs that are in the intercistronic regions 5' and adjacent to different coding regions can be the same or different. Different HBSs activate transcription of their adjacent downstream cistron when bound by their cognate binding protein fused to an eIF4G-like protein (or a translationally active derivative thereof). Thus, the presence or absence of the cognate binding-protein fusion protein for the respective HBS allows regulation (turning on and off, respectively) of the translation of the downstream cistron adjacent to the HBS. Moreover, the inventors have discovered that increasing the number of HBSs (for which a cognate RNA-binding protein/eIF4G-like protein fusion is present in the cell) in the intercistronic region 5' to the adjacent coding region increases the amount of translation of the coding region. In particular, the increase in amount of translation product correlates with the increase in number of such HBS (when such HBSs are identical). Thus, stoichiometry of expression of proteins from each of the cistrons of a multicistronic message can be controlled by varying the number and type of HBSs in the intercistronic regions just upstream of each cistron and the presence or absence of the RNA-binding protein/eIF4G-like protein fusion protein or of the multicistronic RNA (by expressing the fusion protein and/or multicistronic RNA from inducible promoters).

In a specific embodiment the invention provides a nucleic acid encoding an RNA, said RNA comprising a coding region with one or more heterologous protein-binding sites in a non-coding region 5' and adjacent to the coding region. In one embodiment the DNA molecule is purified. In another embodiment, the binding site is selected from the group consisting of IRE, MS2 RNA replicase site, U1A sRNA site, and a λ box B site.

In a specific embodiment the invention provides a nucleic acid encoding an RNA, said RNA comprising a coding region with one or more heterologous protein-binding sites in a non-coding region 5' and adjacent to the coding region. In one embodiment the DNA molecule is purified. In another embodiment, the binding site is selected from the group consisting of IRE, MS2 RNA replicase site, U1A snRNA site, and a λ box B site.

An important advantage of the instant invention is that a multicistronic RNA molecule may be constructed such that it provides an internal control or calibration standard for the cap-dependent translation of said RNA. Specifically, construction of a multicistronic RNA molecule comprising (a) a 5' most cistron (or reporter gene) without an upstream HBS; and (b) one or more downstream cistrons linked to one or more HBS, allows for the 5' most cistron to be an indicator of basal levels of translation (e.g., the 5' most cistron without an HBS is translated in a cap-dependent manner). Thus, translation of the 5' most cistron or reporter gene indicates the cap-dependent translation from the multicistronic RNA molecule. The 5' most cistron without an HBS serves as a calibration standard for the translation of downstream cistrons having an HBS. In a preferred embodiment, by way of example, a multicistronic RNA is constructed such that a first reporter gene (e.g., LUC) is the 5' most cistron; a second reporter gene (e.g., CAT) is positioned downstream to the first reporter gene; and an HBS is positioned 5' and adjacent to the second reporter gene (e.g., the HBS is between the LUC and CAT genes). Translation of the LUC gene thus indicates the cap-dependent translation, while translation of the CAT gene indicates the HBS-mediated translational activation.

In a preferred embodiment, translation of the 5' most cistron of a multicistronic mRNA can be shut off, while allowing expression of the downstream cistrons according to the invention, by constructing the mRNA so as to have a stem-loop 5' to the 5' most cistron (e.g., by transcribing a DNA encoding such a loop 5' to the rest of the RNA) (see example § 6 infra). An HBS in the RNA molecules of the invention is positioned so as to be able to activate translation of the nearest 3' cistron when bound by its cognate RNA-binding protein-eIF4G-like protein fusion protein. In a specific embodiment, the HBS is 5 to 300 nucleotides upstream of the downstream cistron, more preferably 10 to 200, or 75 to 200, and most preferably from 100 to 150 nucleotides upstream.

The invention also provides methods for identifying an HBS. Any method known in the art to identify a nucleic acid which binds to a specific protein may be used. For example, an HBS may be identified by screening random RNA oligonucleotides for ability to bind to a specific RNA-binding protein. In another embodiment, an HBS may be identified by a foot printing assay.

In preferred embodiments, the RNA to be translated is multicistronic and encodes two, three, four, 5–10, 10–20, or 20 or more proteins each having one or more protein-binding sites, upstream of their adjacent coding sequences, preferably HBSs, such that said proteins are translated by the methods of the invention. In further preferred embodiments, the RNA contains one, two, three, four, 5–10, 10–20, or 20 or more heterologous binding sites (HBS) in the intercistronic region 5' to (controlling expression of) particular coding regions.

In a preferred embodiment, RNA is transcribed from a recombinant DNA, which is introduced into a host cell. Any gene, or genes-of-interest may be used for the construction of such a DNA molecule. In a specific embodiment, the DNA molecule encodes an RNA that contains a single cistron, upstream of which are one or more HBSs. In a preferred embodiment, the RNA is multicistronic. In a further preferred embodiment, the multicistronic RNA molecule contains one or more HBSs in the intercistronic region 5' to each downstream cistron, and optionally, 5' to the 5' most cistron. In an embodiment wherein the 5' most cistron of such a multicistronic message does not have an HBS 5' to it, translation of the 5' most cistron serves as a control for wild-type translation. In one embodiment, the HBSs in different intercistronic regions of the RNA molecule are the same (e.g., have the same nucleotide sequence). In another embodiment, the HBSs in different intercistronic regions of the RNA molecule are different from each other (i.e. have different nucleotide-sequences).

Any method available in the art can be used to construct a DNA or cDNA encoding one or more proteins-of-interest which can be used to produce a monocistronic, or preferably, multicistronic RNA in a suitable cell or organism. In particular, the polymerase chain reaction (PCR) can be used to amplify a coding sequence in a cDNA library. Oligonucleotide primers that hybridize to sequences at the 3' and 5' termini can be used as primers to amplify by PCR sequences from a nucleic acid sample (RNA or DNA), preferably a cDNA library.

PCR can be carried out, e.g., by use of a Perkin-Elmer Cetus thermal cycler and Taq polymerase (Gene Amp™). The DNA being amplified is preferably cDNA from any eukaryotic species.

After successful amplification of the nucleic acid containing all or a portion of a nucleic acid encoding desired coding region, that segment may be inserted into an appropriate cloning or expression vector.

Any eukaryotic cell potentially can serve as the nucleic acid source for the coding region-of-interest to be used. The nucleic acids can be isolated from vertebrate, mammalian, human, porcine, bovine, feline, avian, equine, canine, as well as additional primate sources, insects, plants, yeast, fungus, worm, fly, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, New York; Glover, D.M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will contain only exon sequences. Whatever the source, the coding region is preferably molecularly cloned into a suitable vector for propagation of the gene.

Preferably, coding regions used to construct a DNA encoding a RNA to be translated are isolated from a cDNA source. In a specific embodiment, the coding regions used to construct DNA encoding the RNA molecule encode proteins with therapeutic utility (e.g., for gene therapy, See Section 5.6 below).

Alternatives to isolating a DNA include, but are not limited to, chemically synthesizing the gene sequence itself from a known sequence. Additionally, a variety of vectors containing a gene-of-interest are commercially available. Such vectors and genes may be purchased and used in the engineering of a nucleic acid encoding a heterologous RNA. For example, restriction enzyme digestion may be applied to commercially purchased vectors in order to excise the gene-of-interest. Such gene is then purified by standard methods known in the art, such as by agarose gel electrophoresis. Such gene may then be used to construct a vector encoding a RNA to be translated according to the methods of the invention. Other methods are possible and within the scope of the invention.

Isolated DNA encoding a RNA (preferably a multicistronic RNA) can be inserted into an appropriate expession vector suitable for the host cell to be employed such that the DNA is transcribed to produce the RNA. A large number of vector-host systems known in the art may be used. Possible vectors include, but are not limited to, plasmids or modified viruses, but the vector system must be compatible with the host cell used. The insertion into a vector can, for example, be accomplished by ligating the DNA fragment into a vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. More than one coding region may be introduced into the vector for the construction of a multicistronic coding vector. In one embodiment, two different coding regions are inserted, and serve to encode part of the multicistronic RNA. In another embodiment, three, four, or five different coding regions are inserted. In yet another embodiment, six, seven, eight, nine, or ten different coding regions are inserted. In another embodiment, 10–20 or 20 or more coding sequences are inserted. In one embodiment, the coding sequences are inserted such that the coding regions are within the same reading frame and able to be transcribed into a monocistronic RNA molecule. In a preferred embodiment, the coding sequences are inserted such that the coding regions are able to be transcribed into a multicistronic RNA molecule.

In one embodiment, the nucleic acids to be used in the construction of a nucleic acid encoding a multicistronic RNA are assembled into a single nucleic acid by any method known in the art. The assembled nucleic acid encoding a multicistronic RNA is then inserted into an appropriate vector.

Construction of the vectors encoding a multicistronic RNA molecule with one or more coding regions (cistrons, genes) of interest, preferably includes the insertion of heterologous nucleic acid sequences that are transcribed to form binding sites (e.g., an HBS) for RNA-binding proteins. Alternatively, in a less preferred embodiment, a protein binding site upstream of the coding region that is native to that coding region, is used. In one embodiment, an HBS-coding sequence is inserted by ligating the HBS-coding sequences 5' to the coding region-of-interest. In a preferred embodiment, multiple HBS-coding sequences are inserted 5' to an adjacent coding sequence. In a most preferred embodiment, one or more HBS-coding sequences are inserted so as to appear in the intercistronic region 5' to each coding sequence within the multicistronic RNA molecule encoded by a DNA molecule. In yet another embodiment, one or more HBS-coding sequences may be inserted 5' to some, but not all of adjacent coding regions.

Recombinant nucleic acid molecules such as vectors encoding the RNA can be introduced into host cells via transformation, transfection, infection, electroporation, microinjection etc., so that many copies of the RNA are generated by transcription inside the cell.

In another embodiment, recombinant molecules encoding the RNA molecules are introduced into host cells such that they become integrated into the host cell genome. In one embodiment, the recombinant molecule is flanked by sequences known to promote homologous recombination. In a further embodiment, the integrated recombinant molecule is transcribed within the cell to produce a heterologous RNA molecule.

In a specific embodiment, individual coding regions of a multicistronic RNA encode different subunits of a multi-subunit polypeptide.

In a less preferred embodiment, endogenous RNA (that contains a protein binding site 5' to the cistron(s) in the molecule) is translated by the methods of the invention. In a further embodiment, both an endogenous and a recombinant RNA is translated by the methods of the invention. Sources of endogenous RNA can consist of largely conventional steps of RNA preparation from cell or tissue samples, preferably total poly(A) purified RNA is used but less preferably total cellular RNA can be used. Alternatively, RNA may be synthesized by any method known in the art. As a less preferred alternative to intracellular production of RNA transcription by a recombinant DNA molecule, RNA to be translated by the method of the invention may be directly introduced into a cell, by any method known in the art. In several embodiments, RNA is introduced into host cells via transformation, transfection, infection, electroporation, microinjection etc.

5.2.1. EXPRESSION OF NUCLEIC ACIDS ENCODING RNA-BINDING PROTEIN/eIF4G-LIKE PROTEIN FUSION PROTEINS

The nucleotide sequence coding for an eIF4G-like protein, fused to an RNA-binding protein which is capable of recognizing an HBS (e.g., RNA-binding protein/eIF4G-like protein fusion protein) or a functionally active analog or fragment or other derivative thereof, can be inserted into an appropriate expression vector, e.g., a vector which contains the necessary elements for the transcription and translation of the inserted protein-coding sequence and/or for carrying out the methods of the invention. A variety of eukaryotic host-vector systems may be utilized to express the protein-coding sequence. These include but are not limited to mammalian cell systems infected with virus (e.g., vaccinia virus, adenovirus, etc.); insect cell systems infected with virus (e.g., baculovirus); or microorganisms such as yeast containing yeast vectors. The expression elements of vectors vary in their strengths and specificities. Depending on the host-vector system utilized, any one of a number of suitable transcription and translation elements may be used.

Any of the methods previously described for the insertion of DNA or nucleic acid fragments into a vector may be used to construct expression vectors containing a chimeric gene (e.g., encoding a fusion protein) consisting of appropriate transcriptional/translational control signals and the protein coding sequences. These methods may include in vitro recombinant DNA and synthetic techniques and in vivo recombinants (genetic recombination). Expression of a nucleic acid sequence encoding a fusion protein or peptide fragment may be regulated by a second nucleic acid sequence so that the fusion protein or peptide is expressed in a host cell transformed with the recombinant DNA molecule. For example, expression of a RNA-binding protein may be controlled by any promoter/enhancer element known in the art. A promoter/enhancer may be homologous (i.e. native) or heterologous (i.e. not native). Promoters which may be used to control the expression of a fusion protein include, but are not limited to, the SV40 early promoter region (Benoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), plant expression vectors comprising the nopaline synthetase promoter region (Herrera-Estrella et al., Nature 303:209–213), the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120), promoter elements from yeast or other fungi such as the Gal4-responsive promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); a gene control region which is active in pancreatic beta cells (Hanahan, 1985, Nature 315:115–122), an immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in erythroid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In another embodiment of the invention, the plasmids encoding the RNA-binding protein fusion and the eIF4G-like protein fusions are isolated from yeast cells by transforming the yeast DNA into E. coli and recovering the plasmids from E. coli (see e.g., Hoffman et al., 1987, Gene 57:267–272). This is possible when the plasmid vectors used for both the RNA-binding protein fusion and the eIF4G-like protein fusion are shuttle vectors that can replicate both in E. coli and in yeast. Many such shuttle vectors are known in the art and can be used. Alternatively, if a shuttle vector is not used, the yeast vector can be isolated, and the insert encoding the fusion protein subcloned into a bacterial expression vector for growth in bacteria. Growing up the interacting clones in bacteria yields large quantities without the use of amplification reactions such as PCR.

In a specific embodiment, a vector is used that comprises a promoter operably linked to a nucleic acid encoding a fusion protein and one or more origins of replication, and, optionally, one or more selectable markers (e.g., an antibiotic resistance gene).

Promoters can be inducible, or constitutive. Expression from certain promoters can be elevated in the presence of certain inducers; thus, expression of the genetically engineered RNA-binding protein/eIF4G-like protein fusions may be controlled. Inducible promoters may be used to control expression of the multicistronic RNA and/or eIF4G fusion proteins and/or RNA-binding fusion proteins (see infra) of the invention, such that the RNA or fusion protein is produced, and thus translation occurs only in the presence of the inducer.

In another specific embodiment, the promoter that is operably linked to the nucleic acid encoding a fusion protein is not a native promoter to either genes of the fusion protein.

One preferred method for producing a protein of the invention comprises contacting within a eukaryotic cell with: (a) an RNA molecule comprising (i) a coding region encoding said protein, and (ii) a protein-binding site in a noncoding region 5' and adjacent to said coding region; and (b) a fusion protein comprising (i) an RNA-binding protein that binds to said protein-binding site, fused to an eIF4G-like protein or a translationally active derivative thereof. In one embodiment the RNA molecule comprises two or more coding regions, and wherein a heterologous protein-binding site is in an intercistronic region, or has two or more heterologous protein-binding sites in at least one intercistronic region. In another embodiment at least two coding regions (a) are 3' to another coding region, and (b) each encodes a different subunit of a multi-subunit protein.

Another preferred method of producing a protein of the invention comprises recombinantly expressing a fusion protein with a eukaryotic cell, wherein the cell contains a DNA molecule that is transcribed within the cell to produce a monocistronic or multicistronic RNA containing a heterologous protein-binding site in a region 5' and adjacent to a coding region encoding said protein; wherein the fusion protein comprises (i) an RNA-binding protein that binds to said protein-binding site, fused to an eIF4G-like protein or a translationally active derivative thereof. In one embodiment the DNA molecule is a plasmid expression vector. In one embodiment the plasmid comprises an inducible promoter controlling production of said RNA. In another embodiment the fusion protein is expressed from a plasmid expression vector comprising a promoter operably linked to a nucleotide sequence encoding said fusion protein. In yet another embodiment the two or more identical heterologous protein-binding sites are in said intercistronic region. In still another embodiment, two or more intercistronic regions contain the heterologous protein-binding site, each of said two or more intercistronic regions encoding a different subunit of a multi-subunit protein.

In addition, a host cell strain may be chosen which modulates the expression of the inserted sequences, or modifies and processes the gene product in the specific fashion desired.

The host cell is eukaryotic, preferably a cell line, preferably mammalian, most preferably human may be used for the method of the invention. Cells may be derived from human (e.g., HeLa cells), primate, mouse, rabbit, chicken, etc., although may also be from a transgenic non-human animal. Numerous eukaryotic cell lines may be purchased from ATCC (American Type Culture Collection, Rockville, Md.). In one embodiment, the eukaryotic cell is a mammalian cell. In a most preferred embodiment, eukaryotic cell is derived from a human. In other embodiments, the host cell is derived from a mouse, monkey, or rat.

5.3. PROTEIN-BINDING RNA SITES AND THEIR COGNATE RNA-BINDING PROTEINS

The protein-binding RNA sites and RNA-binding proteins for use in the instant invention may be any known in the art or identified by appropriate assay. Preferably, the RNA molecules to be translated according to the invention (or the DNA molecules encoding them) are constructed such that the protein-binding site in such RNA molecule is heterologous (not found associated with the downstream cistron in the native gene containing that cistron), e.g., is an HBS. An HBS may be endogenous to a cell or may be a synthetic site which is capable of binding an RNA-binding protein.

RNA-binding proteins (or RNA-binding derivatives thereof) and protein-binding RNA sites (or protein-binding derivatives thereof) that can be used in the practice of the present invention include but are not limited to the following:

(1) iron regulatory protein (IRP-1), which binds to iron-responsive elements (IREs) (Hentze and Kuhn, 1996, Proc. Natl. Acad. Sci. USA 93:8175–8182);

(2) bacteriophage MS2 coat protein, which binds to the MS2 replicase mRNA (Lowary and Uhlenbeck, 1987, Nucl. Acids Res. 15:10483–10493); Witherell et al., 1991, Progr. Nucl. Acids Res. Mol. Biol. 40:185–220;

(3) Spliceosomal protein U1A, which binds to loop 2 of U1snRNA (Scherly et al., 1989, EMBO J. 8:4163–4170).

(4) arginine-rich peptides that bind to RNA sites (in λ P22) (Tan and Frankel, 1995, Proc. Natl. Acad. Sci. USA 92:5282–5286). Arginine-rich peptides include but are not limited to peptides of HIV-1 Rev, λN, P22, BMV Gag, CCMV Gag, Yeast PRP6, or HIV Tat.

The RNA-binding protein may be a naturally occurring protein or a non-naturally occurring protein, may be synthetic, and may be a peptide (e.g., of 50 amino acids of less), or a polypeptide, etc.

In a preferred embodiment of the invention, the protein-binding RNA site is is an IRE, to which IRP-1 (iron regulatory protein) binds (see Muckenthaler M. et al., 1998, Molecular Cell 2:383–388).

A protein-binding RNA site may be obtained by any method known in the art including but not limited to automated synthesis, synthesis by PCR, and cloning from a cDNA library. A protein-binding RNA site may be identified by any method known in the art. In one embodiment, the site is identified by contacting an RNA containing a candidate protein-binding site with an RNA-binding protein. Following binding, the site is sequenced by methods known in the art. In another embodiment, an HBS may be identified by affinity purification methods. In a further embodiment, an RNA-binding protein is immobilized on a solid substrate and a source of RNA (e.g., total cellular RNA or poly(A) RNA, or random ribopolynucleotides is applied and allowed to bind to the RNA-binding protein. In an alternate embodiment, the HBS may be identified using a footprinting assay, or gel mobility shift assay.

One preferred method for detecting an RNA-binding protein comprises:(a) recombinantly expressing in a eukaryotic cell a fusion protein comprising an eIF4G-like protein or a translationally active derivative thereof fused to a test protein, wherein the cell comprises a DNA that is transcribed to produce a monocistronic or multicistronic RNA containing a heterologous protein-binding site in a region 5' and adjacent to a reporter gene coding region; and (b) detecting an increase in the amount of the protein encoded by said reporter gene coding sequence, relative to said amount produced in the absence of said test protein, wherein an increase in said amount indicates that the test protein is an RNA-binding protein that binds to said heterologous protein-binding site. In one embodiment the two or more identical heterologous protein-binding sites are in said intercistronic region.

Another preferred method for detecting a protein-binding site in an RNA comprises: (a) recombinantly producing in a eukaryotic cell: (i) a fusion protein comprising an eIF4G-like protein or a translationally active derivative thereof fused to a first protein for which it is desired to identify an RNA site to which said protein binds; (ii) a monocistronic or multicistronic RNA containing a heterologous test RNA sequence in a region 5' and adjacent to a reporter gene coding region; and (b) detecting an increase in the amount of the protein encoded by said reporter gene coding sequence relative to said amount produced in the absence of said RNA sequence, wherein an increase in said amount indicates that the test RNA sequence is a protein-binding site that binds to said first protein. In one embodiment said fusion protein is expressed from an expression vector.

Still another preferred method for detecting an RNA binding protein comprises: (a) recombinantly expressing within a population of eukaryotic cells a population of fusion proteins, each fusion protein comprising an eIF4G-like protein or a translationally active derivative thereof fused to a test protein, wherein the test protein varies among said population, wherein the cells comprise a DNA that is transcribed to produce a monocistronic or multicistronic RNA containing a heterologous protein-binding site in a region 5' and adjacent to a reporter gene coding region; and (b) identifying a cell within said population that displays an increase in the amount of the protein encoded by said reporter gene relative to said amount produced in the absence of said test protein or in the presence of other fusion proteins, thereby identifying a cell in which the test protein is an RNA-binding protein that binds to said heterologous protein-binding site. In one embodiment the test protein portion of said fusion proteins are encoded by nucleotide sequences of a cDNA library. In another embodiment the fusion proteins are produced from plasmid expression vectors under the control of an inducible promoter.

5.4. REPORTER GENES WITHIN A HETEROLOGOUS RNA

In one embodiment of the invention, the RNA molecule to be translated by the methods of the invention comprises a reporter gene coding region. Upon translational activation of the RNA molecule comprising said reporter sequence, the reporter sequence is translated into a protein which is detected as a read-out of the translational activation. In a preferred embodiment, the RNA to be translated is multicistronic and encodes two, three, four, ten, or more, or in the range of 1–5, 5–10, or 10–20 reporter sequences.

Thus, the reporter sequence comprises a nucleotide sequence operably linked to a protein-binding site (preferably HBS) for an RNA-binding protein. The activation of translation of the reporter coding region occurs intracellularly, in eukaryotic cells, preferably in cell culture.

In one embodiment, the reporter sequence comprises a coding region operably linked to one or more protein binding sites (preferably HBSs) that are specifically bound by an RNA binding domain of a fusion protein to an eIF4G-like protein or a derivative thereof that is employed in the methods of the invention, such that binding of the fusion protein to the one or more protein binding sites increases translation of the coding region under the control of the protein binding site. The protein binding site that is operably linked to the reporter sequence or other coding sequence-of-interest can be native or non-native (HBS) to the reporter sequence. Further, for example, one or more tandem copies (e.g., 2, 3, 4, 5, 1–5, 5–10, 10–20 or more copies) of the appropriate protein binding site can be introduced upstream of the reporter coding region.

The reporter coding region preferably encodes a protein (reporter protein) whose expression is easily detectable by methods, known in the art. For example, the reporter coding sequence may encode a detectable marker or selectable marker, facilitating detection of translational activation. Preferably, the assay is carried out in the absence of background levels of the reporter protein (e.g., in a cell that is mutant or otherwise lacking in the reporter protein). Preferably, more than one different reporter gene is used to detect translational activation, e.g., one reporter encoding a detectable marker, and one or more reporters encoding different selectable markers. The detectable marker can be any molecule that can give rise to a detectable signal, e.g., an enzyme or fluorescent protein. The selectable marker can be any molecule which can be selected for its expression, e.g., which gives cells a selective advantage over cells not having the selectable marker under appropriate (selective) conditions. In preferred aspects, the selectable marker is an essential nutrient in which the cell in which the interaction assay occurs is mutant or otherwise lacks or is deficient, and the selection medium lacks such nutrient. The reporter gene used need not be a gene containing a coding sequence containing a binding site for the RNA binding protein, but can alternatively be a chimeric gene containing a sequence that is translated under the control of a HBS that is not native to the translated sequence.

Reporter coding regions, comprising the functional coding sequences of reporter genes, including but not limited to, Green Fluorescent Protein (GFP) or mutants thereof (Cubitt et al., 1995, Trends Biochem. Sci. 20:448–455), a cell surface maker, luciferase, LEU2, LYS2, ADE2, TRP1, CAN1, CYH2, GUS, CUP1 (encoding metallothionein which confers resistance to copper) or chloramphenicol acetyl transferase (CAT) may be used, operatively linked to an HBS recognized by an RNA-binding protein of the invention being employed in the assay. LEU2, LYS2, ADE2 and TRP1 are selectable markers, i.e., their activity results in phototrophic growth in media lacking the nutrients encoded by these genes, while the activity of luciferase, GUS and CAT are preferably monitored enzymatically. Preferably, other genes such as CAN1 and CYH2 reporter genes are used to carry out negative selection in the presence of canavanine and cyloheximide, respectively. With respect to GFP, the natural fluorescence of the protein is detected, e.g., cells with GFP may be isolated using FACS sorting. In another embodiment, the expression of reporter proteins can be detected by immunoassay, i.e., by detecting the immunospecific binding of an antibody to such protein, which antibody can be labeled, or alternatively, which antibody can be incubated with a labeled binding partner to the antibody, so as to yield a detectable signal. Alam and Cook (1990, Anal. Biochem. 188:245–254) disclose non-limiting examples of detectable marker genes that can be used in the method of the invention as reporter genes.

The translational activation of reporter coding regions encoding selectable markers like URA3 or HIS3 of yeast, enables the cells to grow in the absence of uracil or histidine, respectively. Thus, the cells translating a selectable marker protein are selected by their abilities to grow in media lacking the requisite ingredient like uracil or histidine, respectively (referred to as –URA (minus URA) and –HIS medium, respectively). Alternatively to detecting URA3 gene activity by selecting in –URA medium, URA3 gene activity can be detected and/or measured by determining the activity of its gene product, orotidine-5'-monophosphate decarboxylase (Pierrat et al., 1992, Gene 119:237–245; Wolcott et al., 1966, Biochem. Biophys. Acta 122:532–534). In other embodiments of the invention, the activities of the reporter genes like lacZ or GFP are monitored by measuring a detectable signal (e.g., fluorescent or chromogenic) that results from the activation of these reporter genes. For example, lacZ translation can be monitored by incubation in the presence of a chromogenic substrate, such as X-gal (5-bromo-4-chloro-3-indolyl-β-D-galactoside), for its encoded enzyme, β-galactosidase.

5.5. PROTEIN DERIVATIVES AND ANALOGS

The invention further relates to the use of proteins and derivatives (including but not limited to fragments) of RNA-binding proteins and of eIF4G-like proteins.

The production and use of derivatives and related to eIF4G-like proteins or an RNA-binding protein are within the scope of the present invention. The derivatives for use in the present invention are functionally active, e.g., for eIF4G-like derivatives, they are translationally active (capable of exhibiting of ribosome recruitment, e.g., binding to eIF3), and for RNA-binding proteins, they retain the ability to bind to their cognate RNA sequence.

In particular, derivatives of an RNA-binding protein or an eIF4G-like protein can be made by altering the protein sequences by substitutions, additions (e.g., insertions) or deletions that provide for functionally equivalent molecules.

Due to the degeneracy of nucleotide coding sequences, other DNA sequences which encode substantially the same amino acid sequence the unaltered gene may be used in the practice of the present invention. These include but are not limited to nucleotide sequences comprising all or portions of a gene which is altered by the substitution of different codons that encode a functionally equivalent amino acid residue within the sequence, thus producing a silent change. Likewise, the RNA-binding protein/eIF4G-like protein fusion derivatives of the invention include, but are not limited to, those containing, as a primary amino acid sequence, all or part of the amino acid sequence of an RNA-binding protein and all or part of a functional eIF4G-like protein, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In a specific embodiment of the invention, fusion proteins comprising a fragment of a RNA-binding protein or a fragment of an eIF4G-like protein consist of at least 10 (continuous) amino acids of the protein. In other embodiments, the fragment consists of at least 20 or at least 50 or at least 107 or at least 200 amino acids of the protein. In specific embodiments, such fragments are not larger than 35, 100, 150, 200, 918, or 970 amino acids. Derivatives of proteins of the invention include but are not limited to those molecules comprising regions that are substantially homologous to an RNA-binding protein/eIF4G-like protein fusion protein or fragment thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a sequence encoding an RNA-binding protein/eIF4G-like protein fusion protein, under high stringency, moderate stringency, or low stringency conditions (See Section 5.14).

Specifically, by way of example computer programs for determining homology may include but are not limited to TBLASTN, BLASTP, FASTA, TFASTA, and CLUSTALW (Pearson and Lipman, 1988, Proc. Natl. Acad. Sci. USA 85(8):2444–8; Altschul et al., 1990, J. Mol. Biol. 215(3):403–10; Thompson, et al., 1994, Nucleic Acids Res. 22(22):4673–80; Higgins, et al., 1996, Methods Enzymol 266:383–402; Altschul, et al., 1990, J. Mol. Biol. 215(3):403–10).

Smith-Waterman (database: European Bioinformatics Institute wwwz.ebi.ac.uk/bic_sw/) (Smith-Waterman, 1981, J. of Molec. Biol., 147:195–197) is a mathematically rigorous algorithm for sequence alignments.

FASTA (see Pearson et al., 1988, Proc. Nat'l Acad. Sci. USA, 85:2444–2448) is a heuristic approximation to the Smith-Waterman algorithm. For a general discussion of the procedure and benefits of the BLAST, Smith-Waterman and FASTA algorithms see Nicholas et al., 1998, "A Tutorial on Searching Sequence Databases and Sequence Scoring Methods" (www.psc.edu) and references cited therein.

The derivatives of the invention can be produced by various methods known in the art. The manipulations which result in their production can occur at the gene or protein level. For example, a sequence encoding an eIF4G/RNA-binding protein can be modified by any of numerous strategies known in the art (Sambrook et al., 1989, Molecular Cloning, A Laboratory Manual, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of a modified gene encoding a derivative or analog of an eIF4G/RNA-binding protein, care should be taken to ensure that the modified gene remains within the same translational reading frame as the native protein, uninterrupted by translational stop signals, in the gene region where the desired RNA-binding protein or eIF4G protein activity is encoded.

Additionally, a nucleic acid sequence encoding an eIF4G/RNA-binding protein can be mutated in vitro or in vivo, or to create variations in coding regions and/or to form new restriction. Any technique for mutagenesis known in the art can be used, including but not limited to, chemical mutagenesis, in vitro site-directed mutagenesis (Hutchinson et al., 1978, J. Biol. Chem. 253:6551), use of TAB® linkers (Pharmacia), PCR with primers containing a mutation, etc.

Manipulations of an eIF4G/RNA-binding protein sequence may also be made, although less preferably, at the protein level (after which the derivative is introduced into a cell for use according to the present invention). Included within the scope of the invention are RNA-binding protein/eIF4G-like protein fusions, fragments, or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage, NaBH4, acetylation, formylation, oxidation, reduction, metabolic synthesis in the presence of tunicamycin, etc.

In addition, derivatives of an RNA-binding protein/eIF4G-like protein fusion can be chemically synthesized. For example, a peptide corresponding to a portion of an RNA-binding protein and/ or the eIF4G-like protein which comprises the desired domain, or which mediates the desired activity in vitro, can be synthesized by use of a peptide synthesizer. Furthermore, if desired, nonclassical amino acids or chemical amino acid analogs can be introduced as a substitution or addition into the sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In specific embodiments, the fusion proteins of the invention comprise an eIF4G-like protein or a derivative thereof, or an RNA-binding protein, joined at its amino- or carboxy-terminus via a peptide bond to an amino acid sequence of a different protein (see infra). In specific embodiments, the amino acid sequence of the different protein is at least 6, 10, 20 or 30 continuous amino acids of the different proteins or a portion of the different protein. In a preferred embodiment, such a chimeric protein is produced intracellularly by recombinant expression of a nucleic acid encoding the protein (e.g., comprising an eIF4G-like coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer, and introduced into the cell. Chimeric genes comprising portions of a nucleic acid encoding an eIF4G-like or RNA-binding protein fused to any heterologous protein-encoding sequences may be constructed. Fusions may be at the amino- or carboxy- teminus.

5.6. THERAPEUTIC CODING REGIONS-OF-INTEREST FOR TRANSLATION BY AN eIF4G SYSTEM AND THERAPEUTIC USES

In this embodiment, the protein(s) which are produced by translation from multicistronic RNA of the invention have therapeutic utility. For example, the protein may alleviate symptoms of a disease or disorder, or provide function lacking due to a genetic disorder or may be toxic to an infectious disease agent. Gene therapy refers to the transfer of new genetic information into cells for the therapeutic treatment of diseases or disorders. The foreign gene is transferred into a cell that proliferates to spread the new gene throughout the cell population. Thus stem cells, or pluripotent progenitor cells, are usually the target of gene transfer, since they are proliferative cells that produce various progeny lineages which will potentially express the foreign gene.

The methods of the present invention provide ways of increasing recombinant protein production in the target cells for gene therapy. The invention also provides a way for delivering multiple proteins within a cell with a specific stoichiometry. Further, the invention provides a system of producing multiple subunit proteins within a cell.

The methods of the invention are useful for the treatment of genetic disorders. The methods of the invention are also useful for the treatment of disorders involving the mis-expression (e.g., decreased expression or increased expression) of a protein. Further, the methods of the invention are also useful for the treatment of a disorders involving one or more mutated proteins. Additionally, the methods of the invention are useful for the treatment of disorders relating to activated proteins. Such disorders which may be treated by the methods of the invention include but are not limited to the following:

Hereditary diseases such as cystic fibrosis, Tay-Sachs disease, sickle cell anemia, hemophilia, atherosclerosis, diabetes, and obesity. Such hereditary diseases may include degenerative and non-degenerative neurological diseases such as Alzheimer's disease, Parkinson's disease, amyotrophic lateral sclerosis, Huntington's disease, spinal cerebellar ataxia, Friedreich's ataxia, prion disease, dentatorubral pallidoluysian atrophy, depression, schizophrenia, and epilepsy. Hereditary diseases may also include metabolic diseases such as, for example, hypoglycemia or phenylketonuria. Cardiovascular diseases and conditions are also included, non-limiting examples of which include atherosclerosis, myocardial infarction, and high blood pressure.

Cancers and hypoproliferative diseases that may be treated by the methods of the invention include, but not are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In accordance with the methods described herein, the methods of the invention may be used for the treatment of viral and infectious diseases including, but not limited to, hepatitis type A, hepatitis type B, hepatitis type C, influenza, varicella, adenovirus, HSV-I, HSV-II, rinderpest rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, HIV-I, and HIV-II. Furthermore, the methods of the invention may be used for the detection of intracellular parasites including, but not limited to, Chlamydia and Rickettsia.

The methods of the invention can be further be used or in connection with the treatment of disorders, including but not limited to allergies, drug resistance, psoriasis, tuberculosis, Lyme disease, autoimmune disorders, and sexually transmitted diseases.

It is appreciated, however, that the methods described herein will be useful in treating diseases of humans as well as other mammals, for example, farm animals including: cattle; horses; sheep; goats; and pigs; household pets including cats and dogs. The methods described herein will also be useful in treating diseases of plants, including agriculturally important plants, flowering plants, crop plants, and medically important plants.

Thus, coding regions encoding proteins therapeutic for the above-mentioned disorders are examples of coding regions-of-interest that may be used in the construction of a nucleic acid encoding a RNA of the invention to be translated.

In a particularly useful aspect of the invention, the methods of eIF4G-like driven translational activation of the invention may be combined with methods known in the art relating to gene therapy. In this way, translation of genes used in gene therapy is increased.

In a preferred aspect, nucleic acids encoding the multicistronic RNA and fusion protein(s) used for translation of the desired protein(s) are introduced directly into the organism to the treated, or alternatively are introduced into cells ex vivo, which cells are then introduced into the organism, such that the RNA and fusion protein(s) are produced intracellularly, activating translation.

The nucleic acid(s) can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

In a specific embodiment, the translation of a dominant negative mutant protein is used for the treatment of disease or disorders which are associated with over-expression or activated forms of a protein (e.g., activated kinases that contribute to hypoproliferative disorders or cancer).

5.7. RECONSTITUTING A TRANSLATIONAL ACTIVATOR AND DETECTION OF PROTEIN—PROTEIN INTERACTIONS

This invention provides methods for detecting protein—protein interactions by reconstituting a translational activator. As described in Section 5.5, a fusion protein of an eIF4G-like protein, or a translationally active derivative thereof, and an RNA-binding protein ("RNA-binding protein/eIF4G-like protein fusion") that is capable of binding to an HBS, is capable of activating translation by bringing the ribosome recruitment protein eIF4G-like protein into proximity with an HBS within an RNA molecule to be translated. The RNA-binding protein/eIF4G-like protein fusion protein thus serves as a translational activator.

The invention further provides a method to reconstitute a translational activator and to detect protein—protein interactions. To this end, two separate fusion proteins are constructed and used to reconstitute the translational activator.

The first fusion protein comprises an RNA-binding protein or portion thereof which is capable of binding an HBS fused to a first test protein or portion thereof, wherein the test protein is to be tested for interaction with a second test protein.

The second fusion protein comprises an eIF4G-like protein or translationally active protein derivative thereof, fused to a second test protein, which is to be tested for interaction with the first test protein.

Interaction between the first test protein and the second test protein, brings into proximity the eIF4G-like protein and the RNA-binding protein, and therefore reconstitutes the translational activator. Reconstitution of the translational activator thus leads to translation of the adjacent gene(s) downstream (3') of the HBS.

The method is carried out by introducing the RNA-binding fusion protein and the eIF4G-like fusion protein into a host cell, or, preferably, by recombinantly expressing the same within a host cell. The host cell is subjected to conditions under which the first hybrid protein and the second hybrid protein are expressed in sufficient quantity for the detectable gene to be activated. The cells are then tested for their expression of the detectable gene to a greater degree than in the absence of the test proteins.

Thus, interactions between a first test protein and a library of proteins can be tested. For example, the first test protein may be derived from a bacterial protein, a viral protein, an oncogene-encoded protein, a growth factor or an enzyme. The second test protein may be derived from a library of plasmids as described above.

In a specific embodiment the invention provides a method for detecting binding between a first test protein and a second test protein comprising (a) recombinantly expressing in a eukaryotic cell (a) a first fusion protein comprising an eIF4G-like protein or a translationally active derivative thereof, fused to a first test protein; and (ii) a second fusion protein comprising an RNA-binding protein fused to a second test protein; wherein the cell comprises a DNA that is transcribed to produce a monocistronic or multicistronic RNA containing a heterologous protein-binding site in a region 5' and adjacent to a reporting gene coding region, wherein said RNA-binding protein binds to said heterologus protein-binding site; and (b) detecting an increase in the amount of the protein encoded by said reporter gene coding region relative to said amount produced in the absence of one or both test proteins, wherein an increase in said amount indicates that the first test protein binds to said second test protein.

5.8. METHODS FOR DETECTING RNA-BINDING PROTEINS

In a specific embodiment, the invention provides methods for identifying a protein which binds to a protein-binding RNA site of interest. In this embodiment, the following assay materials are provided (preferably by recombinant production within a host cell):

(1) one or more fusion proteins, each comprising an eIF4G-like protein or a translationally active derivative thereof fused to a test protein.

(2) a monocistronic or multicistronic RNA containing an HBS in a region 5' to a reporter gene coding region (e.g., CAT, GFP), wherein the HBS is one for which it is desired to identify a binding protein.

Preferably (1) above is a population of such fusion proteins in which an eIF4G-like protein (or a translationally active derivative thereof) is fused to a plurality of different sequences of a library (e.g., a cDNA library or random or biased peptide expression library), each fusion protein or a pool thereof being expressed in different host cell in which the multicistronic RNA is produced. Thus, one or more of the fusion proteins are produced in a cell in the presence of the multicistronic RNA. The reporter gene coding region will be translated (or translated at increased levels) in a cell in which the cDNA portion of the fusion protein encodes a binding protein that binds the HBS. Thus, identification of a cell in which increased translation of the reporter gene product occurs identifies a cell containing a cDNA encoding such a binding protein. The cDNA can then be recovered from the identified cell.

Host cells and selection conditions that may be employed in such method are known in the art and/or are described in Section 5.9 and 5.2.

5.9. DETECTING INTERACTING PROTEINS

The present invention also provides methods for detecting interacting proteins (including peptides and polypeptides). Interacting proteins are detected based on the reconstitution of a translationally active system that causes translation of a reporter gene coding region. In this embodiment, the following assay materials are provided (preferably by recombinant production in a host cell):

(1) one or more first fusion proteins, each comprising an eIF4G-like or a translationally active derivative thereof fused to a first test protein.

(2) one or more second fusion proteins, each comprising an RNA-binding protein fused to a second test protein.

(3) a monocistronic or multicistronic RNA containing an HBS in a regions 5' to an adjacent reporter gene coding region, wherein the HBS and the RNA binding protein are known to bind to each other.

Expression of (1), (2) and (3) above within a cell will cause increased translation of the reporter coding region only where the first test protein and the second test protein bind to each other, thus bringing the eIF4G-like protein into proximity with the HBS. Thus, identifying a cell of such increased translation identifies a cell in which the first and second test proteins have interacted.

In a first specific embodiment, the first test protein and the second test protein are individual proteins of interest, for which it is desired to test whether interaction between the two occurs.

In a second specific embodiment, either of the first or second fusion protein above is a population of such fusion proteins in which the test protein is a plurality of different sequences of a library (e.g., cDNA library or random or biased peptide expression library), each fusion protein or a pool thereof being expressed in a different host cell in the presence of the other fusion protein and the intercistronic mRNA. Thus, for example, where the first test protein is a particular protein of interest, and the second fusion proteins comprise a library, a cell in which increased translation of the reporter protein occurs will contain a second fusion protein comprising a protein sequence that binds to the particular protein of interest, thus identifying a protein that binds to a protein of interest. Alternatively, the method can be performed wherein the second test protein can be a particular protein of interest, and the first fusion proteins comprise a library.

In a third specific embodiment, both the first test proteins and the second test proteins, of the first and second fusion proteins, respectively, are a plurality of different sequences of a library.

In a specific embodiment, the invention provides a preferred method of detecting one or more protein—protein binding interactions comprising: (a) recombinantly expressing within a population of eukaryotic cells (i) first population of first fusion proteins comprising an eIF4G-like protein or a translationally active derivative thereof fused to a first test protein, wherein the first test protein varies among the population, (ii) a second population of second fusion proteins comprising an RNA-binding protein fused to a second test protein, wherein the second test protein varies among the population; wherein the cell comprises a DNA that is transcribed to produce a monocistronic or multicistronic RNA containing a heterologous protein-binding site in a region 5' and adjacent to a reporter gene coding region, wherein said RNA-binding protein binds to said heterologous protein-binding site; and (b) detecting a cell that exhibits an increase in the amount of the protein encoded by said reporter gene coding region relative to said amount produced in the absence of one or both test proteins or relative to other cells in the population, wherein said increase indicates that the first and second test proteins in said cell bind to each other.

Protein-protein interactions can be detected, and the interacting pairs of proteins isolated and identified, between two populations of proteins wherein both of the populations have a complexity of at least 10 (i.e., both populations contain more than ten distinct proteins). The populations are expressed as test proteins and are fused to an RNA-binding protein, and to an eIF4G-like protein or derivative, respectively. In various specific embodiments, one or both of the populations of proteins has a complexity of at least 50, 100, 500, 1,000, 5,000, 10,000, or 50,000; or has a complexity in the range of 25 to 100,000, 100 to 100,000, 50,000 to 100,000, or 10,000 to 500,000. For example, one or both populations can be mammalian cDNA populations, generally having a complexity in the range of 50,000 to 100,000. In a specific embodiment, the two populations are samples (aliquots) of at least 100 or 1000 members (e.g., expressed in host yeast cells) of a larger population (e.g., a mammalian cDNA library) having a complexity of at least 100, 1000, 5,000, 10,000, or 50,000; in a particular embodiment, the sample is uncharacterized in that the particular identities of all or most of its member proteins are not known.

The populations can be the same or different populations. If it is desired to detect interactions between test proteins encoded by a particular DNA population, both test protein populations are expressed from chimeric genes comprising DNA sequences representative of that particular DNA population. In a specific embodiment, one or more of the populations can be uncharacterized in that the identities of all or most of the members of the population are not known. Preferably, the populations are proteins encoded by DNA, e.g., cDNA or genomic DNA or synthetically generated DNA. For example, the populations can be expressed from chimeric genes comprising cDNA sequences from an uncharacterized sample of a population of cDNA from mammalian RNA. Preferably, a cDNA library is used. The cDNA can be, e.g., a normalized or subtracted cDNA population. The cDNA of one or both populations can be cDNA of total mRNA or polyA$^+$ RNA or a subset thereof from a particular species, particular cell type, particular age of individual, particular tissue type, disease state or disorder or stage thereof, or stage of development. Alternatively, the population are proteins or analogs thereof, encoded by diversity libraries, e.g., random or biased peptide libraries.

Preferably, the populations of test proteins between which interactions are detected are provided by recombinant expression of nucleic acid populations (e.g., cDNA or genomic libraries). Also preferably, the interactions occur intracellularly. In another specific embodiment, recombinant biological libraries expressing random peptides can be used as the source nucleic acid for one or both of the nucleic acid populations.

In a preferred aspect, the present invention provides a method for detecting unique protein—protein interactions that characterize a population or library of proteins by comparing detectable protein—protein interactions that occur in a population or library with those interactions that occur in another population or library. Furthermore, the method also enables the identification of inhibitors or enhancers of such protein—protein interactions.

Protein-protein interactions are detected according to the invention by detecting translational activation which occurs upon interaction of proteins between the two populations being tested. Proteins of each population are provided as fusion (chimeric) proteins (preferably by recombinant expression of a chimeric coding sequence) containing each protein contiguous to a preselected sequence. For one population, the preselected sequence is an RNA-binding protein. For the other population, the preselected sequence is an eIF4G-like protein or translationally active derivative thereof.

In a preferred embodiment, each test protein in one population is provided as a fusion to a RNA-binding domain. Each protein in the other population is provided as a fusion to an eIF4G-like protein or a translationally active domain or other derivative thereof. The RNA-binding domain alone (not as a first test protein sequence) and the eIF4G-like domain alone (not as a fusion to a protein second test sequence) preferably do not detectably interact (so as to avoid false positives in the assay). When binding occurs of a first test to a second test protein, translation increases/ occurs of a reporter coding region that is operably linked to a protein-binding RNA site (preferably on HBS) bound by the RNA-binding domain of the translational activator. The activation of transcription of the reporter gene occurs intracellularly, e.g., in eukaryotic cells, preferably in cell culture.

In a specific embodiment, one or more tandem copies (e.g., 2, 3, 4, 5 or more copies) of the appropriate HBS are upstream of the reporter coding region.

The reporter gene for the detection of translational activation preferably comprises a nucleotide sequence, whose translation is regulated by the translational activator, that is a coding sequence that encodes a detectable marker or selectable marker, facilitating detection of translational activation, thereby detecting a protein—protein interaction, and can be any of those described above or known in the art. Preferably, the assay is carried out in the absence of background levels translation of the reporter coding sequence. In a specific embodiment, more than one different reporter coding regions are used to detect translational activation, e.g., one encoding a detectable marker, and one or more encoding different selectable markers, each with an RNA-binding site in the adjacent upstream region. The detectable marker can be any molecule that can give rise to a detectable signal, e.g., an enzyme or fluorescent protein. The selectable marker can be any molecule which can be selected for its expression, e.g., which gives cells a selective advantage over cells not having the selectable marker under appropriate (selective) conditions. In preferred aspects, the selectable marker is an essential nutrient in which the cell in which the interaction assay occurs is mutant or otherwise lacks or is deficient, and the selection medium lacks such nutrient. The reporter gene used need not be a gene containing a coding sequence whose native promoter contains a binding site for the RNA binding protein, but can alternatively, and preferably, be a chimeric gene containing a sequence that is translated under the control of an HBS that is not the native to the translated sequence.

In a specific embodiment, to make the fusion constructs (encoding the fusion proteins such that the fusion proteins are expressed in the desired host cell) from each population (e.g., library), an RNA binding domain of any RNA binding protein which is capable of binding the HBS of the RNA can be used to construct a fusion protein.

In another embodiment, the fusion constructs further comprise sequences encoding affinity tags such as glutathione-S-transferase or maltose-binding protein or an epitope of an available antibody, so as to facilitate isolation of the encoded proteins by affinity methods (e.g., binding to glutathione, maltose, or antibody, respectively) (see Allen et al., 1995, *TIBS* 20:511–516). In another embodiment, the fusion constructs further comprise bacterial promoter sequences operably linked to the fusion coding sequences to facilitate the production of the fusion proteins also in bacterial cells (see Allen et al., 1995, *TIBS* 20:511–516).

The host cell in which the interaction assay occurs can be any eukaryotic cell in which translation of the reporter coding region can occur and be detected, including but not limited to mammalian (e.g., monkey, chicken, mouse, rat, human, bovine), worm cells, insect cells, fungal cells, plant cells, and yeast cells. In one embodiment, expression constructs encoding and capable of expressing the RNA-binding domain fusion proteins, the eIF4G-like protein fusion proteins, and the reporter gene product(s) are provided within the host cell, by mating of cells containing the expression constructs, or by cell fusion, transformation, electroporation, microinjection, etc. In a specific embodiment in which the assay is carried out in mammalian cells (e.g., HeLa cells), the RNA-binding domain is the IRP-1 (Iron Responsive Protein-1), the eIF4G-like protein is amino acids 642–1560 of human eIF4G1 and the reporter gene is CAT (Chloramphenicol Acetyl Transferase). As will be apparent, other RNA binding domains, eIF4G-like protein, and/or reporter genes can be used, as long as the RNA protein-binding sites are recognized by the RNA-binding domains of the protein. The host cell used should preferably not express an endogenous translation factor that binds to the same RNA site as that recognized by the RNA-binding domain fusion population. Also, preferably, the host cell is mutant or otherwise lacking an endogenous, functional form of the reporter coding region used in the assay.

Preferably, the protein—protein interactions are assayed according to the method of the invention in mammalian cells. In another embodiment, the protein—protein interactions are assayed according to the methods of the invention in yeast cells, e.g., *Saccharomyces cerevisiae* or *Schizosaccharomyces*. Various vectors for producing the two fusion protein populations and host strains for conducting the assay are known and can be used (see, e.g., Fields et al., U.S. Pat. No. 5,468,614 dated Nov. 21, 1995; Bartel et al., 1993, "Using the two-hybrid system to detect protein—protein interactions," in *Cellular Interactions in Development,* Hartley, D. A. (ed.), Practical Approach Series xviii, IRL Press at Oxford University Press, New York, N.Y., pp. 153–179; Fields and Sternglanz, 1994, TIG 10:286–292). Exemplary strains that can be modified to create reporter strains (containing the desired reporter gene for use in the assay of the invention) also include the following (see PCT Publication WO 97/47763 published Dec. 18, 1997):

Y190: MATa, ura3-52, his3-200, lys2-801, ade2-101, trp1-901, leu2-3,112, gal4Δ, gal80Δ, cyh$^r$2, LYS2::GAL1$_{UAS}$-HIS3$_{TATA}$-HIS3, URA3::GAL1$_{UAS}$-GAL1$_{TATA}$-lacZ (available from Clontech, Palo Alto, Calif.; Harper et al., 1993, Cell 75:805–816). Y190 contains HIS3 and lacZ reporter genes driven by GAL4 binding sites.

CG-1945: MATa, ura3-52, his3-200, lys2-801, ade2-101, trp1-901, leu2-3,112, gal4-542, gal80-538, cyh$^r$2, LYS2::GAL1$_{UAS}$-GAL1$_{TATA}$-HIS3, URA3::GAL1$_{UAS\ 17\ mers\ (x3)}$-CYC1$_{TATA}$-lacZ(available from Clontech). CG-1945 contains HIS3 and lacZ reporter genes driven by GAL4 binding sites.

Y187: MATα, ura3-52, his3-200, ade2-101, trp1-901, leu2-3,112, gal4Δ, gal80Δ, URA3::GAL1$_{UAS}$-GAL1$_{TATA}$-lacZ (available from Clontech). Y187 contains a lacZ reporter gene driven by GAL4 binding sites.

SFY526: MATa, ura3-52, his3-200, lys2-801, ade2-101, trp1-901, leu2-3,112, gal4-542, gal80-538, can$^r$, URA3::GAL1-lacz (available from Clontech). SFY526 contains HIS3 and lacZ reporter genes driven by GAL4 binding sites.

HF7c: MATa, ura3-52, his3-200, lys2-801, ade2-101, trp1-901, leu2-3,112, gal4–542, gal80-538, LYS2::GAL1-HIS3, URA3::GAL1$_{UAS\ 17\ MERS\ (x3)}$-CYC1-lacZ (available from Clontech). HF7c contains HIS3 and lacZ reporter genes driven by GAL4 binding sites.

YRG-2: MATα, ura3-52, his3-200, lys2-801, ade2-101, trp1-901, leu2-3,112, gal4-542, gal80-538, LYS2::GAL1$_{UAS}$-GAL1$_{TATA}$-HIS3, URA3::GAL1$_{UAS\ 17\ mers\ (x3)}$-CYC1-lacZ (available from Stratagene). YRG-2 contains HIS3 and lacZ reporter genes driven by GAL4 binding sites.

Many other strains commonly known and available in the art can be used.

Consistent with convention in the art, wild-type gene names listed above are all capitalized and italicized; mutant gene names are lower case and italicized—except for lacZ for which the functional, non-mutant gene is written lower case, italicized.

If not already lacking in endogenous reporter gene activity, cells mutant in the reporter gene may be selected by known methods, or the cells can be made mutant in the target reporter gene by known gene-disruption methods prior to introducing the reporter gene (Rothstein, 1983, Meth. Enzymol. 101:202–211).

In a specific embodiment, plasmids encoding the different fusion protein populations, as well as a plasmid encoding the RNA to be translated, can be introduced into a single host cell, by cotransformation, to conduct the assay for protein—protein interactions. As a preferred alternative to cotransformation of expression constructs, mating (e.g., of yeast cells) or cell fusion (e.g., of mammalian cells) can be employed for delivery of an RNA-binding domain fusion expression construct and an eIF4G-like protein fusion expression construct into a single cell. For example, in a mating-type assay, conjugation of haploid yeast cells of opposite mating type that have been transformed with an RNA-binding domain fusion expression construct (preferably a plasmid) and an eIF4G-like domain fusion expression construct (preferably a plasmid), respectively, delivers both constructs into the same diploid cell. The mating type of a strain may be manipulated as desired, by transformation with the HO gene (Herskowitz and Jensen, 1991, Meth. Enzymol. 194:132–146).

In an alternate embodiment, a yeast interaction mating assay is employed, using two different types of host cells, strain-types a and α, of the yeast *Saccharomyces cerevisiae*. The host cell preferably contains at least two reporter genes, containing a binding site for the RNA-binding domain (e.g., of a translational activator), such that the reporter gene is translationally activated when the RNA-binding domain is in proximity to an eIF4G-like domain of a translational activator. The eIF4G-like domain and RNA binding domain are each parts of chimeric proteins formed from the two respective populations of proteins.

In yet another embodiment of the invention, alternatively to plasmids, bacteriophage vectors such as λ vectors are used as the fusion protein vectors to make, e.g., the respective cDNA libraries. The use of λ vectors generally makes it faster and easier to generate such libraries than with the use of plasmid vectors.

In a specific embodiment of the invention, false positives arising from activation by the RNA-binding fusion proteins in the absence of an eIF4G-like fusion protein are prevented or reduced by negative selection for such activation within a host cell containing the RNA binding fusion protein, prior to exposure to the eIF4G-like fusion protein (see PCT Publication WO 97/47763 dated Dec. 18, 1997). By way of example, if such cell contains URA3 as a reporter gene, negative selection is carried out by incubating the cell in the presence of 5-fluoroorotic acid (5-FOA, which kills URA+ cells (Rothstein, 1983, Meth. Enzymol. 101:167–180). In yet another embodiment, negative selection can be carried out by plating the RNA-binding fusion proteins on medium selective for interaction (e.g., minus URA or minus HIS medium if the reporter gene is URA3 or HIS3, respectively), following which all the surviving colonies are physically removed and discarded.

As will be apparent, negative selection can also be carried out on the eIF4G fusion protein prior to interaction with the RNA binding domain fusion protein, by similar methods, alone or in addition to negative selection of the RNA-binding fusion proteins.

In another embodiment, negative selection can also be carried out on the recovered pairs of protein interactants, by known methods (see, e.g., Bartel et al., 1993, BioTechniques 14(6):920–924) although pre-negative selection (prior to the interaction assay), as described above, is preferred. For example, each plasmid encoding a first test protein (peptide or polypeptide) fused to the RNA-binding domain (one-half of a detected interacting pair) can be transformed back into the original screening strain, either without any other plasmid, or with a plasmid encoding only the eIF4G-like protein, the RNA-binding domain fusion to the detected interacting test protein (the second half of the detected interacting pair), or the eIF4G-like domain fusion to an irrelevant protein; a positive interaction detected with any plasmid other than that encoding the eIF4G-like domain fusion to the detected interacting protein is deemed a false positive and eliminated from further use.

In a preferred embodiment of the invention, after an interactive population is obtained, the DNA sequences encoding the pairs of interactive proteins are isolated by a method wherein either the RNA-binding protein fusions or the eIF4G-like protein fusions are amplified. Preferably, both the RNA-binding fusion sequences and the eIF4G-like protein fusion sequences are amplified, in separate respective reactions. Preferably, the amplification is carried out by polymerase chain reaction (PCR) (U.S. Pat. Nos. 4,683,202. 4,683,195 and 4,889,818; Gyllenstein et al., 1988, Proc. Natl.

Acad. Sci. USA 85:7652–7656; Ochman et al., 1988, Genetics 120:621–623; Loh et al., 1989, Science 243:217–220; Innis et al., 1990, PCR Protocols, Academic Press, Inc., San Diego, Calif.), using pairs of oligonucleotide primers that are specific to either the nucleic acids encoding the RNA-binding protein fusions or the eIF4G-like protein fusion in the PCR reaction. Other amplification methods known in the art can be used, including but not limited to ligase chain reaction (see EP 320,308) use of Qβ replicase, or methods listed in Kricka et al., 1995, Molecular Probing, Blotting, and Sequencing, chap. 1 and table IX, Academic Press, New York.

5.10. ISOLATION OF INHIBITORS, ENHANCERS, OR FACILITATORS OF PROTEIN INTERACTIONS

The present invention also provides methods for identifying inhibitors or enhancers or facilitators of protein—protein interactions. As described in Section 5.7, supra, interactions between two test proteins may be identified by the reconstitution of a translational activator. Thus, once two proteins are identified as interacting (by the methods of the invention or otherwise) the inhibition or facilitation of this interaction may be detected as described herein. The present invention is particularly valuable in that it enables one to identify not only the interacting proteins that are unique but also enables the identification of inhibitors or enhancers or facilitators of such interactions. The invention provides methods of identifying a candidate molecule that acts as an inhibitor, enhancer, or facilitator of an interaction. The candidate molecules can be provided to the cell either by recombinant expression or by addition of the molecule itself to the cell. Thus, for example, as an example of the latter embodiment, the cells can be cultured in medium containing the recombinant molecule.

The invention provides a method for identifying a molecule that complexes together a first protein and a second protein comprising: (a) recombinantly expressing in a eukaryotic cell in the presence of a candidate molecule (i) a first fusion protein comprising an eIF4G-like protein or a translationally active derivative thereof, fused to a first protein, and (ii) a second fusion protein comprising an RNA-binding protein, fused to a second protein, wherein the first and second proteins do not bind to each other; wherein the cell comprises a DNA that is transcribed to produce a monocistronic or multicistronic RNA containing a heterologous protein-binding site in a region 5' and adjacent to a reporter gene coding region, wherein said RNA-binding protein binds to said heterologous protein-binding site; and (b) detecting an increase in the amount of the protein encoded by said reporter gene coding region relative to said amount produced in the absence of said candidate molecule, wherein said increase indicates that the candidate molecule complexes together said first protein and said second protein. In a specific embodiment, the candidate molecule is also recombinantly expressed in the cell.

The invention further provides for a the method above wherein the candidate molecule is a candidate inhibitor molecule, and a decrease is detected in step (b), thereby indicating that the candidate molecule inhibits the binding of said first protein to said second protein.

The invention further provides a preferred method for identifying a molecule that affects the amount of binding between a first protein and a second protein comprising: (a) recombinantly expressing in a eukaryotic cell n the presence of a candidate molecule (i) a first fusion protein comprising an eIF4G-like protein or a translationally active derivative thereof, fused to a first protein; and (ii) a second fusion protein comprising an RNA-binding protein fused to a second protein, wherein the first and second proteins bind to each other; wherein the cell comprises a DNA that is transcribed to produce a monocistronic or multicistronic RNA containing a heterologous protein-binding site in a region 5' and adjacent to a reporter gene coding region, and wherein said RNA-binding protein binds to said heterologous protein-binding site; and (b) detecting an increase or decrease in the amount of the protein encoded by said reporter gene coding region relative to said amount produced in the absence of the candidate molecule, wherein said increase or decrease indicates that the candidate molecule inhibits or increases binding of said first protein to said second protein. In a specific embodiment, the candidate molecule is also recombinantly expressed in the cell.

The invention also provides a preferred method for identifying a molecule that complexes together a first protein and a second protein comprising: (a) recombinantly expressing in a eukaryotic cell (i) a first fusion protein comprising an eIF4G-like protein or a translationally active derivative thereof, fused to a first protein, (ii) a second fusion protein comprising an RNA-binding protein, fused to a second protein, wherein the first and second proteins do not bind to each other, and (iii) a candidate molecule; wherein the cell comprises a DNA that is transcribed to produce a monocistronic or multicistronic RNA containing a heterologous protein-binding site in a region 5' and adjacent to a reporter gene coding region, wherein said RNA-binding protein binds to said heterologous protein-binding site; and (b) detecting an increase in the amount of the protein encoded by said reporter gene coding region relative to said amount produced in the absence of said candidate molecule, wherein said increase indicates that the candidate molecule complexes together said first protein and said second protein. In one embodiment the candidate molecule is a candidate inhibitor molecule, and a decrease is detected in step (b), thereby indicating that the candidate molecule inhibits the binding of said first protein to said second protein. In another embodiment an increase is detected in step (b), thereby indicating that the candidate molecule increases the binding of said first protein to said second protein. In another embodiment step (a) comprises recombinantly expressing in a population of said cells a population of said first fusion proteins, wherein said first test protein varies among said population. In a further embodiment, said first test protein portions of said first fusion proteins are encoded by nucleotide sequences of a cDNA library. In another embodiment, step (a) comprises recombinantly expressing in a population of said cells a population of said second fusion proteins, wherein said second test protein varies among said population. In a further embodiment, said second test protein portions of said second fusion proteins are encoded by nucleotide sequences of a cDNA library. In still other embodiments step (a) comprises recombinantly expressing in a population of said cells a plurality of different said candidate molecules. In a further embodiment the method comprises isolating a nucleic acid encoding said first test protein from a cell in which said increase is detected in step (b).

In a specific embodiment, an assay for the presence of an interacting protein pair is carried out as described in the sections supra, except that it is done in the presence of one or more candidate molecules which it is desired to screen for the ability to increase or decrease an interaction between a protein—protein pair that results in translation from the reporter gene. An increase or decrease in reporter gene activity relative to that present when the one or more candidate molecules are absent indicates that the candidate molecule has an effect on the interacting pair. For example, a decrease in (e.g., absence of) reporter gene activity that would otherwise occur in the absence of a candidate molecule, due to the presence of an interacting pair, indicates that the candidate molecule is an inhibitor of the interaction exhibited by the protein pair. In a specific embodiment, in which the host cell is a yeast cell, selection of positive interactants (colonies) is carried out; these colonies are exposed to candidate inhibitor molecule(s) and are selected again, this time for lack of interaction (e.g., by selection for survival in medium containing 5-FOA wherein URA3 is a reporter gene, or by selection for survival in medium containing α-amino-adipate wherein LYS2 is a reporter gene, or the other methods of negative selection described herein; selection of cells that do not display a signal generated by a reporter gene (e.g., in the case of lacZ, by activity on the β-gal substrate X-gal (5-bromo-4-chloro-3-indolyl- β-D-galactoside)). The environment in which selection is carried out preferably also selects for the presence of the recombinant nucleic acids encoding the interacting pair of proteins. Thus, for example, the proteins are expressed from plasmids also expressing a selectable marker, thus facilitating this selection.

In an alternative embodiment, the invention provides methods for identifying a protein which complexes with two other proteins, thus bringing the two other proteins into proximity with each other and reconstituting a translationally active system of the invention. In this embodiment, the method is carried out as described above for identifying an inhibitor of a protein—protein interaction, except that instead of the first and second interacting proteins, a first and second test protein that do not interact are employed in the respective fusion proteins, and the candidate inhibitor molecule is instead a candidate complexing molecule that binds to both the first and second test proteins, thus bring the first and second proteins into proximity, and activating translation of the adjacent reporter coding region downstream of the HBS. Cells containing such a candidate complexing molecule are identified by detecting increased translation of the reporter coding region.

For detecting an inhibitor or complexing molecule (e.g., facilitator or enhancer), candidate molecules can be directly provided to a cell containing an interacting pair, or, in the case of candidate proteins, can be provided by providing their encoding nucleic acids under conditions in which the nucleic acids are recombinantly expressed to produce the candidate proteins within the cell.

This embodiment of the invention is well suited to screen chemical libraries for inhibitors or facilitators (e.g., complexing molecules) of protein—protein interactions.

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective inhibitor. Thus, in many combinatorial approaches, the position on a plate of a compound specifies that compound's composition. Also, in one example, a single plate position may have from 1–20 chemicals that can be screened by administration to a well containing the interactions of interest. Thus, if positive inhibition is detected, smaller and smaller pools of interacting pairs can be assayed for inhibition. By such methods, many inhibitors can be screened.

Many diversity libraries suitable for use are known in the art and can be used to provide compounds to be tested as inhibitors according to the present invention.

Alternatively, libraries can be constructed using standard methods. Chemical (synthetic) libraries, recombinant expression libraries, or polysome-based libraries are exemplary types of libraries that can be used.

The libraries can be constrained or semirigid (having some degree of structural rigidity), or linear or nonconstrained. The library can be a cDNA or genomic expression library, random peptide expression library or a chemically synthesized random peptide library. Expression libraries are introduced into the cells in which the inhibition assay occurs, where the nucleic acids of the library are expressed to produce their encoded proteins.

In one embodiment, the peptide libraries used in the present invention may be libraries that are chemically synthesized in vitro. Examples of such libraries are given in Houghten et al., 1991, Nature 354:84–86, which describes mixtures of free hexapeptides in which the first and second residues in each peptide were individually and specifically defined; Lam et al., 1991, Nature 354:82–84, which describes a "one bead, one peptide" approach in which a solid phase split synthesis scheme produced a library of peptides in which each bead in the collection had immobilized thereon a single, random sequence of amino acid residues; Medynski, 1994, Bio/Technology 12:709–710, which describes split synthesis and T-bag synthesis methods; and Gallop et al., 1994, J. Medicinal Chemistry 37(9):1233–1251. Simply by way of other examples, a combinatorial library may be prepared for use, according to the methods of Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; or Salmon et al., 1993, Proc. Natl. Acad. Sci. USA 90:11708–11712. PCT Publication No. WO 93/20242 and Brenner and Lerner, 1992, Proc. Natl. Acad. Sci. USA 89:5381–5383 describe "encoded combinatorial chemical libraries," that contain oligonucleotide identifiers for each chemical polymer library member. Compounds synthesized so as to be immobilized on a substrate are released from the substrate prior to use in the inhibition assay.

Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708–4712) may be used.

Conformationally constrained libraries that can be used include but are not limited to those containing invariant cysteine residues which, in an oxidizing environment, cross-link by disulfide bonds to form cystines, modified peptides (e.g., incorporating fluorine, metals, isotopic labels, are phosphorylated, etc.), peptides containing one or more non-naturally occurring amino acids, non-peptide structures, and peptides containing a significant fraction of γ-carboxyglutamic acid.

Libraries of non-peptides, e.g., peptide derivatives (for example, that contain one or more non-naturally occurring amino acids) can also be used. One example of these are peptoid libraries (Simon et al., 1992, Proc. Natl. Acad. Sci. USA 89:9367–9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al., 1994, Proc. Natl. Acad. Sci. USA 91:11138–11142).

The members of the libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid, 4-aminobutyric acid, Abu, 2-amino butyric acid; γ-Abu, ε-Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, Nα-methyl amino acids, fluoro-amino acids and amino acid analogs in general. Furthermore, the amino acid can be D (dextrorotary) or L (levorotary).

A specific embodiment of this invention uses mutant strains of yeast that have a mutation in at least one gene coding for a cell wall component, thereby having modified cell walls that are more permeable to exogenous molecules than are wild-type cell walls, thus facilitating the entry of chemicals into the cell, and rendering such yeast cells preferred for an inhibition assay in which exogenous candidate inhibitor compounds are provided directly to the cell. In one embodiment, mutations in the gene KNR4 in *Saccharomyces cerevisiae* cause the cell wall to be more permeable to chemicals like X-gal, while not affecting general growth (Hong et al., 1994, Yeast 10:1083–1092). The reporter strains are made mutant with respect to gene KNR4 to facilitate entry of inhibitor compounds. Similarly, in other embodiments, mutations in genes that influence the cell wall integrity (reviewed in Stratford, 1994, Yeast 10:1741–1752) are incorporated into the reporter strain so as to make the cell wall more permeable.

In a specific embodiment of the invention, the prospective inhibitors or complexing molecules are peptides that are genetically encoded and either plasmid-borne or are introduced into the chromosome through homologous recombination. The peptides to be screened are thus provided by recombinant expression within the cell in which the inhibition assay occurs. The peptides are preferably expressed as a fusion to a nuclear localization sequence. Alternatively, genes encoding the peptides are introduced directly into the chromosome by first cloning the genes into an integration plasmid containing the yeast sequences that donate the site necessary for homologous recombination. The transformed yeast cells are then plated on media that selects for inhibition events. In the preferred embodiment of the invention, the reporter gene for interaction and inhibition of the interaction will be the URA3 gene. Thus, transformants that emerge in media containing 5-FOA represent peptide inhibitors that inhibit specific protein—protein interactions.

In another embodiment, DNA from a microorganism that reconstitutes synthetic pathways for a compound (see Hutchinson, 1994, Bio/Technology 12:375–380; Alvarez et al., 1996, Nature Biotechnology 14:335–338) can be introduced into the cell in which the inhibition assay takes place, so as to be recombinantly expressed by the cell such that the compound is synthesized within the cell. If the synthesized compound blocks the protein interactants, such cells containing an inhibitor of the interacting pair can be detected by methods as described above. By sequencing the DNA in the cells in which inhibition of the interactants has thus occurred, a novel inhibitory compound can be identified.

The identities of the inhibitors or complexing molecules are deciphered by the isolation and sequencing of the plasmids that encode these peptides. The identities of the pair of interacting proteins, whose interaction has been inhibited by the peptide, are identified by isolation and sequencing the plasmids that encode these two proteins. The sequences of the inhibitor or complexing molecule and those of the interacting proteins can also be obtained by amplifying the protein and peptide encoding region by PCR or other methods and sequencing of the same. Specific primers can be used to amplify the peptide or the DNA-binding fusion protein or the activation domain fusion protein

5.11. KITS

In a specific embodiment, a kit comprising in one or more containers (A) a nucleic acid encoding an RNA, said RNA comprising a coding region with one or more heterologous protein-binding sites in a non-coding region 5' and adjacent to the coding region; and (B) a nucleic acid encoding a fusion protein comprising an RNA-binding protein fused to an eIF4G-like protein or a translationally active derivative thereof.

In a specific embodiment, a kit comprising in one or more containers (A) a nucleic acid encoding a fusion protein comprising an eIF4G-like protein or translationally active derivative thereof fused to a second, different protein, (B) nucleic acid encoding a fusion protein comprising an RNA-binding protein fused to a second, different protein; and (C) a nucleic acid encoding an RNA, said RNA comprising a coding region with one or more heterologous protein-binding sites in a non-coding region 5' and adjacent to the coding region.

In another specific embodiment, a kit comprising in one or more containers (A) a DNA molecule comprising a promoter operably linked to a nucleotide sequence, which nucleotide sequence is transcribed in an appropriate cell to produce an RNA, said RNA comprising one or more coding regions, each with one or more heterologous protein-binding sites in a non-coding region 5' and adjacent to the coding region; and (B) a nucleic acid encoding an RNA, said RNA comprising a coding region with one or more heterologous protein-binding sites in a non-coding region 5' and adjacent to the coding region.

In yet another specific embodiment, a kit comprising in one or more containers (A) a nucleic acid encoding a fusion protein comprising an eIF4G-like protein or translationally active derivative thereof fused to a second, different protein, (B) nucleic acid encoding a fusion protein comprising an RNA-binding protein fused to a second, different protein; and (C) a DNA molecule comprising a promoter operably linked to a nucleotide sequence, which nucleotide sequence is transcribed in an appropriate cell to produce an RNA, said RNA comprising one or more coding regions, each with one or more heterologous protein-binding sites in a non-coding region 5' and adjacent to the coding region.

5.12. TRANSGENIC ANIMALS

Described in this Section are, first, animals expressing one or more nucleic acids encoding a translational activator comprising an RNA-binding protein/eIF4G-like fusion. The invention also provides transgenic animals expressing a nucleic acid encoding a heterologous RNA molecule containing an HBS.

In a specific embodiment, the invention provides transgenic animals comprising as a transgene a nucleic acid encoding an RNA, said RNA comprising a coding region with one or more heterologous protein-binding sites in a non-coding region 5' and adjacent to the coding region. In another specific embodiment, the invention provides transgenic animals comprising as a transgene a nucleic acid encoding a fusion protein comprising an RNA-binding protein fused to an eIF4G-like protein or a translationally active derivative thereof (e.g., an RNA-binding protein/eIF4G-like protein fusion). In another specific embodiment, the invention provides transgenic animals comprising as a transgene a nucleic acid encoding a fusion protein comprising an eIF4G-like protein or translationally active derivative thereof fused to a second, different protein. In another specific embodiment, the invention provides transgenic animals comprising as a transgene a nucleic acid encoding a fusion protein comprising an RNA-binding protein fused to a second, different protein.

For clarity of discussion, not limitation, the generation of transgenic animals expressing such fusion proteins are described by way of example for the RNA-binding protein/eIF4G-like protein fusion gene. However, the principles may be analogously applied to expression and generation of animals expressing other transgenes of the invention.

The present invention relates, for example, to the generation of transgenic animals which contain an RNA-binding protein/eIF4G-like protein fusion transgene. Such transgenic animals may serve as animal models of genetic disorders, including but not limited to those of Section 5.6. The transgenic animals of the invention can be utilized in assay systems for identification of compounds capable of inhibiting or facilitating a protein—protein interaction. Such animals may also be useful for the production of a protein encoded in a gene-of-interest. The transgenic animals may be genetically engineered to overexpress a single gene, multiple genes-of-interest, which are translated by the methods of the invention.

The transgenic animals of the invention can be any species, including but not limited to mice, rats, rabbits, sheep, guinea pigs, pigs, micro-pigs, and non-human primates, e.g., baboons, monkeys, and chimpanzees. Any technique known in the art may be used to introduce a transgene encoding a fusion protein of the invention, such as an inactivating or overexpressing gene sequence, into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety).

As listed above, standard embryonal stem cell (ES) techniques can, for example, be utilized for generation of an RNA-binding protein/eIF4G-like protein fusion overexpressing animals. ES cells can be obtained from preimplantation embryos cultured in vitro (See, e.g., Evans, M. J. et al., 1981, Nature 292:154–156; Bradley, .O. et al., 1984, Nature 309:255–258; Gossler et al., 1986, Proc. Natl. Acad. Sci. USA 83:9065–9069; Robertson et al., 1986, Nature 322:445–448; Wood, S. A. et al., 1993, Proc. Natl. Acad. Sci. USA 90:4582–4584.) The introduced ES cells thereafter colonize the embryo and contribute to the germ line of a resulting chimeric animal (Jaenisch, R., 1988, Science 240:1468–1474).

Further, standard techniques such as, for example, homologous recombination, coupled with fusion protein sequences, including nucleotide sequences encoding an RNA-binding protein/eIF4G-like protein fusion protein can be utilized. A number of strategies can be utilized to detect or select rare homologous recombinants. For example, PCR can be used to screen pools of transformant cells for homologous insertion, followed by screening of individual clones (Kim et al., 1988, Nucl. Acids Res. 16:8887–8903; Kim et al., 1991, Gene 103:227–233). Alternatively, a positive genetic selection approach can be taken in which a marker gene is constructed which will only be active if homologous insertion occurs, allowing these recombinants to be selected directly (Sedivy et al., 1989, Proc. Natl. Acad. Sci. USA 86:227–231). Additionally, the positive-negative approach (PNS) method can be utilized (Mansour et al., 1988, Nature 336:348–352; Capecchi, 1989, Science 244:1288–1292; Capecchi, 1989, Trends in Genet. 5:70–76). Utilizing the PNS method, nonhomologous recombinants are selected against by using the Herpes Simplex virus thymidine kinase (HSV-TK) gene and selecting against its nonhomologous insertion with herpes drugs such as gancyclovir or FIAU. By such counter-selection, the number of homologous recombinants in the surviving transformants is increased.

ES cells generated via techniques such as these, when introduced into the germline of a nonhuman animal make possible the generation of non-mosaic, i.e., non-chimeric progeny. Such progeny will be referred to herein as founder animals. Once the founder animals are produced, they may be bred, inbred, outbred, or crossbred to produce colonies of the particular animal.

An RNA-binding protein/eIF4G-like protein fusion transgenic animals can be generated using nucleotide sequences encoding an RNA-binding protein or eIF4G-like protein fusion which are well known to those of skill in the art and/or which can routinely be isolated utilizing standard molecular biological techniques. Such sequences can encode pre-pro forms, pro- forms, as well as mature forms of proteins. Further, such sequences can include genomic sequences, cDNA sequences or hybrids thereof.

The nucleotide sequences can be utilized may be derived from any species, including but not limited to mice, rats, rabbits, guinea pigs, pigs, non-human primates, baboons, monkeys and chimpanzees. Such sequences can be routinely isolated by utilizing standard molecular techniques, for example, eIF4G-like sequences as probes and/or as PCR primers, as discussed herein. In addition, nucleotide sequences encoding proteins other than eIF4G-like protein, such as an RNA-binding protein (e.g., IRP-1) can be isolated using standard molecular biological techniques and utilized to generate transgenic animals.

To create a transgenic animal overexpressing a fusion protein of the invention, genomic DNA containing the fusion gene can be transferred into the genome of the transgenic animal using the techniques detailed below. The transgenic sequence may be derived from the same or a different species than the animal itself.

For example, transgenic animals can include mice which overexpress human transgenic sequences and/or overexpress mouse transgenic sequences. Such sequences can comprise genomic DNA, cDNA or hybrids thereof. Human genomic clones containing, for example, eIF4G1 can be isolated by screening a human genomic library by polymerase chain reaction.

The expression control elements to be used will vary depending on the desired strength or specificity of expression. As used herein, expression control elements include but are not limited to inducible and non-inducible promoters, enhancers, operators and other elements known to those skilled in the art that drive and regulate expression. Such expression control elements include, but are not limited to, viral control sequences such as the cytomegalovirus hCMV immediate early gene, the early or late promoter of SV40, or retroviral LTR sequences. Other expression control elements include the lac system, the trp system and promoters, including, but not limited to, promoters which contain AP1 regulatory sequences, derived from the mammalian genome. In instances where cell-type specfic expression is required, the regulatory sequences required for such cell-type specific activtion will depend upon the particular cell type of interest, and will be apparent to those of skill in the art. In the case of cDNA sequences, standard "mini gene" techniques can be applied for successful expression and overexpression of transgenic sequences.

Taking one example of the generation of transgenic animals, specifically transgenic mice, DNA encoding an RNA-binding protein/eIF4G-like protein fusion can be injected into inbred FVB zygotes as described by Gorden et al. (1980, Proc. Natl. Acad. Sci. USA 77:7380–7384). Genomic or vector DNA can be electroporated into W9.5 ES cells (male-derived), which can then be cultured and selected on feeder layers of mouse embryonic fibroblasts derived from transgenic mice expressing a Neo gene. G418 (350 mg/ml; for gain of Neo) and ganciclovir (2 mM; for loss of TK) can be added to the culture medium to select for resistant ES cell colonies that have undergone homologous recombination at the URO-D gene. Recombinants can then be identified by screening genomic DNA from ES cell colonies by Southern blot hybridization analysis. Correctly targeted ES cell clones, which also carry a normal complement of 40 chromosomes, can be used to derive mice carrying the mutation. ES cells can be micro-injected into blastocysts at 3.5 days post-coitum obtained from C57BL/6J mice, and blastocysts will be re-implanted into pseudopregnant female mice, which serve as foster mothers. Chimeric progeny derived largely from the ES cells are identified by a high proportion of agouti coat color (the color of the 129/sv strain of origin of the ES cells) against the black coat color derived from the C57BL/6J host blastocyst. Male chimeric progeny are tested for germline transmission of the mutation by breeding with C57BL/6J females. Agouti progeny derived from these crosses are expected to be heterozygous for the mutation, which will be confirmed by Southern blot analysis. These F1 heterozygous progeny are then inter-bred to generate F2 litters containing progeny of all three genotypes (wild type, heterozygous and homozygous mutants) for phenotypic analyses.

Transgenic mice overexpressing an RNA-binding protein/eIF4G-like protein fusion can be screened by PCR using primers from the 5' flanking region and the 3' untranslated region (UTR). Southern blot analysis may also be performed using DNA (encoding an RNA-binding protein/eIF4G-like protein fusion) as a probe to detect the presence of the fusion transgene. Transgene copy number may be estimated by quantitative analysis from Southern blot autoradiography. Message levels for transgene expression may be determined using Northern analysis from total RNA derived from tissue known to express eIF4G-like protein. Similarly, immunoblot analysis may be performed using whole cell lysates derived from tissues know to have detectable quantities of the fusion protein.

Further, one of skill in the art will recognize that cell lines expressing a fusion protein of the invention may be generated. In one embodiment, cell lines are generated from transgenic animals. In other embodiments, cell lines are generated as described above (e.g., by transfection of a host cell with nucleic acids encoding a fusion protein of the invention.

5.13. THERAPEUTICS AND PHARMACEUTICAL COMPOSITIONS

Nucleic acids encoding an RNA-binding protein/eIF4G-like protein fusion, or an eIF4G-like protein, or RNA-binding protein, as well as the DNA encoding an RNA molecule that is translated by the methods of the invention, have therapeutic utility and are referred to herein as "Therapeutics". In a preferred aspect, the Therapeutic is substantially purified.

The invention provides pharmaceutical compositions comprising an effective amount of a Therapeutic; and a pharmaceutically acceptable carrier. In a specific embodiment, the invention provides a pharmaceutical composition comprising a DNA molecule comprising a promoter operably linked to a nucleotide sequence, which nucleotide sequence is transcribed in an appropriate cell to produce an RNA, said RNA comprising one or more coding regions, each with one or more heterologous protein-binding sites in a non-coding region 5' and adjacent to the coding region. In another specific embodiment, the invention provides a pharmaceutical compositions comprising a nucleic acid encoding a fusion protein comprising an RNA-binding protein fused to an eIF4G-like protein or a translationally active derivative thereof (e.g., an RNA-binding protein/eIF4G-like protein fusion). In another specific embodiment, the invention provides pharmaceutical compositions comprising a nucleic acid encoding a fusion protein comprising an eIF4G-like protein or translationally active derivative thereof fused to a second, different protein. In another specific embodiment, the invention provides pharmaceutical compositions comprising a nucleic acid encoding a fusion protein comprising an RNA-binding protein fused to a second, different protein.

Such pharmaceutical composition is administered to a subject in need of such treatment. The subject is preferably an animal, including but not limited to animals such as cows, pigs, horses, chickens, cats, dogs, etc., and is preferably a mammal, and most preferably human. In a specific embodiment, a non-human mammal is the subject.

The amount of nucleic acid encoding an RNA molecule comprising one or more heterologous binding sites and one or more gene(s)-of-interest will be effective in the treatment of a particular disorder or condition will depend on the nature of the disorder or condition, and can be determined by standard clinical techniques.

In a specific embodiment, pharmaceutical compositions comprising nucleic acids encoding an RNA molecule to be translated by the methods of the invention, or Therapeutic of the invention are administered via liposomes, microparticles, or microcapsules. In various embodiments of the invention, it may be useful to use such compositions to achieve sustained release of the nucleic acids encoding an RNA molecule.

The invention provides methods of treatment (and prophylaxis) by administration to a subject of an effective amount of a Therapeutic of the invention.

Formulations and methods of administration of a Therapeutic can be selected from among those described herein below. Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the pulmonary system by any suitable route, including use of an inhaler or nebulizer, and formulation with an aerosolizing agent.

In another embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the Therapeutic target, i.e., the brain, thus requiring only a fraction of the systemic dose (see, e.g., Goodson, in Medical Applications of Controlled Release, supra, vol. 2, pp. 115–138 (1984)). Other controlled release systems are discussed in the review by Langer (Science 249:1527–1533 (1990)).

In a specific embodiment of the invention, fusion proteins (e.g., RNA-binding protein/eIF4G-like protein fusion, or an eIF4G-like domain fusion protein, or RNA-binding domain fusion protein) may be administered directly to a cell or subject.

Nucleic acids for gene therapy can be introduced by methods described in Section 5.6 above. The present invention also provides pharmaceutical compositions. Such compositions comprise a Therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In a specific embodiment, the invention provides a method of treating a subject having a disease or disorder amenable to treatment by a protein comprising producing a therapeutically effective amount of said protein in said organism by a method comprising introducing into said subject: (a) a DNA molecule that is transcribed within the subject to produce a monocistronic or multicistronic RNA containing a heterologous protein-binding site in a region 5' and adjacent to a coding region encoding said protein; and (b) a DNA molecule encoding a fusion protein such that the DNA molecule is expressed within the subject to produce said fusion protein, said fusion protein comprising an RNA-binding protein that binds to said heterologous protein-binding site, fused to an eIF4G-like protein or a translationally active derivative thereof. In one embodiment the fusion protein is expressed in the subject under control of an inducible promoter.

The invention provides a method of treating a subject having a disease or disorder amenable to treatment by a protein comprising (a) introducing into the subject: (i) a DNA molecule that is transcribed within the subject to produce a monocistronic or multicistronic RNA containing a heterologous protein-binding site in a region 5' and adjacent to a coding region encoding said protein; and (ii) a DNA molecule encoding a fusion protein such that the DNA molecule is expressed within the subject to produce said fusion protein, said fusion protein comprising an RNA-binding protein that binds to said heterologous protein-binding site, fused to an eIF4G-like protein or a translationally active derivative thereof: and (b) administering the cell to the subject. In one embodiment the cell is a stem or progenitor cell.

5.14. STRINGENCY CONDITIONS

Other methods available for use in connection with the methods of this invention include nucleic acid hybridization under low, moderate, or high stringency conditions (e.g., Northern and Southern blotting). Methods for adjustment of hybridization stringency are well known in the art (see, e.g., Sambrook et al., 1989, Molecular Cloning, A Laboratory Manual, 2d Ed., Cold Spring Harbor Laboratory Press, Cold Spring Harbor, N.Y.; see, also, Ausubel et al., eds., in the Current Protocols in Molecular Biology series of laboratory technique manuals, 1987–1994 Current Protocols, 1994–1997 John Wiley and Sons, Inc.; see, especially, Dyson, N.J., 1991, Immobilization of nucleic acids and hybridization analysis, In: Essential Molecular Biology: A Practical Approach, Vol. 2, T. A. Brown, ed., pp. 111–156, IRL Press at Oxford University Press, Oxford, U.K.; each of which is incorporated by reference herein in its entirety). Salt concentration, melting temperature, the absence or presence of denaturants, and the type and length of nucleic acid to be hybridized (e.g., DNA, RNA, PNA) are some of the variables considered when adjusting the stringency of a particular hybridization reaction according to methods known in the art.

By way of example and not limitation, procedures using such conditions of low stringency are as follows (see also Shilo and Weinberg, 1981, Proc. Natl. Acad. Sci. U.S.A. 78, 6789–6792). Filters containing DNA are pretreated for 6 h at 40° C. in a solution containing 35% formamide, 5× SSC, 50 mM Tris-HCl (pH 7.5), 5 mM EDTA, 0.1% PVP, 0.1%

Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2× SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

By way of example and not limitation, procedures using such conditions of high stringency are as follows. Prehybridization of filters containing DNA is carried out for 8 h to overnight at 65° C. in buffer composed of 6× SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2× SSC, 0.01% PVP, 0.01% Ficoll, and 0.01% BSA. This is followed by a wash in 0.1× SSC at 50° C. for 45 min before autoradiography. Other conditions of high stringency which may be used are well known in the art.

In another specific embodiment, conditions of moderate stringency is provided. stringency conditions are as follows. Each membrane is washed two times each for 30 minutes each at 45° C. in 40 mM sodium phosphate, pH 7.2, 5% SDS, 1 mM EDTA, 0.5% bovine serum albumin, followed by four washes each for 30 minutes in sodium phosphate, pH 7.2, 1% SDS, 1 mM EDTA, and subsequently each membrane is treated differently as described below for low, medium, or high stringency hybridization conditions. Membranes are additionally subjected to four washes each for 30 minutes in 40 mM sodium phosphate, pH 7.2, 1% SDS, 1 mM EDTA at 55° C. For high stringency hybridization the procedure for moderate stringency is followed by an additional four washes each for 30 minutes in 40 mM sodium phosphate, pH 7.2, 1% SDS, 1 mM EDTA at 55° C., followed by four washes each for 30 minutes in sodium phosphate, pH 7.2, 1% SDS, 1 mM EDTA at 65° C.

5.15. RNA PREPARATION

In several embodiments of the invention, purified RNA is used for the methods of the invention. Not by way of limitation, some or all of the following methods may be used in the preparation of such RNA.

RNA extraction may be preformed by any method known in the art. For example, the cells to be extracted are mixed with Triazol reagent (Life Technologies, Gaithersburg, Md.). Cells are then mixed with 0.2 volumes of chloroform are added and vortexed for 15 seconds, and phases separated by centrifugation (5000×g, 15 min). The aqueous phase is precipitated with 0.6 volumes of 2-propanol. The precipitated RNA is pelleted at 10,000×g for 15 min, rinsed with 70% ethanol and dried. The RNA pellet is resuspended in water to give a final concentration of 100 ng/µl.

In a further specific embodiment, DNAse treatment is performed. For example, but not be limitation, Dnase treatment is carried out as follows: 0.2 volumes of 5× reverse transcriptase buffer (Life Technologies), 0.1 volumes of 0.1 M DTT, and 5 units RNAguard/100 mg starting tissue (Pharmacia Biotech, Uppsala, Sweden) are added to the RNA extracted according to Section 6.1.3. One unit RNase-free DNase I (Pharmacia Biotech)/100 mg starting tissue is added, and the mixture is incubated at 37° C. for 20 min. 10 volumes of Triazol is added and RNA extraction by addition of chloroform and precipitation is repeated.

In another specific embodiment of the invention, mRNA may be purified to be used in the methods of the invention. For example, but not by limitation, RNA concentration is estimated by measuring $OD_{260}$ of a 100-fold dilution of extracted RNA mixture after DNase treatment. In one embodiment, mRNA is purified using oligo(dT) beads, for example, the Dynal oligo(dT) magnetic beads have a capacity of 1 µg poly(A+) per 100 µg of beads (1 mg/ml concentration). Assuming that 2% of the total RNA is poly(A+), 5 volumes of Lysis/Binding buffer (Dynal, Oslo, Norway) and sufficient beads to bind poly(A+) are added. This mixture is heated at 65° C. for 2 min and then incubated at room temperature for 5 min. The beads are first washed with 1 ml washing buffer/LiDS (Dynal), then with 1 ml washing buffer (Dynal, Oslo, Norway) twice. The poly(A+) RNA is eluted twice with 1 µl water/µg beads.

In another specific embodiment, preparation of polysomal and non-polysomal RNAs may be performed by any method known in the art. For example, RNA from animal organs may be prepared as described in Zahringer et al., 1976, *Proc. Natl. Acad. Sci., USA*, 73:857–861; RNA from tissue culture cells may be prepared as described in Rogers and Munro, 1987, *Proc. Natl. Acad. Sci., USA* 84:2277–2281; or as in Melefors et al., 1993, *J. Biol. Chem.* 268:5974–5978.

In another embodiment, RNA for use in the invention may be prepared by in vitro transcription. Commercially available kits for in vitro transcription are known in the art and are within the scope of the invention.

In another specific embodiment, methods of the invention may be used in conjunction with cell-free translation systems as described in Gray and Hentze, 1994, *EMBO J.* 13:3882–3891.

6. EXAMPLE

The following examples are provided merely as illustrative of various aspects of the invention and shall not be construed to limit the invention in any way.

6.1. CONSTRUCTION OF AN eIF4G/RNA-BINDING PROTEIN FUSION

In order to construct an eIF4G/RNA-binding fusion protein of the invention, the N-terminal eIF4E- and PABP-binding region of eIF4GI was replaced by a specific RNA-binding protein (RBP) which was directed to a cognate binding site (B.S.) in the intercistronic space of a bicistronic reporter mRNA (FIG. 1*a*, lower scheme). By assaying the translation of the second cistron, which is normally translated very poorly, this approach permits to assess eIF4G function independent of eIF4E- and PXBP-binding.

Two classes of plasmid vectors were constructed. The first, termed effector plasmids (e.g., encoding eIF4G and/or RNA-binding proteins) were constructed to express human iron regulatory protein-1 alone (pSGIRP), or IRP-1 fused to parts of human eIF4GI (e.g. pSGIRP-4G, FIG. 3). Effector plasmids were constructed as follows: Human eIF4GI cDNA sequences were excised from p220Bam (De Gregorio, et al., 1998, RNA 4:828–36) with BamHI-HindIII and inserted in frame behind the IRP-1 coding region, into the MscI-HindIII sites of pSGIRP (Kollmus, et al., 1996, *RNA* 2:316–323) to create plasmid pSGIRP-4G. A BamHI-EcoRI fragment from pGEX4G935 (De Gregorio, et al., 1998, *RNA* 4:828–36) or a BamHI-NsiI fragment from p220Bam were inserted into the MscI site of pSGIRP to create plasmids pSGIRP-4G1091 and pSGIRP-4G877, respectively.

The second, termed reporter plasmids, encoded heterologous RNA, specifically vectors were constructed to encode bicistronic mRNAs coding for the reporter proteins luciferase (LUC, upstream) and chloramphenicol acetyltransferase (CAT, downstream). Binding sites for IRP-1 (an HBS called iron-responsive element, IRE) or binding sites for the bacteriophage MS2 coat protein as a negative control (MSC) were introduced into the heterologous RNA (FIG. 1a). Reporter plasmids were constructed as follows: pΔ4× IREGH, pΔ3+1×IREGH and p2+Δ2IREGH (Goossen, et al, 1990, *EMBO J.* 9:4127–4133) were amplified by PCR using the primers: 3×5: GACGGATCCAAAAAATAC (set forth in SEQ ID NO.12) and 3×3: GGTCTAGAACTCTAGCGTC-CAAGCAC (set forth in SEQ ID NO. 13). The amplification products were digested with BamHI-XbaI and cloned into the BamHI-XbaI sites of pIRECAT creating pΔ3CAT, pΔ2+1CAT and p1+Δ2CAT. SacI-HindIII fragments from pIRECAT, pIREscpCAT (Preiss, et al., 1998, *RNA* 4:1321–1331), pIRE100 (Paraskeva, et al., 1999, *Mol. Cell. Biol.* 19:807–816), pMSC-CAT (Stripecke, et al., 1992, *Nucl. Acids Res.* 20:5555–5564), pΔ3CAT, pΔ2+1CAT p1+Δ2CAT or a BamHI-HindIII fragment from p4×IRE-CAT were ligated into the XhoI sites of pSGluctrs3 (Pantopoulos, et al., 1995, *Proc. Natl. Acad. Sci. USA* 92:1267–1271) to generate the reporter plasmids: pSGIRE, pSGIREΔ33, pSG66-IRE, pSGMSC, pSGΔ3, pSGΔ2+1, pSG1+Δ2 and pSG3×IRE (see FIGS. 2A–B for schematic of intercistronic regions, see FIG. 8 for sequences of intercistronic regions). pSGG243 was constructed by inserting a synthetic fragment of dsDNA into the AvrII site of pSG3×IRE (FIG. 4). All plasmid manipulations were verified by sequencing by methods known in the art.

TABLE I

Intercistronic regions of plasmids.

| CONSTRUCT | Abbreviation as depicted in FIG. 2 | SEQ ID NO. |
| --- | --- | --- |
| pSGIRE | IRE | 3 |
| pSG66-IRE | 66-IRE | 4 |
| pSGIREΔ33 | IREΔ33 | 5 |
| pSGMSC | MSC | 6 |
| pSG3xIRE | 3xIRE | 7 |
| pSGΔ2+1 | Δ2+1 | 8 |
| pSG1+Δ2 | 1+Δ2 | 9 |
| pSGΔ3 | Δ3 | 10 |

These plasmids were transfected into HeLa cells together with a third plasmid, expressing β-galactosidase (β-Gal) as a transfection efficiency control. HeLa cells were maintained and transiently transfected by the calcium phosphate method using 2 pmol of effector plasmids (unless indicated otherwise), 2 pmol of bicistronic vector and 1 pmol of pCMVβ expressing β-Gal. Metabolic labeling, immunoprecipitation and gel mobility shift assays confirmed that the expression levels and RNA-binding activities were similar for IRP-1 and IRP-4G (see FIG. 5). CAT and LUC activities were corrected for transfection efficiencies and the data expressed in relation to controls. CAT assays were performed using a CAT-ELISA kit (Boehringer Mannheim) following the manufacturer's instructions. Luciferase and β-Gal expression were measured by enzymatic activity. Transfection with the "empty" effector plasmid pSG5 (termed "relative CAT or LUC expression served as a control. The ratios between the expression of IRP-1 alone versus the IRP-4G fusion protein were also examined.

As seen in FIG. 1, IRP-1 alone did not induce CAT activity (white bars). By contrast, IRP-4G activated CAT expression about 3 to 5-fold when an IRE (e.g., an HBS) mediated its binding to the intercistronic space. Importantly, it failed to do so when the IRE was replaced by the MSC site (FIG. 1b) which bound neither IRP-1 nor IRP-4G (FIG. 5). A further activation in CAT expression was observed when the bicistronic mRNA contained three IREs instead of one (FIG. 1b, right-most bar) which indicated that increasing the number of HBSs increased translation of the reporter gene. The effect of the IRP-4G fusion protein was specific for the downstream cistron, since any changes in LUC expression were only minor (1.2 to 1.6-fold) and independent of the binding sites in the intercistronic region (FIG. 1b). Northern analysis performed on both total (FIG. 6) demonstrated that the IRP-4G-dependent activation of CAT expression did not result from changes in mRNA levels or the generation of monocistronic cleavage products. Thus, IRP-4G fusion protein activated the translation of the downstream cistron in a binding-site-specific manner.

6.2. POSITION OF RECRUITMENT AND NUMBER OF BINDING SITES

The exact position to which the IRP-4G fusion protein was recruited affected the function of the protein (FIG. 2a). Increasing the distance of the IRE to the upstream cistron by 66 nucleotides (66-IRE) from 70 to 136 nucleotides yielded a reproducible improvement in CAT activation. Reducing the distance to the downstream cistron from 46 to 13 nucleotides (IREΔ33) had a negative effect on translation. Thus, the positioning and context of the IRP-4G fusion protein within the intercistronic space affected the translation of the downstream cistron.

To determine whether the CAT activation was caused by the multiplicity of binding sites or an improved positioning of one of them, derivatives of the 3×IRE construct were generated. In each position either a wild type IRE or an IRE with a single nucleotide deletion (Δ) that reduced its affinity for IRP-1 (Goossen, et al, 1990, *EMBO J.* 9:4127–4133) was generated. Mutations of the two upstream (Δ2+1) or the two downstream (1+Δ2) IREs resulted in markedly weaker activation of CAT expression compared to the wild type 3×IRE construct (FIG. 2b). Mutation of all three IREs in construct Δ3 profoundly decreased, CAT activation, indicating that the number of binding sites affects translation of the downstream gene.

6.3. eIF4G CORE DOMAIN

To map a functional domain of eIF4G that directed downstream translation, C-terminal deletions were assayed (FIG. 3a). The deletion called IRP-4G1091, lacked the C-terminal of the two eIF4A binding sites, but retained the putative RRM and the binding region for eIF3. This fusion protein was still able to activate CAT translation, but exhibited lower efficiency of translation (FIG. 3b). Thus, the central region of eIF4G was sufficient to activate translation. This result was consistent with findings that the central region of eIF4G activated the translation of uncapped mRNAs in vitro (De Gregorio, et al., 1998, *RNA* 4:828–36) and promoted binding of the 40S ribosomal subunit to the internal ribosome entry site (IRES) of encephalomyocarditis virus (EMCV) (Pestova, et al., 1996, *Mol. Cell. Biol.*

16:6870–6878). A further deletion of eIF4G sequences in the form of a deletion called (IRP-4G877) that preserved the RRM region but removed the sequences necessary for eIF3 binding resulted in a complete loss of activity (FIG. 3b). Thus, the activation of translation by the core region of eIF4G was not merely due to non-specific RNA-binding properties but was mediated by the RRM, implicating a role of eIF3. Immunoblots confirmed that IRP-4G and IRP-4G1091 fusion proteins were expressed at similar levels when equal amounts of effector plasmids were transfected. As seen in FIG. 3c, titration of the effector plasmid IRP-4G877 failed to stimulate CAT translation at any DNA concentration tested (FIG. 3c), even when IRP-4G877 fusion protein levels exceeded those of IRP-4G (FIG. 7). This further demonstrated that transfection of 0.5 to 1.0 pmol pSGIRP-4G plasmid yielded a further substantial increase in downstream cistron translation over the previously used 2.0 pmol (FIG. 3c).

6.4. IRES-LIKE FUNCTION OF IRE/IRP-4G

Internal ribosome entry sites (IRES) that are used by some viral and cellular mRNAs are the only known RNA elements that can drive the translation of a downstream cistron of bicistronic mRNAs (Sachs, et al., 1997, *Cell* 89:831–838). To compare the relative strength of IRP-4G mediated activation with the potency of a natural IRES, the full-length IRES from hepatitis C virus (Reynolds, J. E. et al., 1995, *EMBO J.* 14:6010–6020) was cloned between the LUC and CAT cistrons of the reporter plasmid. This construct yielded approximately 7-fold higher CAT protein levels than the IRP-4G/3×IRE module under the same conditions, while luciferase activity was similar in both cases. Thus, the effect displayed by the eIF4G fusion protein lead to a significant activation of translation.

IRES recruit ribosomes internally, independent from the translation of upstream cistrons (Chen, et al., 1995, *Science* 268:415–517). In order to address the mechanism of IRP-4G directed ribosome recruitment a stable stem-loop structure (as set forth in SEQ ID NO.11 (ΔG=−243 kJ/mol) was inserted into the 5' UTR of 3×IRE (FIG. 4b), such loops inhibit translation by native translation factors, (Kozak, M., 1986, *Proc. Natl. Acad. Sci. USA* 83:2850–2854. The insertion of the stem-loop repressed LUC expression almost completely 96–97% (FIG. 4a). Surprisingly, however, the activation of CAT translation remained high (FIG. 4). This result demonstrated that, while some of the ribosomes were re-recruited from the upstream LUC reading frame, the majority of the ribosomes translating the CAT coding region were recruited from the free 43S pool.

An important advantage of this discovery is that a multicistronic RNA molecule may be constructed such that it provides an internal control or calibration standard for the cap-dependent translation of said RNA. Specifically, construction of a multicistronic RNA molecule comprising (a) a 5' most cistron (or reporter gene) without an upstream HBS, as demonstrated in this example by a LUC cistron, allows for the 5' most cistron to be an indicator of basal levels translation (b) one or more downstream cistrons linked to one or more HBSs, as exemplified in this example by CAT as the cistron and IRE as the HBS. Thus, translation of the 5' most cistron or reporter gene, LUC indicated the cap-dependent translation from the multicistronic RNA molecule, and thus served as a calibration standard for the translation of the downstream HBS-mediated cistron CAT.

The inventors have discovered a central region of eIF4G which has an active "ribosome recruitment core" and was capable of activating translation. This core domain functional portion of eIF4G required no more than a means to bind upstream of an open reading frame (e.g., binding to an HBS) to recruit all additional factors necessary for translation. eIF4G binding to a site upstream of an open reading frame was illustrated herein via an IRE/IRP-1 interaction.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims.

Various references are cited herein above, including patent applications, patents, and publications, the disclosures of which are hereby incorporated by reference in their entireties.

What is claimed:

1. A method of producing a protein comprising contacting within a eukaryotic cell: (a) an RNA molecule comprising (i) a coding region encoding said protein, and (ii) a protein-binding site in a noncoding region 5' and adjacent to said coding region; and (b) a fusion protein comprising (i) an RNA-binding protein that binds to said protein-binding site, fused to an eIF4G-like protein or a translationally active derivative thereof.

2. The method of claim 1 wherein the RNA molecule comprises two or more coding regions, and wherein a heterologous protein-binding site is in an intercistronic region.

3. The method of claim 2 wherein said RNA comprises two or more heterologous protein-binding sites in at least one intercistronic region.

4. The method of claim 2 wherein said two or more coding regions (a) are 3' to another coding region, and (b) each encodes a different subunit of a multi-subunit protein.

5. The method of 1 wherein the cell is a stem or progenitor cell.

6. A method of producing a protein comprising recombinantly expressing a fusion protein with a eukaryotic cell, wherein the cell contains a DNA molecule that is transcribed within the cell to produce an RNA containing a heterologous protein-binding site in a region 5' and adjacent to a coding region encoding said protein; wherein the fusion protein comprises (i) an RNA-binding protein that binds to said protein-binding site, fused to an eIF4G-like protein or a translationally active derivative thereof.

7. The method of claim 6 wherein the DNA molecule is a plasmid expression vector.

8. The method of claim 7 wherein the plasmid comprises an inducible promoter controlling production of said RNA.

9. The method of claim 6 wherein the fusion protein is expressed from a plasmid expression vector comprising a promoter operably linked to a nucleotide sequence encoding said fusion protein.

10. The method of claim 9 wherein the promoter is inducible.

11. The method of claim 6 wherein said RNA comprises two or more identical heterologous protein-binding sites in an intercistronic region.

12. The method of claim 6 wherein said RNA comprises two or more intercistronic regions which contain the heterologous protein-binding site, each of said two or more intercistronic regions encoding a different subunit of a multi-subunit protein.

13. A kit comprising in one or more containers (a) a nucleic acid encoding an RNA, said RNA comprising a coding region with one or more heterologous protein-binding sites in a non-coding region 5' and adjacent to the coding region; and (b) a nucleic acid encoding a fusion protein comprising an RNA-binding protein fused to an eIF4G-like protein or a translationally active derivative thereof, wherein the RNA binding protein binds to the heterologous protein-binding site.

14. A kit comprising in one or more containers (a) a nucleic acid encoding a fusion protein comprising an eIF4G-like protein or translationally active derivative thereof fused to a second, different protein; (b) a nucleic acid encoding a fusion protein comprising an RNA-binding protein fused to a third, different protein; and (c) a nucleic acid encoding an RNA, said RNA comprising a coding region with one or more heterologous protein-binding sites in a non-coding region 5' and adjacent to the coding region, wherein the RNA-binding protein binds to the heterologous protein binding site.

15. A method of producing a protein comprising contacting within a eukaryotic cell: (a) an RNA molecule comprising (i) a coding region encoding said protein, and (ii) a protein-binding site in a noncoding region 5' and adjacent to said coding region; and (b) a fusion protein comprising (i) an RNA-binding protein that binds to said protein-binding site, fused to a second protein, said second protein which is capable of binding to an eIF4G-like protein.

16. A nucleic acid encoding an RNA, said RNA comprising two or more coding regions with two or more heterologous protein-binding sites in at least one intercistronic region.

17. A kit comprising in a container the nucleic acid of claim 16.

18. The kit of claim 17 further comprising in a container a nucleic acid comprising a nucleotide sequence encoding a fusion protein, said fusion protein comprising an RNA-binding protein fused to an eIF4G-like protein or translationally active derivative thereof, wherein the RNA-binding protein binds to at least one of the heterologous protein binding sites.

19. The kit of claim 17 further comprising in a container a nucleic acid comprising a nucleotide sequence encoding a fusion protein, said fusion protein comprising a translationally active derivative of an eIF4G-like protein fused to the carboxy-terminus of a second, different protein, wherein the eIF4G-like protein is selected from the group consisting of human eIF4G1, human p97/DAP-5, and eIF(iso)4G-p82, and wherein the translationally active derivative comprises an eIF3 binding domain, lacks one or more PABP domains, and lacks an eIF4E binding domain.

20. The kit of claim 17 further comprising in a container a nucleic acid comprising a nucleotide sequence encoding a fusion protein, said fusion protein comprising a translationally active derivative of an eIF4G-like protein fused to a second, different protein, wherein the eIF4G-like protein is selected from the group consisting of human eIF4G1, human p97/DAP-5, and eIF(iso)4G-p82, and wherein the translationally active derivative comprises an eIF3 binding domain and lacks the 5' most eIF4A binding domain.

21. The kit of claim 17, 19 or 20 further comprising in a container a nucleic acid comprising a nucleotide sequence encoding a fusion protein, said fusion protein comprising an RNA-binding protein fused to a second, different protein, wherein the RNA-binding protein is IRP-1, bacteriophage MS2 coat protein, spliceosomal protein U1A, or λ box B binding protein and the RNA-binding protein binds to at least one of the heterologous protein binding sites.

22. The nucleic acid of claim 16, wherein at least one of said two or more heterologous protein-binding sites comprises an iron-responsive element (IRE), an MS2 RNA replicase site, a U1A snRNA site, or a λ box B site.

23. An isolated recombinant cell comprising the nucleic acid of claim 16.

24. The isolated recombinant cell of claim 23, wherein the host cell is a stem or progenitor cell.

25. A DNA molecule comprising a promoter operably linked to a nucleotide sequence, wherein said nucleotide sequence when transcribed produces an RNA, said RNA comprising two or more coding regions with two or more heterologous protein-binding sites in at least one intercistronic region.

26. The DNA molecule of claim 25, wherein the RNA comprises three or more heterologous protein-binding sites in at least one intercistronic region.

27. The DNA molecule of claim 25, wherein the RNA comprises four or more heterologous protein-binding sites in at least one intercistronic region.

28. The DNA molecule of claim 25, wherein the RNA comprises 5–10 heterologous protein-binding sites in at least one intercistronic region.

29. The DNA molecule of claim 25, wherein the RNA comprises 10–20 heterologous protein-binding sites in at least one intercistronic region.

30. The DNA molecule of claim 25, wherein the RNA comprises 20 or more heterologous protein-binding sites in at least one intercistronic region.

31. The DNA molecule of claim 25, wherein at least one of said two or more coding regions comprises a reporter gene coding region.

32. The DNA molecule of claim 25, wherein at least one of said two or more coding regions that is 3' to another coding region is a reporter gene coding region.

33. The DNA molecule of claim 25, wherein at least one of said two or more coding regions encodes a therapeutic protein.

34. The DNA molecule of claim 25, wherein at least one of said two or more coding regions that is 3' to another coding region encodes a therapeutic protein.

35. The DNA molecule of claim 25, 26, 27 which is purified.

36. The DNA molecule of claim 25, wherein the promoter is constitutive.

37. The DNA molecule of claim 25, wherein the promoter is inducible.

38. The DNA molecule of claim 25, wherein at least one of said two or more heterologous protein-binding sites comprises an iron-responsive element (IRE), an MS2 RNA replicase site, a U1A snRNA site, or a λ box B site.

39. An expression vector comprising the DNA molecule of claim 25 and an origin of replication.

40. An RNA molecule comprising two or more coding regions with two or more heterologous protein-binding sites in at least one intercistronic region.

41. The RNA molecule of claim 40, wherein at least one of said two or more heterologous protein-binding sites comprises an iron-responsive element (IRE), an MS2 RNA replicase site, a U1A snRNA site, or a λ box B site.

42. The RNA molecule of claim 40 which is purified.

43. A nucleic acid comprising a nucleotide sequence encoding a fusion protein, said fusion protein comprising an RNA-binding protein fused to an eIF4G-like protein or translationally active derivative thereof.

44. The nucleic acid of claim 43, wherein the RNA-binding protein is fused to a transcriptionally active derivative of an eIF4G-like protein.

45. The nucleic acid of claim 44, wherein the transcriptionally active derivative comprises amino acids 489 to 1404 of human eIF4G1 (SEQ ID NO.:2).

46. The nucleic acid of claim 44, wherein the transcriptionally active derivative comprises amino acids 967 to 1074 of human eIF4G1 (SEQ ID NO.:2).

47. The nucleic acid of claim 44, wherein the transcriptionally active derivative comprises an eIF3 binding domain.

48. The nucleic acid of claim 47, wherein the transcriptionally active derivative lacks one or more poly(A)-binding protein (PABP) domains and an eIF4E binding domain.

49. The nucleic acid of claim 44, wherein the transcriptionally active derivative comprises an eIF3 binding domain and eIF4A binding domains.

50. The nucleic acid of claim 44, wherein the transcriptionally active derivative comprises an eIF3 binding domain, eIF4A binding domains, and an RRM domain.

51. The nucleic acid of claim 49 or 50, wherein the transcriptionally active derivative lacks one or more poly(A)-binding protein (PABP) domains and an eIF4E binding domain.

52. The nucleic acid of claim 43, wherein the RNA-binding protein is IRE-binding protein (IRP).

53. The nucleic acid of claim 43 that further comprises a promoter operably linked to said nucleotide sequence encoding said fusion protein.

54. An expression vector comprising the nucleic acid of claim 53 and an origin of replication.

55. A nucleic acid comprising a nucleotide sequence encoding a fusion protein, said fusion protein comprising a second, different protein fused at the carboxy-terminus of a translationally active derivative of an eIF4G-like protein, wherein the eIF4G-like protein is selected from the group consisting of human eIF4G1, human p97/DAP-5, and eIF(iso)4G-p82, and wherein the translationally active derivative comprises an eIF3 binding domain.

56. The nucleic acid of claim 55, wherein the translationally active derivative further comprises an eIF4A binding domain.

57. The nucleic acid of claim 55, wherein the translationally active derivative comprises amino acids 967 to 1074 of human eIF4G1 (SEQ ID NO.:2).

58. The nucleic acid of claim 55 that further comprises a promoter operably linked to said nucleotide sequence encoding said fusion protein.

59. An expression vector comprising the nucleic acid of claim 58 and an origin of replication.

60. A nucleic acid comprising a nucleotide sequence encoding a fusion protein, said fusion protein comprising a translationally active derivative of an eIF4G-like protein fused to a second, different protein, wherein the eIF4G-like protein is selected from the group consisting of human eIF4G1, human p97/DAP-5, and eIF(iso)4G-p82, and wherein the translationally active derivative comprises an eIF3 binding domain and lacks the 5' most eIF4A binding domain.

61. The nucleic acid of claim 60, wherein the translationally active derivative comprises amino acids 967 to 1074 of human eIF4G1 (SEQ ID NO.:2).

62. The nucleic acid of claim 60 that further comprises a promoter operably linked to said nucleotide sequence encoding said fusion protein.

63. An expression vector comprising the nucleic acid of claim 62 and an origin of replication.

64. The nucleic acid of claim 55 or 60, wherein the translationally active derivative further lacks one or both of a PABP domain and an eIF4E binding domain.

65. The nucleic acid of claim 43, 55 or 60 which is purified.

66. An isolated recombinant cell comprising the nucleic acid of claim 60 or 62.

67. The isolated recombinant cell of claim 66, wherein the host cell is a stem or progenitor cell.

68. A nucleic acid comprising a nucleotide sequence encoding a fusion protein, said fusion protein comprising an RNA-binding protein fused to a second, different protein, wherein the RNA-binding protein is IRP-1, bacteriophage MS2 coat protein, spliceosomal protein U1A, or λ box B binding protein.

69. The nucleic acid of claim 68 that further comprises a promoter operably linked to said nucleotide sequence encoding said fusion protein.

70. An expression vector comprising the nucleic acid of claim 69 and an origin of replication.

71. The nucleic acid of claim 68 or 69 which is purified.

72. An isolated recombinant cell comprising the nucleic acid of claim 68 or 69.

73. The isolated recombinant cell of claim 72, wherein the host cell is a stem or progenitor cell.

74. A population of nucleic acids, wherein each nucleic acid in the population is a vector comprising: (a) an origin of replication; (b) a nucleic acid comprising a nucleotide sequence encoding a fusion protein, said fusion protein comprising an eIF4G-like protein or a translationally active derivative thereof fused to a second, different protein; and (c) a promoter operably linked to said nucleotide sequence; wherein the identity of said second, different protein varies among the fusion proteins encoded by said population.

75. The population of claim 74, wherein the transcriptionally active derivative is fused to the carboxy-terminus of the second, different protein.

76. The population of claim 74, wherein the transcriptionally active derivative is fused to the amino-terminus of the second, different protein.

77. The population of claim 74, wherein the transcriptionally active derivative comprises an eIF3 binding domain and lacks one or both of a PABP domain and an eIF4E binding domain.

78. The population of claim 74, wherein the transcriptionally active derivative comprises an eIF3 binding domain and lacks the 5' most eIF4A binding domain.

79. A population of nucleic acids, wherein each nucleic acid in the population is a vector comprising: (a) an origin of replication; (b) a nucleic acid comprising a nucleotide sequence encoding a fusion protein, said fusion protein comprising an RNA-binding protein fused to a second, different protein; and (c) a promoter operably linked to said nucleotide sequence; wherein the identity of said second, different protein varies among the fusion proteins encoded by said population.

80. The population of claim 79, wherein the RNA-binding protein is selected from the group consisting of IRP-1, bacteriophage MS2 coat protein, spliceosomal protein U1A, and λ box B binding protein.

81. The population of claim 74 or 79, wherein the fusion proteins encoded by said population comprise at least 100 distinct ones of said second, different proteins.

82. The population of claim 74 or 79, wherein the nucleotide sequences encoding said second, different proteins are those of a cDNA library.

83. The population of claim 74 or 79 wherein the nucleotide sequences encoding said second, different proteins are those of a random or biased peptide expression library.

84. An isolated recombinant cell comprising the nucleic acid of claim 55 or 58.

85. An isolated eukaryotic cell comprising:
(a) an RNA molecule comprising (i) a coding region encoding a protein, and (ii) a protein-binding site in a noncoding region 5' and adjacent to said coding region; and
(b) a nucleic acid comprising a nucleotide sequence encoding a fusion protein, said fusion protein comprising an RNA-binding protein that binds to said protein-binding site, fused to an eIF4G-like protein or a translationally active derivative thereof.

86. An isolated recombinant cell comprising the nucleic acid of claim 43 or 53.

87. A method of producing a fusion protein comprising subjecting a recombinant cell comprising the nucleic acid of claim 43, 55, 60, or 68 to conditions such that the nucleotide sequence is expressed by the cell, and recovering said fusion protein from said cell.

88. A population of cells comprising the DNA molecule of claim 25 or the nucleic acid of claim 43, 55, 60 or 68.

89. A composition comprising the DNA molecule of claim 25 or the nucleic acid of claim 43, 55, 60 or 68 in a pharmaceutically acceptable carrier.

90. A nucleic acid comprising a nucleotide sequence encoding a fusion protein, said fusion protein comprising an RNA-binding protein fused to a protein that binds to an eIF4G-like protein.

91. The nucleic acid of claim 90 that further comprises a promoter operably linked to said nucleotide sequence encoding said fusion protein.

92. An expression vector comprising the nucleic acid of claim 91, and an origin of replication.

93. An isolated recombinant cell comprising the nucleic acid of claim 90 or 91.

94. An isolated recombinant cell comprising the expression vector of claim 39, 52, 54, 59, 70, or 92.

95. The isolated recombinant cell of claim 93, wherein the host cell is a stem or progenitor cell.

96. The isolated recombinant cell of claim 94, wherein the host cell is a stem or progenitor cell.

97. A kit comprising in a container the nucleic acid of claim 43, 55, 60, 68 or 90.

98. A kit comprising in a container the expression vector of claims 39, 63, 54, 59, 90 or 92.

99. A population of recombinant cells comprising the population of nucleic acids of claim 74 or 79.

100. The isolated recombinant cell of claim 84, wherein the host cell is a stem or progenitor cell.

101. The isolated recombinant cell of claim 86, wherein the host cell is a stem or progenitor cell.

102. An isolated eukaryotic cell comprising:
   (a) a DNA molecule that is transcribed within the cell to produce an RNA containing a heterologous protein-binding site in a region 5' and adjacent to a coding region encoding a protein; and
   (b) a nucleic acid comprising a nucleotide sequence encoding a fusion protein, said fusion protein comprising an RNA-binding protein that binds to said heterologous protein-binding site, fused to an eIF4G-like protein or a translationally active derivative thereof.

103. An isolated eukaryotic cell comprising:
   (a) a DNA molecule that is transcribed within the cell to produce an RNA containing a heterologous protein-binding site in a region 5' and adjacent to a reporter gene coding region; and
   (b) a nucleic acid comprising a nucleotide sequence encoding a fusion protein, said fusion protein comprising an eIF4G-like protein or a translationally active derivative thereof fused to a second, different protein.

104. An isolated eukaryotic cell comprising:
   (a) an RNA comprising a heterologous test RNA sequence in a region 5' and adjacent to a reporter gene coding region; and
   (b) a nucleic acid comprising a nucleotide sequence encoding a fusion protein, said fusion protein comprising an eIF4G-like protein or a translationally active derivative thereof fused to a second, different protein for which it is desired to identify an RNA site to which said second, different protein binds.

105. A population of isolated eukaryotic cells comprising:
   (a) a population of nucleic acids, each nucleic acid of said population comprising a nucleotide sequence encoding a fusion protein, said fusion protein comprising an eIF4G-like protein or a translationally active derivative thereof fused to a second, different protein, wherein said second, different protein varies among the fusion proteins encoded by said population; and
   (b) a DNA that is transcribed to produce an RNA comprising a heterologous protein-binding site in a region 5' and adjacent to a reporter gene coding region.

106. An isolated eukaryotic cell comprising:
   (a) a nucleic acid comprising a nucleotide sequence encoding a fusion protein, said fusion protein comprising an eIF4G-like protein or a translationally active derivative thereof fused to a second, different protein;
   (b) a nucleic acid comprising a nucleotide sequence encoding a fusion protein, said fusion protein comprising an RNA-binding protein fused to a third, different protein; and
   (c) a DNA that is transcribed to produce an RNA comprising a heterologous protein-binding site in a region 5' and adjacent to a reporter gene coding region, wherein said RNA-binding protein binds to said heterologous protein-binding site.

107. A population of isolated eukaryotic cells comprising:
   (a) a DNA that is transcribed to produce an RNA comprising a heterologous protein-binding site in a region 5' and adjacent to a reporter gene coding region;
   (b) a first population of nucleic acids, said first population of nucleic acids comprising a nucleotide sequence encoding a fusion protein, said fusion protein comprising an RNA-binding protein fused to a second, different protein, wherein the identity of said second, different protein varies among the fusion proteins encoded by said first population of nucleic acids, and wherein the RNA-binding protein binds to the heterologous protein-binding site; and
   (c) a second population of nucleic acids, said second population of nucleic acids comprising a nucleotide sequence encoding a fusion protein, said fusion protein comprising an eIF4G-like protein or transcriptionally active derivative thereof fused to a third, different protein, wherein the identity of said third, different protein varies among the fusion proteins encoded by said second population of nucleic acids.

\* \* \* \* \*

SEQUENCE LISTING

<160> NUMBER OF SEQ ID NOS: 13

<210> SEQ ID NO 1
<211> LENGTH: 5128
<212> TYPE: DNA
<213> ORGANISM: Homo sapiens
<220> FEATURE:
<221> NAME/KEY: CDS
<222> LOCATION: (13)..(4692)

<400> SEQUENCE: 1

```
caagcgacac aa atg aac acg cct tct cag ccc cgc cag cac ttc tac cct      51
              Met Asn Thr Pro Ser Gln Pro Arg Gln His Phe Tyr Pro
                1               5                  10 agc cgg gcc cag ccc ccg agc agt gca gcc tcc cga gtg cag agt gca      99
Ser Arg Ala Gln Pro Pro Ser Ser Ala Ala Ser Arg Val Gln Ser Ala
 15                  20                  25 gcc cct gcc cgc cct ggc cca gct gcc cat gtc tac cct gct gga tcc     147
Ala Pro Ala Arg Pro Gly Pro Ala Ala His Val Tyr Pro Ala Gly Ser
```

```
                30                    35                    40                    45 caa gta atg atg atc cct tcc cag atc tcc tac cca gcc tcc cag ggg      195
Gln Val Met Met Ile Pro Ser Gln Ile Ser Tyr Pro Ala Ser Gln Gly
                    50                    55                    60 gcc tac tac atc cct gga cag ggg cgt tcc aca tac gtt gtc ccg aca      243
Ala Tyr Tyr Ile Pro Gly Gln Gly Arg Ser Thr Tyr Val Val Pro Thr
            65                    70                    75 cag cag tac cct gtg cag cca gga gcc cca ggc ttc tat cca ggt gca      291
Gln Gln Tyr Pro Val Gln Pro Gly Ala Pro Gly Phe Tyr Pro Gly Ala
        80                    85                    90 agc cct aca gaa ttt ggg acc tac gct ggc gcc tac tat cca gcc caa      339
Ser Pro Thr Glu Phe Gly Thr Tyr Ala Gly Ala Tyr Tyr Pro Ala Gln
    95                    100                   105 ggg gtg cag cag ttt ccc act ggc gtg gcc ccc gcc cca gtt ttg atg      387
Gly Val Gln Gln Phe Pro Thr Gly Val Ala Pro Ala Pro Val Leu Met
110                   115                   120                   125 aac cag cca ccc cag att gct ccc aag agg gag cgt aag acg atc cga      435
Asn Gln Pro Pro Gln Ile Ala Pro Lys Arg Glu Arg Lys Thr Ile Arg
                    130                   135                   140 att cga gat cca aac caa gga gga aag gat atc aca gag gag atc atg      483
Ile Arg Asp Pro Asn Gln Gly Gly Lys Asp Ile Thr Glu Glu Ile Met
                145                   150                   155 tct ggg gcc cgc act gcc tcc aca ccc acc cct ccc cag acg gga ggc      531
Ser Gly Ala Arg Thr Ala Ser Thr Pro Thr Pro Pro Gln Thr Gly Gly
            160                   165                   170 ggt ctg gag cct caa gct aat ggg gag acg ccc cag gtt gct gtc att      579
Gly Leu Glu Pro Gln Ala Asn Gly Glu Thr Pro Gln Val Ala Val Ile
        175                   180                   185 gtc cgg cca gat gac cgg tca cag gga gca atc att gct gac cgg cca      627
Val Arg Pro Asp Asp Arg Ser Gln Gly Ala Ile Ile Ala Asp Arg Pro
190                   195                   200                   205 ggg ctg cct ggc cca gag cat agc cct tca gaa tcc cag cct tcg tcg      675
Gly Leu Pro Gly Pro Glu His Ser Pro Ser Glu Ser Gln Pro Ser Ser
                    210                   215                   220 cct tct ccg acc cca tca cca tcc cca gtc ttg gaa ccg ggg tct gag      723
Pro Ser Pro Thr Pro Ser Pro Ser Pro Val Leu Glu Pro Gly Ser Glu
                225                   230                   235 cct aat ctc gca gtc ctc tct att cct ggg gac act atg aca act ata      771
Pro Asn Leu Ala Val Leu Ser Ile Pro Gly Asp Thr Met Thr Thr Ile
            240                   245                   250 caa atg tct gta gaa gaa tca acc ccc atc tcc cgt gaa act ggg gag      819
Gln Met Ser Val Glu Glu Ser Thr Pro Ile Ser Arg Glu Thr Gly Glu
        255                   260                   265 cca tat cgc ctc tct cca gaa ccc act cct ctc gcc gaa ccc ata ctg      867
Pro Tyr Arg Leu Ser Pro Glu Pro Thr Pro Leu Ala Glu Pro Ile Leu
270                   275                   280                   285 gaa gta gaa gtg aca ctt agc aaa ccg gtt cca gaa tct gag ttt tct      915
Glu Val Glu Val Thr Leu Ser Lys Pro Val Pro Glu Ser Glu Phe Ser
                    290                   295                   300 tcc agt cct ctc cag gct ccc acc cct ttg gca tct cac aca gtg gaa      963
Ser Ser Pro Leu Gln Ala Pro Thr Pro Leu Ala Ser His Thr Val Glu
                305                   310                   315 att cat gag cct aat ggc atg gtc cca tct gaa gat ctg gaa cca gag      1011
Ile His Glu Pro Asn Gly Met Val Pro Ser Glu Asp Leu Glu Pro Glu
            320                   325                   330 gtg gag tca agc cca gag ctt gct cct ccc cca gct tgc ccc tcc gaa      1059
Val Glu Ser Ser Pro Glu Leu Ala Pro Pro Pro Ala Cys Pro Ser Glu
        335                   340                   345 tcc cct gtg ccc att gct cca act gcc caa cct gag gaa ctg ctc aac      1107
```

-continued

| | |
|---|---|
| Ser Pro Val Pro Ile Ala Pro Thr Ala Gln Pro Glu Leu Leu Asn<br>350                    355                    360                    365 | |
| gga gcc ccc tcg cca cca gct gtg gac tta agc cca gtc agt gag cca<br>Gly Ala Pro Ser Pro Pro Ala Val Asp Leu Ser Pro Val Ser Glu Pro<br>                    370                    375                    380 | 1155 |
| gag gag cag gcc aag gag gtg aca gca tca gtg gcg ccc ccc acc atc<br>Glu Glu Gln Ala Lys Glu Val Thr Ala Ser Val Ala Pro Pro Thr Ile<br>          385                    390                    395 | 1203 |
| ccc tct gct act cca gct acg gct cct tca gct act tcc cca gct cag<br>Pro Ser Ala Thr Pro Ala Thr Ala Pro Ser Ala Thr Ser Pro Ala Gln<br>        400                    405                    410 | 1251 |
| gag gag gaa atg gaa gaa gaa gaa gag gaa gaa gga gaa gca gga<br>Glu Glu Glu Met Glu Glu Glu Glu Glu Glu Glu Gly Glu Ala Gly<br>415                    420                    425 | 1299 |
| gaa gca gga gaa gct gag agt gag aaa gga gga gag gaa ctg ctc ccc<br>Glu Ala Gly Glu Ala Glu Ser Glu Lys Gly Gly Glu Glu Leu Leu Pro<br>430                    435                    440                    445 | 1347 |
| cca gag agt acc cct att cca gcc aac ttg tct cag aat ttg gag gca<br>Pro Glu Ser Thr Pro Ile Pro Ala Asn Leu Ser Gln Asn Leu Glu Ala<br>                    450                    455                    460 | 1395 |
| gca gca gcc act caa gtg gca gta tct gtg cca aag agg aga cgg aaa<br>Ala Ala Ala Thr Gln Val Ala Val Ser Val Pro Lys Arg Arg Arg Lys<br>                  465                    470                    475 | 1443 |
| att aag gag cta aat aag aag gag gct gtt gga gac ctt ctg gat gcc<br>Ile Lys Glu Leu Asn Lys Lys Glu Ala Val Gly Asp Leu Leu Asp Ala<br>              480                    485                    490 | 1491 |
| ttc aag gag gcg aac ccg gca gta cca gag gtg gaa aat cag cct cct<br>Phe Lys Glu Ala Asn Pro Ala Val Pro Glu Val Glu Asn Gln Pro Pro<br>      495                    500                    505 | 1539 |
| gca ggc agc aat cca ggc cca gag tct gag ggc agt ggt gtg ccc cca<br>Ala Gly Ser Asn Pro Gly Pro Glu Ser Glu Gly Ser Gly Val Pro Pro<br>510                    515                    520                    525 | 1587 |
| cgt cct gag gaa gca gat gag acc tgg gac tca aag gaa gac aaa att<br>Arg Pro Glu Glu Ala Asp Glu Thr Trp Asp Ser Lys Glu Asp Lys Ile<br>                    530                    535                    540 | 1635 |
| cac aat gct gag aac atc cag ccc ggg gaa cag aag tat gaa tat aag<br>His Asn Ala Glu Asn Ile Gln Pro Gly Glu Gln Lys Tyr Glu Tyr Lys<br>              545                    550                    555 | 1683 |
| tca gat cag tgg aag cct cca aac cta gag gag aaa aaa cgt tac gac<br>Ser Asp Gln Trp Lys Pro Pro Asn Leu Glu Glu Lys Lys Arg Tyr Asp<br>          560                    565                    570 | 1731 |
| cgt gag ttc ctg ctt ggt ttt cag ttc atc ttt gcc agt atg cag aag<br>Arg Glu Phe Leu Leu Gly Phe Gln Phe Ile Phe Ala Ser Met Gln Lys<br>575                      580                    585 | 1779 |
| cca gag gga ttg cca cat atc agt gac gtg gtg ctg gac aag gcc aat<br>Pro Glu Gly Leu Pro His Ile Ser Asp Val Val Leu Asp Lys Ala Asn<br>590                    595                    600                    605 | 1827 |
| aaa aca cca ctg cgg cca ctg gat ccc act aga cta caa ggc ata aat<br>Lys Thr Pro Leu Arg Pro Leu Asp Pro Thr Arg Leu Gln Gly Ile Asn<br>                    610                    615                    620 | 1875 |
| tgt ggc cca gac ttc act cca tcc ttt gcc aac ctt ggc cgg aca acc<br>Cys Gly Pro Asp Phe Thr Pro Ser Phe Ala Asn Leu Gly Arg Thr Thr<br>              625                    630                    635 | 1923 |
| ctt agc acc cgt ggg ccc cca agg ggt ggg cca ggt ggg gag ctg ccc<br>Leu Ser Thr Arg Gly Pro Pro Arg Gly Gly Pro Gly Gly Glu Leu Pro<br>        640                    645                    650 | 1971 |
| cgt ggg ccg cag gct ggc ctg gga ccc cgg cgc tct cag cag gga ccc<br>Arg Gly Pro Gln Ala Gly Leu Gly Pro Arg Arg Ser Gln Gln Gly Pro<br>655                      660                    665 | 2019 |

```
cga aaa gaa cca cgc aag atc att gcc aca gtg tta atg acc gaa gat      2067
Arg Lys Glu Pro Arg Lys Ile Ile Ala Thr Val Leu Met Thr Glu Asp
670                 675                 680                 685 ata aaa ctg aac aaa gca gag aaa gcc tgg aaa ccc agc agc aag cgg      2115
Ile Lys Leu Asn Lys Ala Glu Lys Ala Trp Lys Pro Ser Ser Lys Arg
            690                 695                 700 acg gcg gct gat aag gat cga ggg gaa gaa gat gct gat ggc agc aaa      2163
Thr Ala Ala Asp Lys Asp Arg Gly Glu Glu Asp Ala Asp Gly Ser Lys
        705                 710                 715 acc cag gac cta ttc cgc agg gtg cgc tcc atc ctg aat aaa ctg aca      2211
Thr Gln Asp Leu Phe Arg Arg Val Arg Ser Ile Leu Asn Lys Leu Thr
    720                 725                 730 ccc cag atg ttc cag cag ctg atg aag caa gtg acg cag ctg gcc atc      2259
Pro Gln Met Phe Gln Gln Leu Met Lys Gln Val Thr Gln Leu Ala Ile
735                 740                 745 gac acc gag gaa cgc ctc aaa ggg gtc att gac ctc att ttt gag aag      2307
Asp Thr Glu Glu Arg Leu Lys Gly Val Ile Asp Leu Ile Phe Glu Lys
750                 755                 760                 765 gcc att tca gag ccc aac ttc tct gtg gcc tat gcc aac atg tgc cgc      2355
Ala Ile Ser Glu Pro Asn Phe Ser Val Ala Tyr Ala Asn Met Cys Arg
            770                 775                 780 tgc ctc atg gcg ctg aaa gtg ccc act acg gaa aag cca aca gtg act      2403
Cys Leu Met Ala Leu Lys Val Pro Thr Thr Glu Lys Pro Thr Val Thr
        785                 790                 795 gtg aac ttc cga aag ctg ttg ttg aat cga tgt cag aag gag ttt gag      2451
Val Asn Phe Arg Lys Leu Leu Leu Asn Arg Cys Gln Lys Glu Phe Glu
    800                 805                 810 aaa gac aaa gat gat gat gag gtt ttt gag aag aag caa aaa gag atg      2499
Lys Asp Lys Asp Asp Asp Glu Val Phe Glu Lys Lys Gln Lys Glu Met
815                 820                 825 gat gaa gct gct acg gca gag gaa cga gga cgc ctg aag gaa gag ctg      2547
Asp Glu Ala Ala Thr Ala Glu Glu Arg Gly Arg Leu Lys Glu Glu Leu
830                 835                 840                 845 gaa gag gct cgg gac ata gcc cgg cgg cgc tct tta ggg aat atc aag      2595
Glu Glu Ala Arg Asp Ile Ala Arg Arg Arg Ser Leu Gly Asn Ile Lys
            850                 855                 860 ttt att gga gag ttg ttc aaa ctg aag atg tta aca gag gca ata atg      2643
Phe Ile Gly Glu Leu Phe Lys Leu Lys Met Leu Thr Glu Ala Ile Met
        865                 870                 875 cat gac tgt gtg gtc aaa ctg ctt aag aac cat gat gaa gag tcc ctt      2691
His Asp Cys Val Val Lys Leu Leu Lys Asn His Asp Glu Glu Ser Leu
    880                 885                 890 gag tgc ctt tgt cgt ctg ctc acc acc att ggc aaa gac ctg gac ttt      2739
Glu Cys Leu Cys Arg Leu Leu Thr Thr Ile Gly Lys Asp Leu Asp Phe
895                 900                 905 gaa aaa gcc aag ccc cga atg gat cag tat ttc aac cag atg gaa aaa      2787
Glu Lys Ala Lys Pro Arg Met Asp Gln Tyr Phe Asn Gln Met Glu Lys
910                 915                 920                 925 atc att aaa gaa aag aag acg tca tcc cgc atc cgc ttt atg ctg cag      2835
Ile Ile Lys Glu Lys Lys Thr Ser Ser Arg Ile Arg Phe Met Leu Gln
            930                 935                 940 gac gtg ctg gat ctg cga ggg agc aat tgg gtg cca cgc cga ggg gat      2883
Asp Val Leu Asp Leu Arg Gly Ser Asn Trp Val Pro Arg Arg Gly Asp
        945                 950                 955 cag ggt ccc aag acc att gac cag atc cat aag gag gct gag atg gaa      2931
Gln Gly Pro Lys Thr Ile Asp Gln Ile His Lys Glu Ala Glu Met Glu
    960                 965                 970 gaa cat cga gag cac atc aaa gtg cag cag ctc atg gcc aag ggc agt      2979
Glu His Arg Glu His Ile Lys Val Gln Gln Leu Met Ala Lys Gly Ser
975                 980                 985
```

```
gac aag cgt cgg ggc ggt cct cca ggc cct ccc atc agc cgt gga ctt      3027
Asp Lys Arg Arg Gly Gly Pro Pro Gly Pro Pro Ile Ser Arg Gly Leu
990             995                 1000                1005 ccc ctt gtg gat gat ggt ggc tgg aac aca gtt ccc atc agc aaa ggt      3075
Pro Leu Val Asp Asp Gly Gly Trp Asn Thr Val Pro Ile Ser Lys Gly
            1010                1015                1020 agc cgc ccc att gac acc tca cga ctc acc aag atc acc aag cct ggc      3123
Ser Arg Pro Ile Asp Thr Ser Arg Leu Thr Lys Ile Thr Lys Pro Gly
        1025                1030                1035 tcc atc gat tct aac aac cag ctc ttt gca cct gga ggg cga ctg agc      3171
Ser Ile Asp Ser Asn Asn Gln Leu Phe Ala Pro Gly Gly Arg Leu Ser
    1040                1045                1050 tgg ggc aag ggc agc agc gga ggc tca gga gcc aag ccc tca gac gca      3219
Trp Gly Lys Gly Ser Ser Gly Gly Ser Gly Ala Lys Pro Ser Asp Ala
1055                1060                1065 gca tca gaa gct gct cgc cca gct act agt act ttg aat cgc ttc tca      3267
Ala Ser Glu Ala Ala Arg Pro Ala Thr Ser Thr Leu Asn Arg Phe Ser
1070                1075                1080                1085 gcc ctt caa caa gcg gta ccc aca gaa agc aca gat aat aga cgt gtg      3315
Ala Leu Gln Gln Ala Val Pro Thr Glu Ser Thr Asp Asn Arg Arg Val
            1090                1095                1100 gtg cag agg agt agc ttg agc cga gaa cga ggc gag aaa gct gga gac      3363
Val Gln Arg Ser Ser Leu Ser Arg Glu Arg Gly Glu Lys Ala Gly Asp
        1105                1110                1115 cga gga gac cgc cta gag cgg agt gaa cgg gga ggg gac cgt ggg gac      3411
Arg Gly Asp Arg Leu Glu Arg Ser Glu Arg Gly Gly Asp Arg Gly Asp
    1120                1125                1130 cgg ctt gat cgt gcg cgg aca cct gct acc aag cgg agc ttc agc aag      3459
Arg Leu Asp Arg Ala Arg Thr Pro Ala Thr Lys Arg Ser Phe Ser Lys
1135                1140                1145 gaa gtg gag gag cgg agt aga gaa cgg ccc tcc cag cct gag ggg ctg      3507
Glu Val Glu Glu Arg Ser Arg Glu Arg Pro Ser Gln Pro Glu Gly Leu
1150                1155                1160                1165 cgc aag gca gct agc ctc acg gag gat cgg gac cgt ggg cgg gat gcc      3555
Arg Lys Ala Ala Ser Leu Thr Glu Asp Arg Asp Arg Gly Arg Asp Ala
            1170                1175                1180 gtg aag cga gaa gct gcc cta ccc cca gtg agc ccc ctg aag gcg gct      3603
Val Lys Arg Glu Ala Ala Leu Pro Pro Val Ser Pro Leu Lys Ala Ala
        1185                1190                1195 ctc tct gag gag gag tta gag aag aaa tcc aag gct atc att gag gaa      3651
Leu Ser Glu Glu Glu Leu Glu Lys Lys Ser Lys Ala Ile Ile Glu Glu
    1200                1205                1210 tat ctc cat ctc aat gac atg aaa gag gca gtc cag tgc gtg cag gag      3699
Tyr Leu His Leu Asn Asp Met Lys Glu Ala Val Gln Cys Val Gln Glu
1215                1220                1225 ctg gcc tca ccc tcc ttg ctc ttc atc ttt gta cgg cat ggt gtc gag      3747
Leu Ala Ser Pro Ser Leu Leu Phe Ile Phe Val Arg His Gly Val Glu
1230                1235                1240                1245 tct acg ctg gag cgc agt gcc att gct cgt gag cat atg ggg cag ctg      3795
Ser Thr Leu Glu Arg Ser Ala Ile Ala Arg Glu His Met Gly Gln Leu
            1250                1255                1260 ctg cac cag ctg ctc tgt gct ggg cat ctg tct act gct cag tac tac      3843
Leu His Gln Leu Leu Cys Ala Gly His Leu Ser Thr Ala Gln Tyr Tyr
        1265                1270                1275 caa ggg ttg tat gaa atc ttg gaa ttg gct gag gac atg gaa att gac      3891
Gln Gly Leu Tyr Glu Ile Leu Glu Leu Ala Glu Asp Met Glu Ile Asp
    1280                1285                1290 atc ccc cac gtg tgg ctc tac cta gcg gaa ctg gta aca ccc att ctg      3939
Ile Pro His Val Trp Leu Tyr Leu Ala Glu Leu Val Thr Pro Ile Leu
```

```
                1295              1300              1305
cag gaa ggt ggg gtg ccc atg ggg gag ctg ttc agg gag att aca aag      3987
Gln Glu Gly Gly Val Pro Met Gly Glu Leu Phe Arg Glu Ile Thr Lys
1310              1315              1320              1325 cct ctg aga ccg ttg ggc aaa gct gct tcc ctg ttg ctg gag atc ctg      4035
Pro Leu Arg Pro Leu Gly Lys Ala Ala Ser Leu Leu Leu Glu Ile Leu
         1330              1335              1340 ggc ctc ctg tgc aaa agc atg ggt cct aaa aag gtg ggg acg ctg tgg      4083
Gly Leu Leu Cys Lys Ser Met Gly Pro Lys Lys Val Gly Thr Leu Trp
    1345              1350              1355 cga gaa gcc ggg ctt agc tgg aag gaa ttt cta cct gaa ggc cag gac      4131
Arg Glu Ala Gly Leu Ser Trp Lys Glu Phe Leu Pro Glu Gly Gln Asp
1360              1365              1370 att ggt gca ttc gtc gct gaa cag aag gtg gag tat acc ctg gga gag      4179
Ile Gly Ala Phe Val Ala Glu Gln Lys Val Glu Tyr Thr Leu Gly Glu
    1375              1380              1385 gag tcg gaa gcc cct ggc cag agg gca ctc ccc tcc gag gag ctg aac      4227
Glu Ser Glu Ala Pro Gly Gln Arg Ala Leu Pro Ser Glu Glu Leu Asn
1390              1395              1400              1405 agg cag ctg gag aag ctg ctg aag gag ggc agc agt aac cag cgg gtg      4275
Arg Gln Leu Glu Lys Leu Leu Lys Glu Gly Ser Ser Asn Gln Arg Val
         1410              1415              1420 ttc gac tgg ata gag gcc aac ctg agt gag cag cag ata gta tcc aac      4323
Phe Asp Trp Ile Glu Ala Asn Leu Ser Glu Gln Gln Ile Val Ser Asn
    1425              1430              1435 acg tta gtt cga gcc ctc atg acg gct gtc tgc tat tct gca att att      4371
Thr Leu Val Arg Ala Leu Met Thr Ala Val Cys Tyr Ser Ala Ile Ile
1440              1445              1450 ttt gag act ccc ctc cga gtg gac gtt gca gtg ctg aaa gcg cga gcg      4419
Phe Glu Thr Pro Leu Arg Val Asp Val Ala Val Leu Lys Ala Arg Ala
         1455              1460              1465 aag ctg ctg cag aaa tac ctg tgt gac gag cag aag gag cta cag gcg      4467
Lys Leu Leu Gln Lys Tyr Leu Cys Asp Glu Gln Lys Glu Leu Gln Ala
1470              1475              1480              1485 ctc tac gcc ctc cag gcc ctt gta gtg acc tta gaa cag cct ccc aac      4515
Leu Tyr Ala Leu Gln Ala Leu Val Val Thr Leu Glu Gln Pro Pro Asn
         1490              1495              1500 ctg ctg cgg atg ttc ttt gac gca ctg tat gac gag gac gtg gtg aag      4563
Leu Leu Arg Met Phe Phe Asp Ala Leu Tyr Asp Glu Asp Val Val Lys
    1505              1510              1515 gag gat gcc ttc tac agt tgg gag agt agc aag gac ccc gct gag cag      4611
Glu Asp Ala Phe Tyr Ser Trp Glu Ser Ser Lys Asp Pro Ala Glu Gln
1520              1525              1530 cag ggc aag ggt gtg gcc ctt aaa tct gtc aca gcc ttc ttc aag tgg      4659
Gln Gly Lys Gly Val Ala Leu Lys Ser Val Thr Ala Phe Phe Lys Trp
         1535              1540              1545 ctc cgt gaa gca gag gag gag tct gac cac aac tgagggctgg tggggccggg   4712
Leu Arg Glu Ala Glu Glu Glu Ser Asp His Asn
1550              1555              1560 gacctggagc cccatggaca cacagatggc ccggctagcc gcctggactg caggggggcg   4772
gcagcagcgg cggtggcagt gggtgcctgt agtgtgatgt gtctgaacta ataaagtggc   4832
tgaagaggca ggatggcttg gggctgcctg gccccctc caggatgccg ccaggtgtcc     4892
ctctcctccc cctggggcac agagatatat tatatataaa gtcttgaaat ttggtgtgtc   4952
ttggggtggg gaggggcacc aacgcctgcc cctgggtcc ttttttttat tttctgaaaa    5012
tcactctcgg gactgccgtc ctcgctgctg ggggcatatg cccagcccc tgtaccaccc    5072 ctgctgttgc ctgggcaggg ggaaggggggg gcacggtgcc tgtaattatt aaacat      5128
```

-continued

```
<210> SEQ ID NO 2
<211> LENGTH: 1560
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Asn | Thr | Pro | Ser | Gln | Pro | Arg | Gln | His | Phe | Tyr | Pro | Ser | Arg | Ala |
| 1 | | | | 5 | | | | | 10 | | | | | 15 | |
| Gln | Pro | Pro | Ser | Ser | Ala | Ala | Ser | Arg | Val | Gln | Ser | Ala | Ala | Pro | Ala |
| | | | 20 | | | | | 25 | | | | | 30 | | |
| Arg | Pro | Gly | Pro | Ala | Ala | His | Val | Tyr | Pro | Ala | Gly | Ser | Gln | Val | Met |
| | | | 35 | | | | | 40 | | | | | 45 | | |
| Met | Ile | Pro | Ser | Gln | Ile | Ser | Tyr | Pro | Ala | Ser | Gln | Gly | Ala | Tyr | Tyr |
| | 50 | | | | | 55 | | | | | 60 | | | | |
| Ile | Pro | Gly | Gln | Gly | Arg | Ser | Thr | Tyr | Val | Val | Pro | Thr | Gln | Gln | Tyr |
| 65 | | | | | 70 | | | | | 75 | | | | | 80 |
| Pro | Val | Gln | Pro | Gly | Ala | Pro | Gly | Phe | Tyr | Pro | Gly | Ala | Ser | Pro | Thr |
| | | | | 85 | | | | | 90 | | | | | 95 | |
| Glu | Phe | Gly | Thr | Tyr | Ala | Gly | Ala | Tyr | Tyr | Pro | Ala | Gln | Gly | Val | Gln |
| | | | | 100 | | | | | 105 | | | | | 110 | |
| Gln | Phe | Pro | Thr | Gly | Val | Ala | Pro | Ala | Pro | Val | Leu | Met | Asn | Gln | Pro |
| | | | 115 | | | | | 120 | | | | | 125 | | |
| Pro | Gln | Ile | Ala | Pro | Lys | Arg | Glu | Arg | Lys | Thr | Ile | Arg | Ile | Arg | Asp |
| | 130 | | | | | 135 | | | | | 140 | | | | |
| Pro | Asn | Gln | Gly | Gly | Lys | Asp | Ile | Thr | Glu | Glu | Ile | Met | Ser | Gly | Ala |
| 145 | | | | | 150 | | | | | 155 | | | | | 160 |
| Arg | Thr | Ala | Ser | Thr | Pro | Thr | Pro | Pro | Gln | Thr | Gly | Gly | Gly | Leu | Glu |
| | | | | 165 | | | | | 170 | | | | | 175 | |
| Pro | Gln | Ala | Asn | Gly | Glu | Thr | Pro | Gln | Val | Ala | Val | Ile | Val | Arg | Pro |
| | | | | 180 | | | | | 185 | | | | | 190 | |
| Asp | Asp | Arg | Ser | Gln | Gly | Ala | Ile | Ile | Ala | Asp | Arg | Pro | Gly | Leu | Pro |
| | | | 195 | | | | | 200 | | | | | 205 | | |
| Gly | Pro | Glu | His | Ser | Pro | Ser | Glu | Ser | Gln | Pro | Ser | Ser | Pro | Ser | Pro |
| | 210 | | | | | 215 | | | | | 220 | | | | |
| Thr | Pro | Ser | Pro | Ser | Pro | Val | Leu | Glu | Pro | Gly | Ser | Glu | Pro | Asn | Leu |
| 225 | | | | | 230 | | | | | 235 | | | | | 240 |
| Ala | Val | Leu | Ser | Ile | Pro | Gly | Asp | Thr | Met | Thr | Thr | Ile | Gln | Met | Ser |
| | | | | 245 | | | | | 250 | | | | | 255 | |
| Val | Glu | Glu | Ser | Thr | Pro | Ile | Ser | Arg | Glu | Thr | Gly | Glu | Pro | Tyr | Arg |
| | | | | 260 | | | | | 265 | | | | | 270 | |
| Leu | Ser | Pro | Glu | Pro | Thr | Pro | Leu | Ala | Glu | Pro | Ile | Leu | Glu | Val | Glu |
| | | | 275 | | | | | 280 | | | | | 285 | | |
| Val | Thr | Leu | Ser | Lys | Pro | Val | Pro | Glu | Ser | Glu | Phe | Ser | Ser | Ser | Pro |
| | 290 | | | | | 295 | | | | | 300 | | | | |
| Leu | Gln | Ala | Pro | Thr | Pro | Leu | Ala | Ser | His | Thr | Val | Glu | Ile | His | Glu |
| 305 | | | | | 310 | | | | | 315 | | | | | 320 |
| Pro | Asn | Gly | Met | Val | Pro | Ser | Glu | Asp | Leu | Glu | Pro | Glu | Val | Glu | Ser |
| | | | | 325 | | | | | 330 | | | | | 335 | |
| Ser | Pro | Glu | Leu | Ala | Pro | Pro | Ala | Cys | Pro | Ser | Glu | Ser | Pro | Val |
| | | | | 340 | | | | | 345 | | | | | 350 | |
| Pro | Ile | Ala | Pro | Thr | Ala | Gln | Pro | Glu | Glu | Leu | Leu | Asn | Gly | Ala | Pro |
| | | | 355 | | | | | 360 | | | | | 365 | | |
| Ser | Pro | Pro | Ala | Val | Asp | Leu | Ser | Pro | Val | Ser | Glu | Pro | Glu | Glu | Gln |

```
            370                 375                 380
Ala Lys Glu Val Thr Ala Ser Val Ala Pro Pro Thr Ile Pro Ser Ala
385                 390                 395                 400

Thr Pro Ala Thr Ala Pro Ser Ala Thr Ser Pro Ala Gln Glu Glu Glu
                405                 410                 415

Met Glu Glu Glu Glu Glu Glu Glu Gly Glu Ala Gly Glu Ala Gly
            420                 425                 430

Glu Ala Glu Ser Glu Lys Gly Gly Glu Glu Leu Leu Pro Pro Glu Ser
                435                 440                 445

Thr Pro Ile Pro Ala Asn Leu Ser Gln Asn Leu Glu Ala Ala Ala
    450                 455                 460

Thr Gln Val Ala Val Ser Val Pro Lys Arg Arg Arg Lys Ile Lys Glu
465                 470                 475                 480

Leu Asn Lys Lys Glu Ala Val Gly Asp Leu Leu Asp Ala Phe Lys Glu
                485                 490                 495

Ala Asn Pro Ala Val Pro Glu Val Glu Asn Gln Pro Pro Ala Gly Ser
            500                 505                 510

Asn Pro Gly Pro Glu Ser Glu Gly Ser Gly Val Pro Pro Arg Pro Glu
            515                 520                 525

Glu Ala Asp Glu Thr Trp Asp Ser Lys Glu Asp Lys Ile His Asn Ala
    530                 535                 540

Glu Asn Ile Gln Pro Gly Glu Gln Lys Tyr Glu Tyr Lys Ser Asp Gln
545                 550                 555                 560

Trp Lys Pro Pro Asn Leu Glu Lys Lys Arg Tyr Asp Arg Glu Phe
            565                 570                 575

Leu Leu Gly Phe Gln Phe Ile Phe Ala Ser Met Gln Lys Pro Glu Gly
                580                 585                 590

Leu Pro His Ile Ser Asp Val Val Leu Asp Lys Ala Asn Lys Thr Pro
            595                 600                 605

Leu Arg Pro Leu Asp Pro Thr Arg Leu Gln Gly Ile Asn Cys Gly Pro
    610                 615                 620

Asp Phe Thr Pro Ser Phe Ala Asn Leu Gly Arg Thr Thr Leu Ser Thr
625                 630                 635                 640

Arg Gly Pro Pro Arg Gly Gly Pro Gly Gly Glu Leu Pro Arg Gly Pro
                645                 650                 655

Gln Ala Gly Leu Gly Pro Arg Ser Gln Gln Gly Pro Arg Lys Glu
            660                 665                 670

Pro Arg Lys Ile Ile Ala Thr Val Leu Met Thr Glu Asp Ile Lys Leu
    675                 680                 685

Asn Lys Ala Glu Lys Ala Trp Lys Pro Ser Ser Lys Arg Thr Ala Ala
    690                 695                 700

Asp Lys Asp Arg Gly Glu Glu Asp Ala Asp Gly Ser Lys Thr Gln Asp
705                 710                 715                 720

Leu Phe Arg Arg Val Arg Ser Ile Leu Asn Lys Leu Thr Pro Gln Met
                725                 730                 735

Phe Gln Gln Leu Met Lys Gln Val Thr Gln Leu Ala Ile Asp Thr Glu
            740                 745                 750

Glu Arg Leu Lys Gly Val Ile Asp Leu Ile Phe Glu Lys Ala Ile Ser
            755                 760                 765

Glu Pro Asn Phe Ser Val Ala Tyr Ala Asn Met Cys Arg Cys Leu Met
    770                 775                 780

Ala Leu Lys Val Pro Thr Thr Glu Lys Pro Thr Val Thr Val Asn Phe
785                 790                 795                 800
```

-continued

Arg Lys Leu Leu Leu Asn Arg Cys Gln Lys Glu Phe Glu Lys Asp Lys
                805                 810                 815

Asp Asp Asp Glu Val Phe Glu Lys Lys Gln Lys Glu Met Asp Glu Ala
            820                 825                 830

Ala Thr Ala Glu Glu Arg Gly Arg Leu Lys Glu Glu Leu Glu Glu Ala
        835                 840                 845

Arg Asp Ile Ala Arg Arg Ser Leu Gly Asn Ile Lys Phe Ile Gly
    850                 855                 860

Glu Leu Phe Lys Leu Lys Met Leu Thr Glu Ala Ile Met His Asp Cys
865                 870                 875                 880

Val Val Lys Leu Leu Lys Asn His Asp Glu Glu Ser Leu Glu Cys Leu
                885                 890                 895

Cys Arg Leu Leu Thr Thr Ile Gly Lys Asp Leu Asp Phe Glu Lys Ala
                900                 905                 910

Lys Pro Arg Met Asp Gln Tyr Phe Asn Gln Met Glu Lys Ile Ile Lys
                915                 920                 925

Glu Lys Lys Thr Ser Ser Arg Ile Arg Phe Met Leu Gln Asp Val Leu
        930                 935                 940

Asp Leu Arg Gly Ser Asn Trp Val Pro Arg Arg Gly Asp Gln Gly Pro
945                 950                 955                 960

Lys Thr Ile Asp Gln Ile His Lys Glu Ala Glu Met Glu Glu His Arg
                965                 970                 975

Glu His Ile Lys Val Gln Gln Leu Met Ala Lys Gly Ser Asp Lys Arg
            980                 985                 990

Arg Gly Gly Pro Pro Gly Pro Pro Ile Ser Arg Gly Leu Pro Leu Val
        995                 1000                1005

Asp Asp Gly Gly Trp Asn Thr Val Pro Ile Ser Lys Gly Ser Arg Pro
   1010                1015                1020

Ile Asp Thr Ser Arg Leu Thr Lys Ile Thr Lys Pro Gly Ser Ile Asp
1025                1030                1035                1040

Ser Asn Asn Gln Leu Phe Ala Pro Gly Gly Arg Leu Ser Trp Gly Lys
                1045                1050                1055

Gly Ser Ser Gly Gly Ser Gly Ala Lys Pro Ser Asp Ala Ala Ser Glu
            1060                1065                1070

Ala Ala Arg Pro Ala Thr Ser Thr Leu Asn Arg Phe Ser Ala Leu Gln
        1075                1080                1085

Gln Ala Val Pro Thr Glu Ser Thr Asp Asn Arg Arg Val Val Gln Arg
    1090                1095                1100

Ser Ser Leu Ser Arg Glu Arg Gly Glu Lys Ala Gly Asp Arg Gly Asp
1105                1110                1115                1120

Arg Leu Glu Arg Ser Glu Arg Gly Gly Asp Arg Gly Asp Arg Leu Asp
                1125                1130                1135

Arg Ala Arg Thr Pro Ala Thr Lys Arg Ser Phe Ser Lys Glu Val Glu
            1140                1145                1150

Glu Arg Ser Arg Glu Arg Pro Ser Gln Pro Glu Gly Leu Arg Lys Ala
        1155                1160                1165

Ala Ser Leu Thr Glu Asp Arg Asp Arg Gly Arg Asp Ala Val Lys Arg
    1170                1175                1180

Glu Ala Ala Leu Pro Pro Val Ser Pro Leu Lys Ala Ala Leu Ser Glu
1185                1190                1195                1200

Glu Glu Leu Glu Lys Lys Ser Lys Ala Ile Ile Glu Glu Tyr Leu His
                1205                1210                1215

Leu Asn Asp Met Lys Glu Ala Val Gln Cys Val Gln Glu Leu Ala Ser
        1220                1225                1230

Pro Ser Leu Leu Phe Ile Phe Val Arg His Gly Val Glu Ser Thr Leu
        1235                1240                1245

Glu Arg Ser Ala Ile Ala Arg Glu His Met Gly Gln Leu Leu His Gln
1250                1255                1260

Leu Leu Cys Ala Gly His Leu Ser Thr Ala Gln Tyr Tyr Gln Gly Leu
1265                1270                1275                1280

Tyr Glu Ile Leu Glu Leu Ala Glu Asp Met Glu Ile Asp Ile Pro His
                1285                1290                1295

Val Trp Leu Tyr Leu Ala Glu Leu Val Thr Pro Ile Leu Gln Glu Gly
            1300                1305                1310

Gly Val Pro Met Gly Glu Leu Phe Arg Glu Ile Thr Lys Pro Leu Arg
        1315                1320                1325

Pro Leu Gly Lys Ala Ala Ser Leu Leu Leu Glu Ile Leu Gly Leu Leu
        1330                1335                1340

Cys Lys Ser Met Gly Pro Lys Lys Val Gly Thr Leu Trp Arg Glu Ala
1345                1350                1355                1360

Gly Leu Ser Trp Lys Glu Phe Leu Pro Glu Gly Gln Asp Ile Gly Ala
                1365                1370                1375

Phe Val Ala Glu Gln Lys Val Glu Tyr Thr Leu Gly Glu Glu Ser Glu
            1380                1385                1390

Ala Pro Gly Gln Arg Ala Leu Pro Ser Glu Glu Leu Asn Arg Gln Leu
        1395                1400                1405

Glu Lys Leu Leu Lys Glu Gly Ser Ser Asn Gln Arg Val Phe Asp Trp
    1410                1415                1420

Ile Glu Ala Asn Leu Ser Glu Gln Gln Ile Val Ser Asn Thr Leu Val
1425                1430                1435                1440

Arg Ala Leu Met Thr Ala Val Cys Tyr Ser Ala Ile Ile Phe Glu Thr
                1445                1450                1455

Pro Leu Arg Val Asp Val Ala Val Leu Lys Ala Arg Ala Lys Leu Leu
        1460                1465                1470

Gln Lys Tyr Leu Cys Asp Glu Gln Lys Glu Leu Gln Ala Leu Tyr Ala
    1475                1480                1485

Leu Gln Ala Leu Val Val Thr Leu Glu Gln Pro Pro Asn Leu Leu Arg
    1490                1495                1500

Met Phe Phe Asp Ala Leu Tyr Asp Glu Asp Val Val Lys Glu Asp Ala
1505                1510                1515                1520

Phe Tyr Ser Trp Glu Ser Ser Lys Asp Pro Ala Glu Gln Gln Gly Lys
            1525                1530                1535

Gly Val Ala Leu Lys Ser Val Thr Ala Phe Phe Lys Trp Leu Arg Glu
        1540                1545                1550

Ala Glu Glu Glu Ser Asp His Asn
        1555                1560

<210> SEQ ID NO 3
<211> LENGTH: 93
<212> TYPE: DNA
<213> ORGANISM: Artificial Sequence
<220> FEATURE:
<223> OTHER INFORMATION: Description of Artificial Sequence:
      intercistronic region of plasmid pSGIRE

<400> SEQUENCE: 3
ctggacggta cccggggatc ctgcttcaac agtgcttgga cggatcttct agagtcagct    60

```
tcgacgagat tttcaggagc taaggaagct aaa                              93
```

<210> SEQ ID NO 4
<211> LENGTH: 220
<212> TYPE: DNA
<213> ORGANISM: Artificial Sequence
<220> FEATURE:
<221> NAME/KEY: misc_feature
<222> LOCATION: 4-58
<223> OTHER INFORMATION: n = a,t,c or g
<220> FEATURE:
<223> OTHER INFORMATION: Description of Artificial Sequence:
      intercistronic region of plasmid pSG66-IRE

<400> SEQUENCE: 4

```
taannnnnnn nnnnnnnnnn nnnnnnnnnn nnnnnnnnnn nnnnnnnnnn nnnnnnnnct   60
ggacggtacc cggggatccc tctcgagatt taacctcttc caacccaaag gcctcttcga  120
gttcgaagtt aacgatatcg gatcctgctt caacagtgct tggacggatc ttctagagtc  180
agcttcgacg agattttcag gagctaagga agctaaaatg                        220
```

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence:
      intercistronic region of plasmid pSGIREdelta33

<400> SEQUENCE: 5

```
ctggacggta cccggggatc ctgcttcaac agtgcttgga cggatcttct agaagctaaa   60
```

<210> SEQ ID NO 6
<211> LENGTH: 157
<212> TYPE: DNA
<213> ORGANISM: Artificial Sequence
<220> FEATURE:
<223> OTHER INFORMATION: Description of Artificial Sequence:
      intercistronic region of plasmid pSGMSC
<220> FEATURE:
<221> NAME/KEY: misc_feature
<222> LOCATION: 4-58
<223> OTHER INFORMATION: n = a,t,c or g

<400> SEQUENCE: 6

```
taannnnnnn nnnnnnnnnn nnnnnnnnnn nnnnnnnnnn nnnnnnnnnn nnnnnnnnct   60
ggacggtacc cggggatcca agagactaga ccatcaggct agtctcaatc tagagtcagc  120
ttcgacgaga ttttcaggag ctaaggaagc taaaatg                           157
```

<210> SEQ ID NO 7
<211> LENGTH: 226
<212> TYPE: DNA
<213> ORGANISM: Artificial Sequence
<220> FEATURE:
<221> NAME/KEY: misc_feature
<222> LOCATION: 4-58
<223> OTHER INFORMATION: n = a,t,c or g
<220> FEATURE:
<223> OTHER INFORMATION: Description of Artificial Sequence:
      intercistronic region of plasmid pSG3xIRE

<400> SEQUENCE: 7

```
taannnnnnn nnnnnnnnnn nnnnnnnnnn nnnnnnnnnn nnnnnnnnnn nnnnnnnnct   60
ggagatccaa aaaatacgtc tgcttcaaca gtgcttggac gacgtcaaaa aactgcagtg  120
cttcaacagt gcttggacac tgcataaaaa agctagctgc ttcaacagtg cttggacgct  180
```
agagtcagct tcgacgagat tttcaggagc taaggaagct aaaatg 226

<210> SEQ ID NO 8
<211> LENGTH: 182
<212> TYPE: DNA
<213> ORGANISM: Artificial Sequence
<220> FEATURE:
<223> OTHER INFORMATION: Description of Artificial Sequence:
      intercistronic region of plasmid pSGdeltat2+1

<400> SEQUENCE: 8
ctggacggta cccggggatc caaaaaatac gtctgcttca aagtgcttgg acgacgtcaa      60
aaaactgcag tgcttcaaag tgcttggaca ctgcataaaa aagctagctg cttcaacagt     120
gcttggacgc tagagttcta gagtcagctt cgacgagatt tcaggagct aaggaagcta      180 aa                                                                    182

<210> SEQ ID NO 9
<211> LENGTH: 245
<212> TYPE: DNA
<213> ORGANISM: Artificial Sequence
<220> FEATURE:
<221> NAME/KEY: misc_feature
<222> LOCATION: 4-58
<223> OTHER INFORMATION: n = a,t,c or g
<220> FEATURE:
<223> OTHER INFORMATION: Description of Artificial Sequence:
      intercistronic region of plasmid pSG1+delta2

<400> SEQUENCE: 9
taannnnnnn nnnnnnnnnn nnnnnnnnnn nnnnnnnnnn nnnnnnnnnn nnnnnnnnct      60
ggacggtacc cggggatcca aaaatacgt ctgcttcaac agtgcttgga cgacgtcaaa     120
aaactgcagt gcttcaacag tgcttggaca ctgcataaaa aagctagctg cttcaacagt    180
gcttggacgc tagagttcta gagtcagctt cgacgagatt tcaggagct aaggaagcta     240 aaatg                                                                245

<210> SEQ ID NO 10
<211> LENGTH: 181
<212> TYPE: DNA
<213> ORGANISM: Artificial Sequence
<220> FEATURE:
<223> OTHER INFORMATION: Description of Artificial Sequence:
      intercistronic region of plasmid pSGdelta3

<400> SEQUENCE: 10
ctggacggta cccggggatc caaaaaatac gtctgcttca aagtgcttgg acgacgtcaa      60
aaaactgcag tgcttcaaag tgcttggaca ctgcataaaa aagctagctg cttcaaagtg    120
cttggacgct agagttctag agtcagcttc gacgagattt caggagcta aggaagctaa     180 a                                                                     181

<210> SEQ ID NO 11
<211> LENGTH: 86
<212> TYPE: RNA
<213> ORGANISM: Artificial Sequence
<220> FEATURE:
<223> OTHER INFORMATION: Description of Artificial Sequence: stem-loop
      mRNA
<220> FEATURE:
<221> NAME/KEY: misc_feature
<222> LOCATION: 1-44
<223> OTHER INFORMATION: n = a,u,c or g -continued

```
<400> SEQUENCE: 11
nnnnnnnnnn nnnnnnnnnn nnnnnnnnnn nnnnnnnnnn nnnngccuag gccggagcgc      60
ccagaucugg gcgcuccggc cuaggc                                           86

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 12
gacggatcca aaaaatac                                                    18

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 13
ggtctagaac tctagcgtcc aagcac                                           26
```